(12) United States Patent
Li

(10) Patent No.: US 12,152,030 B2
(45) Date of Patent: Nov. 26, 2024

(54) POLYCYCLIC COMPOUND INHIBITING MNK1 AND MNK2

(71) Applicant: NOVOSTAR PHARMACEUTICALS, LTD., Shanghai (CN)

(72) Inventor: Bing Li, Shanghai (CN)

(73) Assignee: NOVOSTAR PHARMACEUTICALS, LTD., Shanghai (CN)

( * ) Notice: Subject to any disclaimer, the term of this patent is extended or adjusted under 35 U.S.C. 154(b) by 786 days.

(21) Appl. No.: 17/414,408

(22) PCT Filed: Dec. 4, 2019

(86) PCT No.: PCT/CN2019/123077
§ 371 (c)(1),
(2) Date: Jun. 16, 2021

(87) PCT Pub. No.: WO2020/155842
PCT Pub. Date: Aug. 6, 2020

(65) Prior Publication Data
US 2022/0041602 A1  Feb. 10, 2022

(30) Foreign Application Priority Data
Jan. 29, 2019 (CN) .......................... 201910087247.4

(51) Int. Cl.
*C07D 471/22* (2006.01)
(52) U.S. Cl.
CPC ................................ *C07D 471/22* (2013.01)
(58) Field of Classification Search
CPC .................................................. C07D 471/22
See application file for complete search history.

(56) References Cited

FOREIGN PATENT DOCUMENTS

| CN | 106795162 A | 5/2017 | | |
|---|---|---|---|---|
| CN | 108602805 A | 9/2018 | | |
| CN | 110256432 | * | 9/2019 | ......... A61K 31/4375 |
| CN | 110256432 A | | 9/2019 | |
| WO | 2017/075394 A1 | | 5/2017 | |
| WO | 2017087808 A1 | | 5/2017 | |
| WO | 2018152117 A1 | | 8/2018 | |

OTHER PUBLICATIONS

Written Opinion dated Mar. 9, 2020 received in International Application No. PCT/CN2019/123077, 4 pages.
International Search Report dated Mar. 9, 2020 issued in PCT/CN2019/123077.
Extended European Search Report dated Aug. 22, 2022 received in European Application No. 19 913 230.9.

* cited by examiner

*Primary Examiner* — Erich A Leeser
(74) *Attorney, Agent, or Firm* — Scully, Scott, Murphy & Presser, P.C.

(57) ABSTRACT

Provided is a polycyclic compound inhibiting MNK1 and MNK2. Specifically, provided is a compound represented by formula (I), or stereoisomers, tautomers, or pharmaceutically acceptable salts thereof, wherein the definition of each group is as described in the description. These compounds can be used for preparing pharmaceutical compositions for the treatment of diseases or disorders related to MNK activity or expression level.

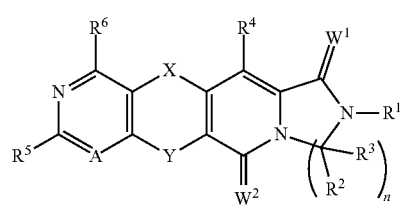

10 Claims, 4 Drawing Sheets

POLYCYCLIC COMPOUND INHIBITING MNK1 AND MNK2

TECHNICAL FIELD

The present disclosure generally relates to compounds having MAP kinase-interacting kinase (MNK) (e.g., MNK1 and MNK2) inhibiting activity and compositions thereof. The compounds have potential medical applications in the treatment of a variety of diseases, including proliferative diseases (such as cancer), inflammatory diseases and neurodegenerative diseases such as Alzheimer's disease.

BACKGROUND OF INVENTION

The present disclosure relates to compounds that inhibit the enzyme activity of MAP kinase-interacting serine/threonine-protein kinase (MNK). MNK protein is encoded by two genes, MKNK1 and MKNK2, which produce MNK1 and MNK2. Both proteins have two subtypes produced by alternative splicing. The shorter subtype is named as MNK1b/2b, which lacks a MAP kinase binding domain that leads to low basal activity. MNK1a is activated by ERK and p38, while MNK2a seems to be activated only by ERK.

The catalytic domains of MNK1 and MNK2 are very similar. These domains are very different from other kinases because they display DFD motifs at ATP binding sites rather than typical DFG motifs, which indicate the existence of altered activation loops. MNK1/2 is commonly expressed by phosphorylated eukaryotic initiation factor 4E (eIF4E), cytoplasmic phospholipase A2 (cPLA2) heteronuclear RNA-binding protein A1 (hnRNPA1), polypyrimidine tract-binding protein related splicing factor (PSF) and Sprouty 2 (hSPRY2).

MNK is associated with cancer through phosphorylation of eIF4E. eIF4E is a oncogene amplified in cancer and phosphorylated by MNK alone. When eIF4E is over expressed or over activated, their levels may increase. Elevated levels of eIF4E have been found in many types of tumors and cancer cell lines, including colon cancer, breast cancer, bladder cancer, lung cancer, prostate cancer, gastrointestinal cancer, head and neck cancer, Hodgkin's lymphoma and neuroblastoma. Phosphorylation of eIF4E leads to the optimal translation of mRNA involved in cell survival, angiogenesis and cancer metastasis. eIF4E, as a part of eIF4F complex, is a limiting factor to control the translation rate, and thus, eIF4E is an important regulator of mRNA translation. It is worth noting that although MNK activity is necessary for eIF4E mediated oncogenic transformation, it is not necessary for normal development. Therefore, pharmacological inhibition of MNK is an attractive treatment strategy for cancer.

Although the understanding of the structure and function of MNK is increasing, there are relatively few reported MNK inhibitors, including: CGP052088, CGP57380, and cercosporamide. These compounds are mainly used for MNK target verification, but lack of clinical application. Therefore, although some progress has been made in this field, there are still significant needs in this field for MNK inhibitor compounds that can specifically inhibit the activity of MNK kinase, especially those capable of regulating cancer pathway.

SUMMARY OF INVENTION

The object of the application is to provide a MNK inhibitor compound having potential medical applications in the treatment of a variety of diseases.

According to the first aspect of the application, it is provided a compound of formula (I):

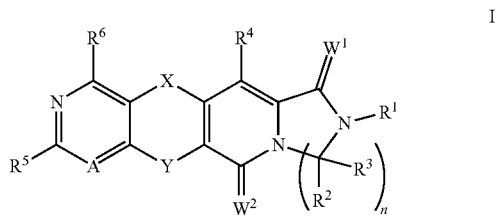

or a stereoisomer, tautomer, prodrug, solvate, hydrate, stable isotope derivative or pharmaceutically acceptable salt thereof, wherein:

A is —N— or —CR$^7$—;

X is —(CR$^{1a}$R$^{1b}$)$_p$-M-(CR$^{2a}$R$^{2b}$)$_q$—, wherein M is a chemical bond or selected from the group consisting of —N(R$^9$)—, —O—, —S—, —C(O)—, —S═O, —S(O)$_2$—, —C(O)NH—, —C(═CH$_2$)—, or —NHC(O)—;

p and q are each independently 0, 1 or 2;

Y is selected from the group consisting of —N(R$^8$)—, —O—, —S—, —C(O)—, —S═O, —S(O)$_2$—, or —CHR$^9$—;

W$^1$ and W$^2$ are independently selected from the group consisting of O, S or N—OR', wherein R' is hydrogen or C1-C8 alkyl;

R$^1$ is selected from the group consisting of hydrogen, —OH, acetyl, C1-C8 alkyl, —C(O)(C1-C8 alkyl), —C(O)(C3-C8 cycloalkyl), —COOH, —C(O)O—(C1-C8)alkyl, C3-C8 cycloalkyl, 5-12 membered aryl, 5-12 membered heteroaryl, or 5-12 membered heterocyclyl;

n is 1, 2 or 3;

R$^2$ and R$^3$ are each independently selected from the group consisting of hydrogen, C1-C8 alkyl, C2-C8 alkenyl, C2-C8 alkynyl, C6-C10 aryl, 5-12 membered heteroaryl, C1-C4 alkylene-(5-12) membered heteroaryl, C3-C8 cycloalkyl, C1-C4 alkylene-(C3-C8)cycloalkyl, 5-12 membered heterocyclyl, C1-C4 alkylene-(5-12) membered heterocyclyl; or R$^2$ and R$^3$ together with the carbon atom connected thereto form the radicals selected from the group consisting of: C3-C10 monocyclic alkyl, C3-C10 bicyclic or polycyclic alkyl, 5-12 membered heteromonocyclic alkyl containing 1-3 N, O or S atoms, 5-12 membered heterobicyclic or heteropolycyclic alkyl containing 1-3 N, O or S atoms; the substituted monocyclic alkyl, bicyclic or polycyclic alkyl, or the substituted heteromonocyclic alkyl, substituted heterobicyclic or heteropolycyclic alkyl contain 1-3 unsaturated double bonds or triple bonds; the substituted monocyclic alkyl, substituted bicyclic or polycyclic alkyl, or the substituted heteromonocyclic alkyl, substituted heterobicyclic or heteropolycyclic alkyl are substituted at any position by one or more radicals selected from the group consisting of: deuterium, halogen, hydroxy, alkyl, heterocyclic alkyl, cycloalkyl, alkoxy, amino, aryl, heteroaryl, —SR$^{3a}$, —N(R$^{3b}$)$_2$, —S(O)$_2$N(R$^{3b}$)$_2$, —NR$^{3b}$C(O)N(R$^{3b}$)$_2$, —NR$^{3b}$C(O)R$^{3a}$, —C(O)R$^{3a}$, —S(O)$_{0-2}$R$^{3a}$, —C(O)OR$_{3b}$, —(CH$_2$)$_u$OH or —(CH$_2$)$_u$N(R$^{3b}$)$_2$;

R$^{1a}$, R$^{1b}$, R$^{2a}$ and R$^{2b}$ are each independently selected from the group consisting of hydrogen, deuterium, halogen, hydroxy, —SH, hydroxy-(C1-C4)alkylene, cyano, C1-C4 alkyl, C1-C4 alkoxy;

$R^{3a}$ and $R^{3b}$ are each independently selected from the group consisting of hydrogen, alkyl, haloalkyl, cycloalkyl, heterocyclic alkyl, aryl, heteroaryl, (heterocyclic alkyl)alkyl, (cycloalkyl)alkyl, arylalkyl, or arylalkyl, or two $R^b$ together with the N atom connected thereto form 3-8 membered heteromonocyclic alkyl;

$R^4$ is independently selected from the group consisting of hydrogen, halogen, hydroxy, —SH, hydroxy-(C1-C4) alkylene, cyano, C1-C4 alkyl, C1-C4 haloalkyl, C1-C4 alkoxy, C1-C4 haloalkoxy, —C(O)(C1-C8 alkyl), —C(O)(C3-C8 cycloalkyl), —COOH, —C(O)O—(C1-C8)alkyl, —S(C1-C8 alkyl), C2-C8 alkenyl, C2-C8 alkynyl, C3-C8 cycloalkyl, C6-C10 aryl, 5-12 membered heteroaryl or 5-12 membered heterocyclyl;

$R^5$, $R^6$ and $R^7$ are each independently selected from the group consisting of —H, —OH, —CN, —$SR^{10}$, halogen, —S(O)$_2$(C1-C8)alkyl, —NH—S(O)$_2$(C1-C8)alkyl, —C(O)N($R^{10}$)$_2$, —NHC(O)$R^{10}$, —N($R^{10}$)$_2$, —(C1-C4 alkylene)N($R^{10}$)$_2$, C1-C8 alkyl, C2-C8 alkenyl, C2-C8 alkynyl, C1-C8 haloalkyl, —O(C1-C8 alkyl), —O(C1-C8 haloalkyl), —O(C1-C8 alkylene)NH$R^{10}$, —O(C1-C8 alkylene)N($R^{10}$)$_2$, C6-C10 aryl, 5-12 membered heteroaryl, C1-C4 alkylene-(5-12) membered heteroaryl, C3-C8 monocyclic alkyl, C3-C10 bicyclic or polycyclic alkyl, C1-C4 alkylene-(C3-C8)cycloalkyl, 5-12 membered heterocyclyl, C1-C4 alkylene-(5-12) membered heterocyclyl; or $R^5$ and $R^7$ together with the carbon atom connected thereto form C6-C10 aryl, 5-12 membered heteroaryl, C3-C8 cycloalkyl, 5-12 membered heterocyclyl;

$R^{10}$ is selected from the group consisting of —H, —OH, —C(O)O(C1-C8 alkyl), —C(O)(C1-C8 alkyl), —C(O)—NH$_2$, —C(O)—NH(C1-C8 alkyl), —NH—(C1-C8 alkyl), —NH—C(O)(C1-C8 alkyl), NH$_2$—C(O)—(C1-C4 alkylene), —S(C1-C8 alkyl), acetyl, C1-C8 alkyl, C2-C8 alkenyl, C2-C8 alkynyl, —O(C1-C8 alkyl), —(C1-C8 haloalkyl), C1-C8 alkylamino, —C(O)(C1-C8 alkyl), —C(O)(C3-C8 cycloalkyl), —C(O)O—(C1-C8 alkyl), C3-C8 cycloalkyl, C6-C10 aryl, 5-12 membered heteroaryl or 5-12 membered heterocyclyl;

wherein, each of alkyl, alkylene, cycloalkyl, aryl, heteroaryl, heterocyclyl, amino are optionally substituted with 1, 2 or 3 J groups, the J group is selected from the group consisting of —$SR^9$, —S(O)$R^9$, —S(O)$_2R^9$, —S(O)N($R^9$)$_2$, —N($R^9$)$_2$, —C(O)O$R^9$, —C(O)$R^9$, —C(O)—N($R^9$)$_2$, hydroxy, cyano, halogen, acetyl, C1-C4 alkyl, C2-C4 alkenyl, C2-C4 alkynyl, C1-C4 alkoxy, haloalkyl, —S—(C1-C4 alkyl), cyano-(C1-C4 alkylene), C1-C4 alkylamino, NH$_2$—C(O)—(C1-C4)alkylene, N($R^9$)$_2$—C(O)—(C1-C4)alkylene, —CH$R^9$—C(O)—(C1-C4)alkyl, —C(O)—(C1-C4)alkyl, 5-12 membered heterocyclyl, C1-C4 alkylene-(5-12) membered heterocyclyl, C3-C8 cycloalkyl, C1-C4 alkylene-(C3-C8)cycloalkyl, C2-C4 alkylene-(C3-C8) cycloalkyl, —CH$R^9$—C(O)—(C3-C8)cycloalkyl, —C(O)—(C3-C8)cycloalkyl, —CH$R^9$—C(O)—(C6-C10)aryl, —CH$R^9$—(C6-C10)aryl, —C(O)—(C6-C10)aryl, —CH$R^9$—C(O)-(5-12) membered heterocyclyl, —C(O)-(5-12) membered heterocyclyl; or two J groups connected to the same atom forming oxo (=O); and $R^8$ and $R^9$ are hydrogen, C1-C4 alkyl, hydroxy-(C1-C4) alkyl, C3-C8 cycloalkyl, 5-12 membered heterocyclyl, —NH$_2$ or —OH.

In another preferred example, n is 1, and Y is —N($R^8$)—.

In another preferred example, X is selected from the group consisting of: —C(=O)—, —CH$_2$—, —CD$_2$-, —C(=CH$_2$)—, —CH(OH)—, —CH(CH$_3$)— or —CF$_2$—.

In another preferred example, $W^1$ and $W^2$ are O.

In another preferred example, $R^2$ and $R^3$ are each independently selected from the group consisting of: hydrogen, methyl, ethyl, propyl, isopropyl, tert-butyl, vinylidene, propynylidene, 2-methyl-1-propenylidene, benzyl, fluorobenzyl, chlorobenzyl, cyclopentyl, cyclohexyl, difluorocyclohexyl, trifluoromethyl, 1,1,1-trifluoroethenyl, thienyl, thiazolyl, methylenenitrile, chlorophenyl, fluorophenyl, fluorochlorophenyl, difluorophenyl, pyridyl, methylpyridyl, chloropyridyl, N-methylaminomethylene, aminomethylene, 1-aminoethenyl, methylaminomethylene, 1-hydroxyethenyl, or 1,1-difluoroethenyl; or $R^2$ and $R^3$ together with the carbon atom connected thereto form rings selected from the group consisting of:

cyclopropyl ring, cyclobutyl ring, cyclopentyl ring, cyclohexyl ring, bicyclo[2.2.2]octane ring, norborneol ring, or

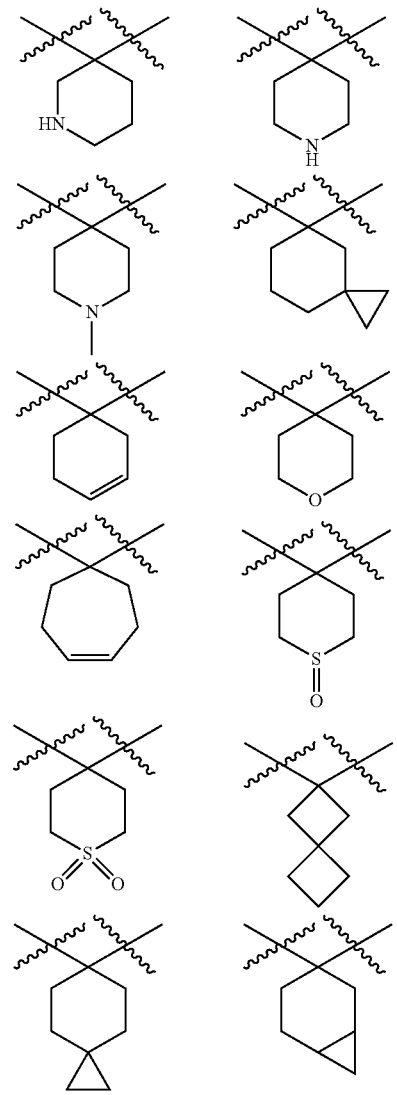

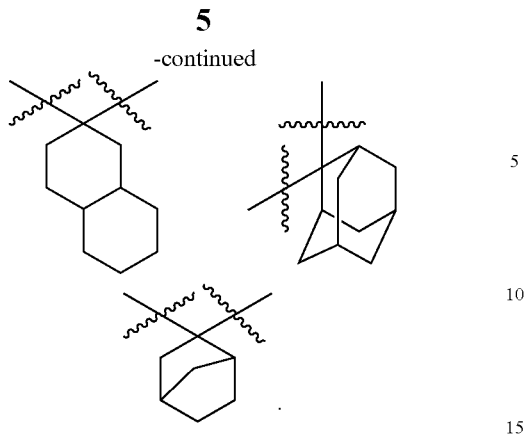

In another preferred example, the ring formed by $R^2$ and $R^3$ together with the carbon atom connected thereto is substituted with a substituent selected from the group consisting of: halogen, hydroxy, or trifluoromethyl.

In another preferred example, $R^2$ and $R^3$ are each independently methyl, ethyl, propyl, isopropyl, tert-butyl, trifluoromethyl, 1,1,1-trifluoroethenyl, cyclopropyl, cyclopentyl, cyclohexyl, difluorocyclohexyl, chlorophenyl, or fluorophenyl.

In another preferred example, n is 1, and $R^2$ and $R^3$ together with the carbon atom connected thereto form a cycloalkyl or heterocyclic ring, which is optionally substituted with 1, 2 or 3 J groups.

In another preferred example, $R^2$ and $R^3$ together with the carbon atom connected thereto form a heterocyclic ring, which is optionally substituted with 1, 2 or 3 radicals selected from the group consisting of: halogen, —CN, hydroxy, N-methylamino, methyl, difluoroethenyl, and methylenenitrile.

In another preferred example, the heterocyclyl is substituted with at least two J groups on the same atom, and wherein the at least two J groups form oxo together.

In another preferred example, when A is $C(R^7)$, $R^7$ and $R^5$ together with the atoms connected thereto form a fused heteroaryl ring, which is optionally substituted with 1, 2 or 3 J groups.

In another preferred example, $R^4$ is selected from hydrogen, halogen or alkyl.

In another preferred example, when Y is $N(R^8)$, $R^8$ is hydrogen.

In another preferred example, $R^6$ is hydrogen.

In another preferred example, $R^5$ is selected from the group consisting of: amino, C1-C8 alkyl, halogen, C3-C8 cycloalkylcarbonylamine, 5-12 membered heterocyclyl amine, hydroxy-(C1-C4 alkylene), or C3-C8 cycloalkyl-(C1-C4 alkylene).

In another preferred example, when A is —$CR^7$, $R^7$ is hydroxy, halogen, cyano, C1-C8 alkyl, C2-C8 alkenyl, C2-C8 alkynyl, C1-C8 haloalkyl, —O(C1-C8 alkyl), C1-C4 alkylene-(5-12) membered heteroaryl, C3-C8 cycloalkyl, C1-C4 alkylene-(C3-C8)cycloalkyl, 5-12 membered heterocyclyl, C1-C4 alkylene-(5-12) membered heterocyclyl.

In another preferred example, A is —N— or —$CR^7$, and when A is —$CR^7$, $R^7$ is hydroxy, halogen, cyano, methyl or ethyl.

In another preferred example, the compound is selected from the group consisting of:

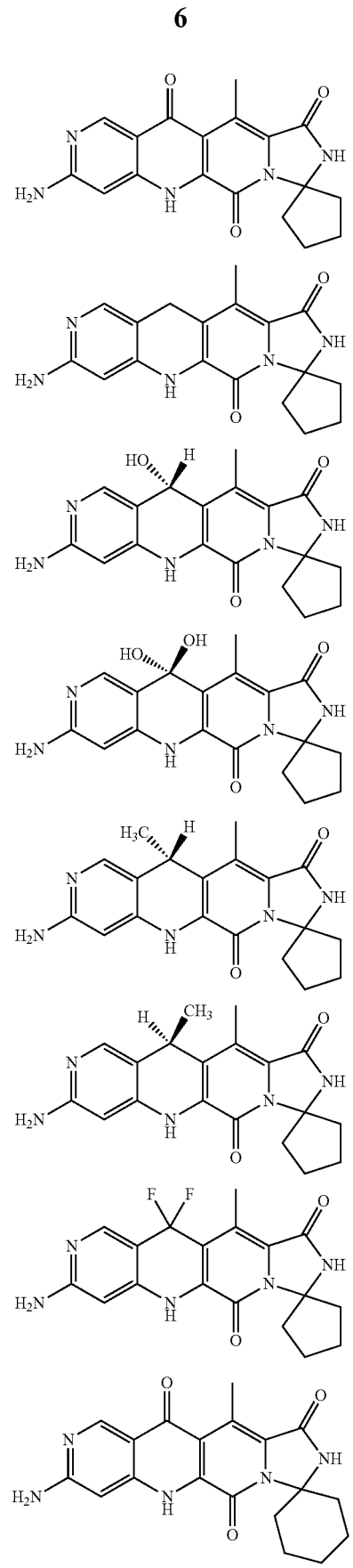

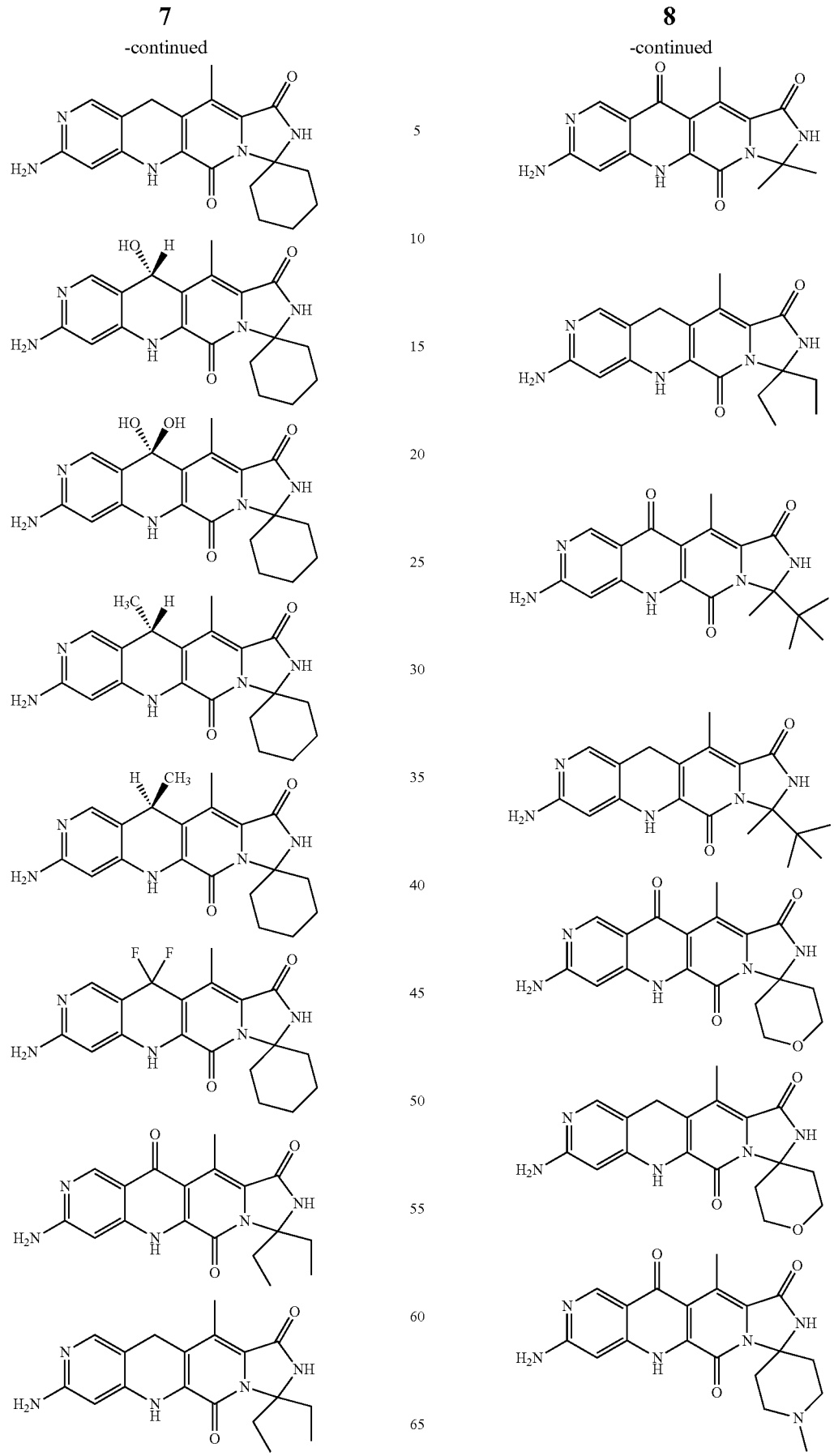

US 12,152,030 B2

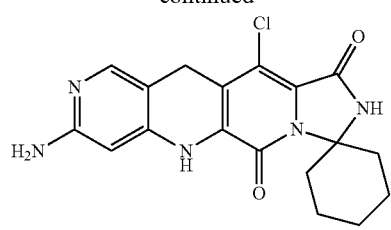
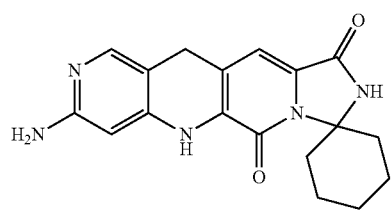
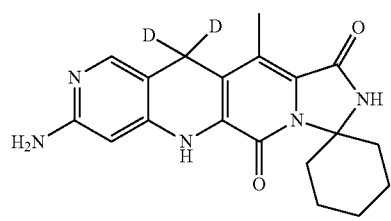
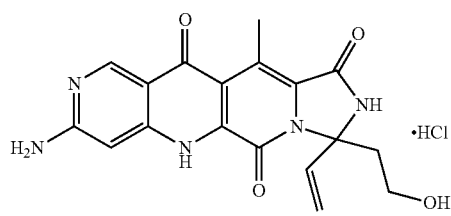
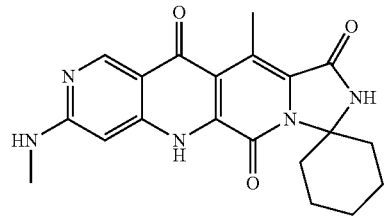
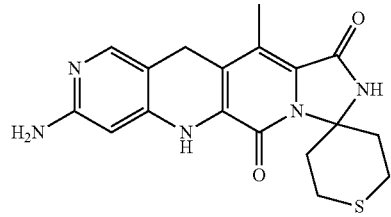
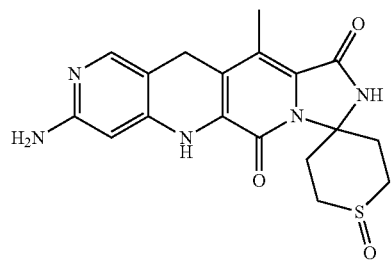
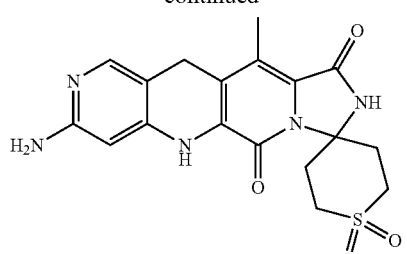
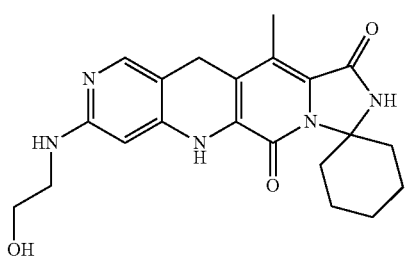
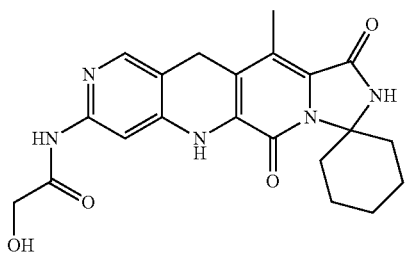
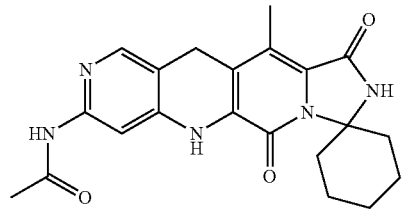
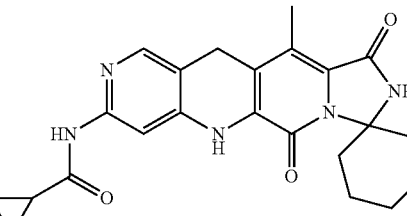
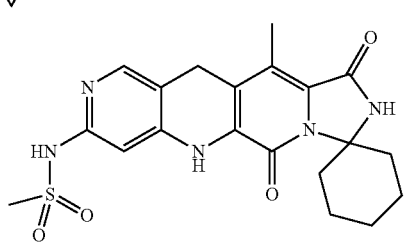
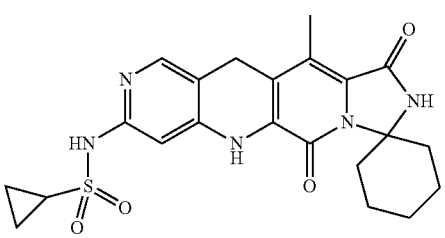

-continued
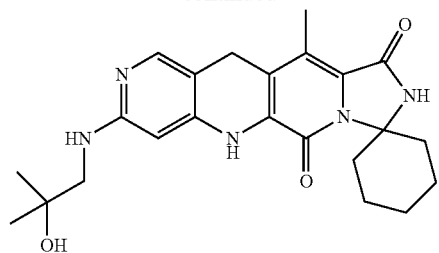
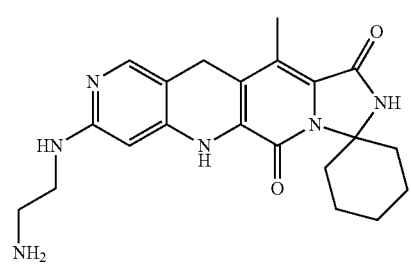
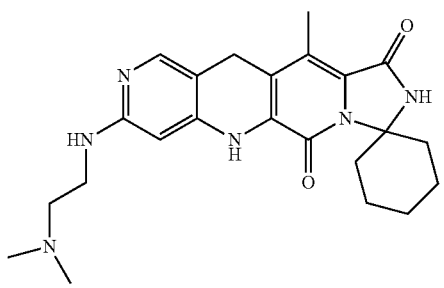
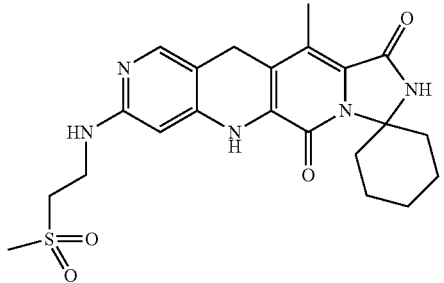
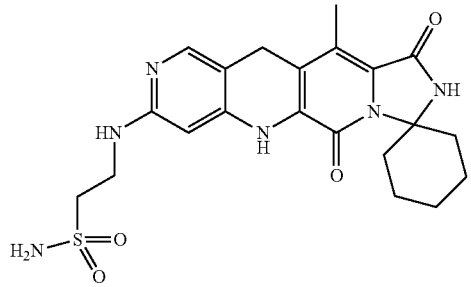
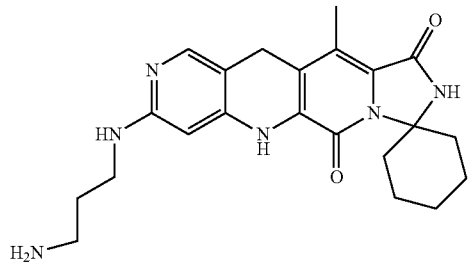
-continued
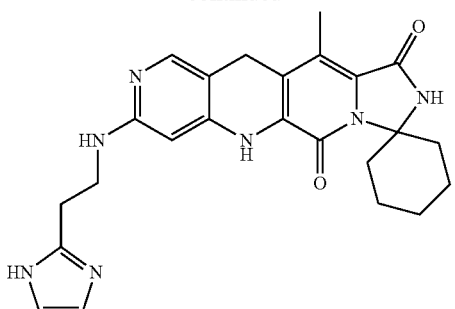
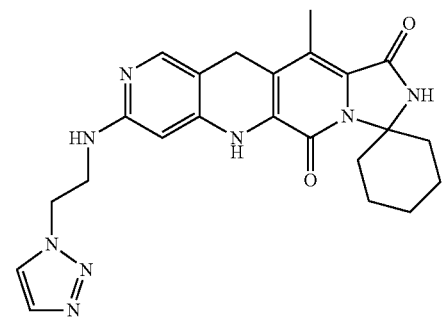
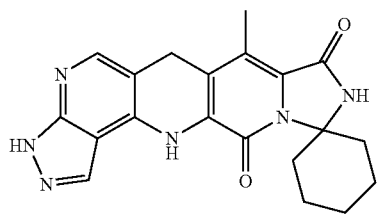
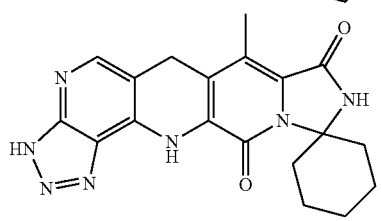
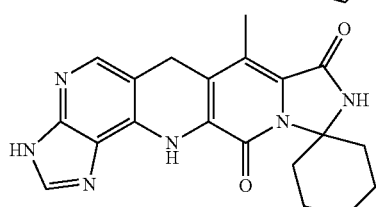
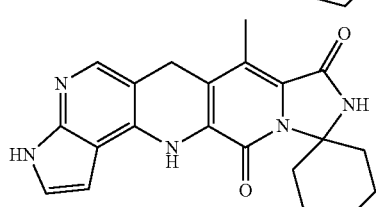
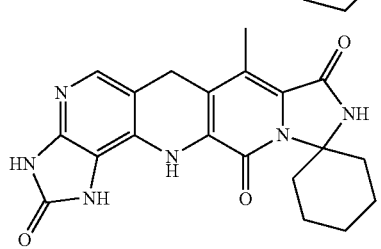

-continued
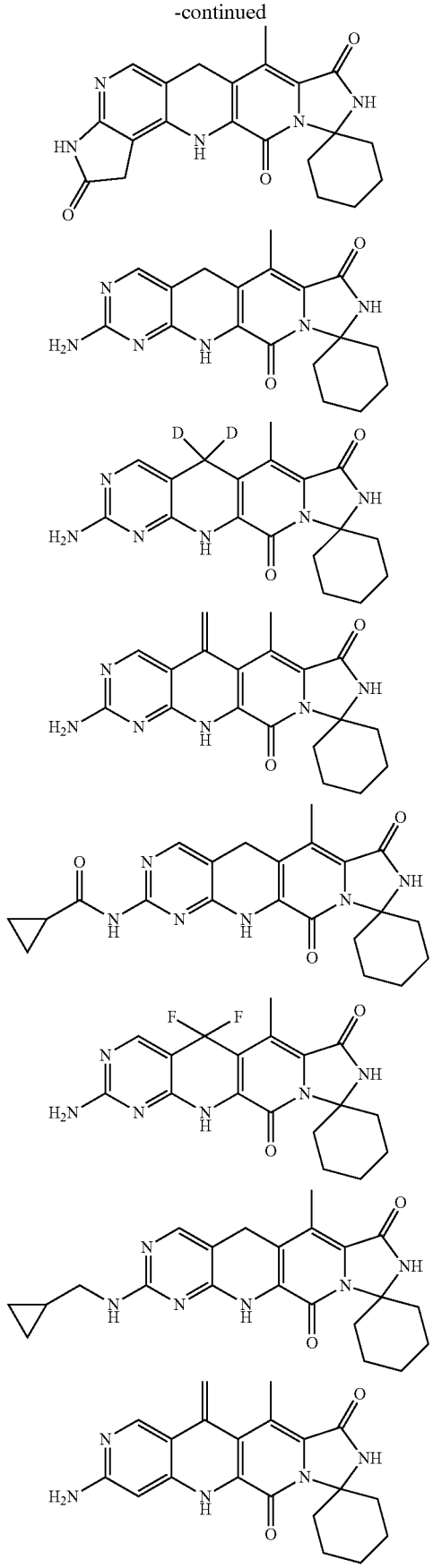
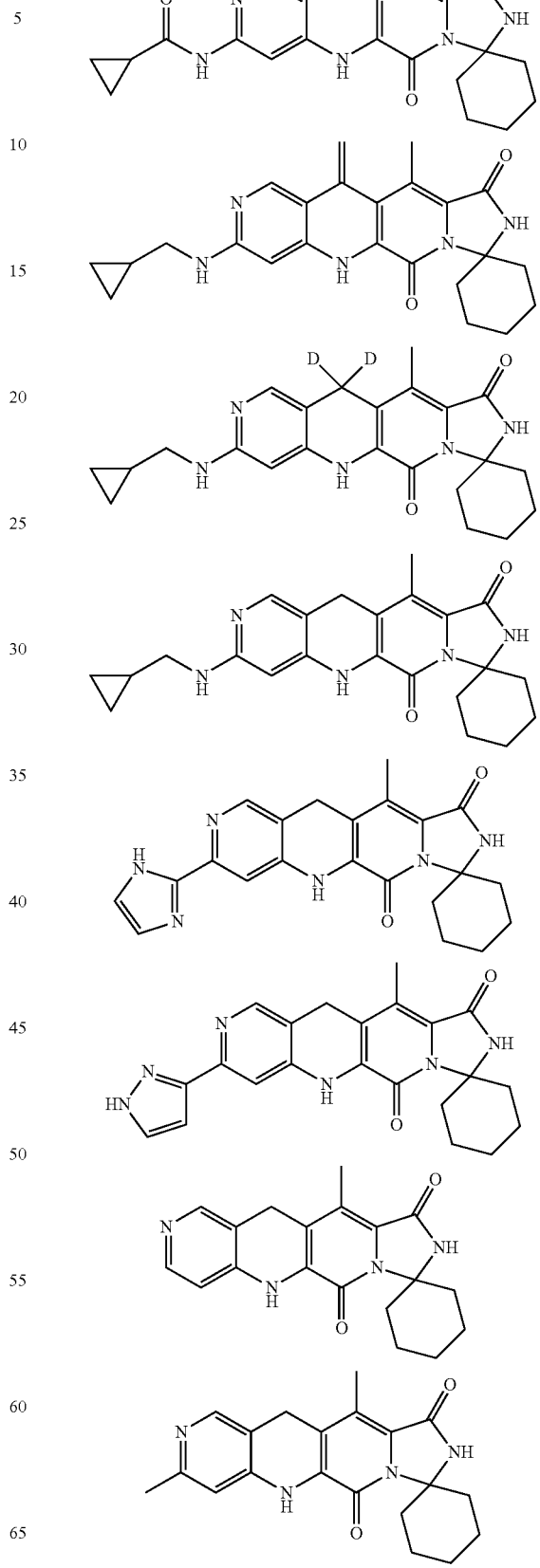

17
-continued

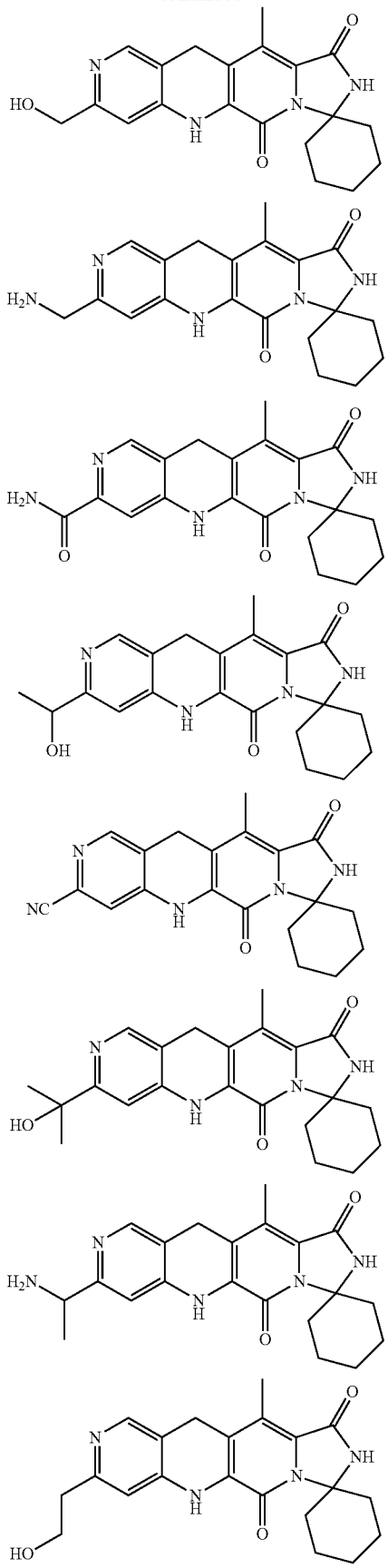

18
-continued

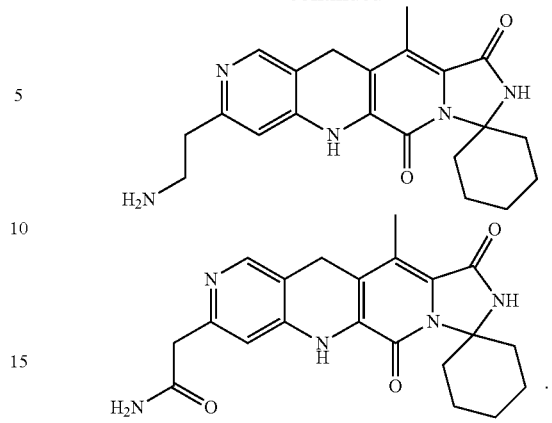

A second aspect of the present application provides a pharmaceutical composition comprising: (i) a therapeutically effective amount of the compound as described in the first aspect of the present application, or the stereoisomer, tautomer or pharmaceutically acceptable salt thereof; and optionally (ii) a pharmaceutically acceptable carrier or excipient.

In another preferred example, the pharmaceutical composition further comprises a second therapeutic agent.

In another preferred example, the pharmaceutical composition is used for the treatment of diseases or disorders in which the activity or expression level of MNK is implicated.

According to the third aspect of the application, it is provided a use of a compound as described in the first aspect of the application, characterized in that the compound is used in the preparation of a pharmaceutical composition for treating or preventing diseases or disorders in which the activity or expression level of MNK is implicated.

In another preferred example, the disease or disorder is selected from but not limited to: colorectal cancer, gastric cancer, thyroid cancer, lung cancer, cholangiocarcinoma, liver cancer, esophageal cancer, bladder cancer, urothelial cancer, cervical cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, multiple myeloma, brain cancer, CNS cancer, head and neck cancer, kidney cancer, prostate cancer, ovarian cancer, breast cancer, bone cancer, uncontrolled cell growth, proliferation and/or survival, inappropriate cellular immune response, inappropriate cellular inflammatory response, leukemia and myelodysplastic syndrome, malignant lymphoma, head and neck tumor, lung tumor and lung metastatic tumor, chest tumor, non-small cell tumor and small cell lung tumor, gastrointestinal tumor, endocrine tumor, breast and other gynecological tumor, urinary tumor, kidney, bladder and prostate tumor, skin tumor, sarcomas, tumor metastasis, autoimmune disease, neurodegenerative disease, Alzheimer's disease, Parkinson's disease, neuropathic pain, etc.

Another aspect of the present application provides a method for alleviating or inhibiting MNK activity in at least one cell over expressing MNK, comprising contacting the at least one cell with the compound or stereoisomer, tautomer, prodrug, solvate, hydrate, stable isotope derivative or pharmaceutically acceptable salt according to the first aspect of the present application.

In another preferred example, the at least one cell is colon cancer cell, gastric cancer cell, thyroid cancer cell, lung cancer cell, cholangiocarcinoma cell, liver cancer cell, esophageal cancer cell, bladder cancer cell, urothelial cancer cell, cervical cancer cell, leukemia cell, B-cell lymphoma, T-cell lymphoma, hairy cell lymphoma, Hodgkin's lymphoma cell, non-Hodgkin's lymphoma cell, Burkitt's lymphoma cells, pancreatic cancer cells, melanoma cells, multiple myeloma cells, brain cancer cells, CNS cancer cells, renal cancer cells, prostate cancer cells, ovarian cancer cells or breast cancer cells.

According to another aspect of the present application, it is provided a method for treating MNK dependent diseases in mammal in need, comprising administrating the mammal (i) at least one compound or a stereoisomer, tautomer, prodrug, solvate, hydrate, stable isotope derivative or pharmaceutically acceptable salt thereof according to the first aspect of the application; or (ii) the pharmaceutical composition described in the second aspect of the application.

In another preferred example, the neurodegenerative disease is tau protein disease, more preferably Alzheimer's disease.

In another preferred example, the neurodegenerative disorder is Parkinson's disease.

In another preferred example, the compound is used in treating diseases caused by abnormal MNK activity, related to abnormal MNK activity, or accompanied by abnormal MNK activity.

In another preferred example, the medicament is used in treating a disease selected from the group consisting of: colorectal cancer, gastric cancer, thyroid cancer, lung cancer, cholangiocarcinoma, liver cancer, esophageal cancer, bladder cancer, urothelial cancer, cervical cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, multiple myeloma, brain cancer, CNS cancer, head and neck cancer, kidney cancer, prostate cancer, ovarian cancer, breast cancer, bone cancer, uncontrolled cell growth, proliferation and/or survival, inappropriate cellular immune response, inappropriate cellular inflammatory response, leukemia and myelodysplastic syndrome, malignant lymphoma, head and neck tumor, lung tumor and lung metastatic tumor, chest tumor, non-small cell tumor and small cell lung tumor, gastrointestinal tumor, endocrine tumor, breast and other gynecological tumor, urinary tumor, kidney, bladder and prostate tumor, skin tumor, sarcomas, tumor metastasis, autoimmune disease, neurodegenerative disease, Alzheimer's disease, Parkinson's disease, neuropathic pain.

In another preferred example, the medicament is used in the treatment of uncontrolled cell growth, proliferation and/or survival, inappropriate cellular immune response or inappropriate cellular inflammatory response, or in the treatment or prevention of neurodegenerative disease, preferably tau protein disease, and even more preferably Alzheimer's disease.

In another preferred example, the medicament is used in the treatment of neuropathic pain.

In another aspect of the present application, it is provided a method for treating diseases in mammal, which is uncontrolled cell growth, proliferation and/or survival, inappropriate cellular immune response or inappropriate cellular inflammatory response, or neurodegenerative disease, preferably tau protein disease, or even more preferably Alzheimer's disease, comprising administering a therapeutically effective amount of the compound as described in the first aspect of the application to the mammal.

In another aspect of the present application, it is provided a method for treating a mammal in a state of sickness, which is alleviated by inhibiting MNK, comprising administering a therapeutically effective amount of the compound according to the first aspect of the present application to the mammal.

In another aspect of the present application, it is provided a use of the compound in detecting and identifying candidate compounds of MNK inhibitors.

It should be understood that within the scope of the invention, the above technical features of the invention and the technical features described in details in the following parts (such as the examples) can be combined with each other to form new or preferred solutions. For the sake of space, it is not repeated and described hereinafter.

DETAILED EMBODIMENTS

Figure 1:
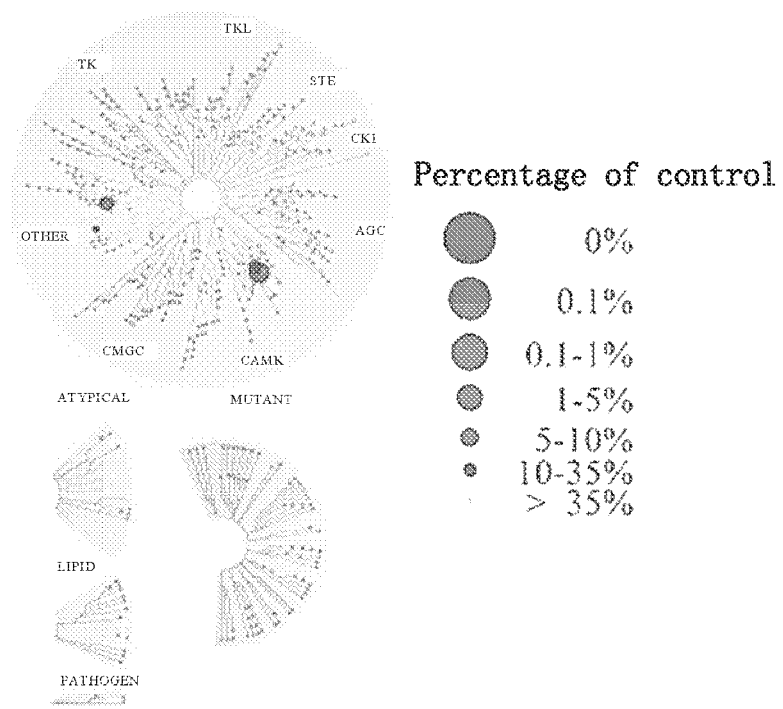
FIG. 1 shows the inhibition percentage of compound 2 on different wild protein kinases.
Figure 2:
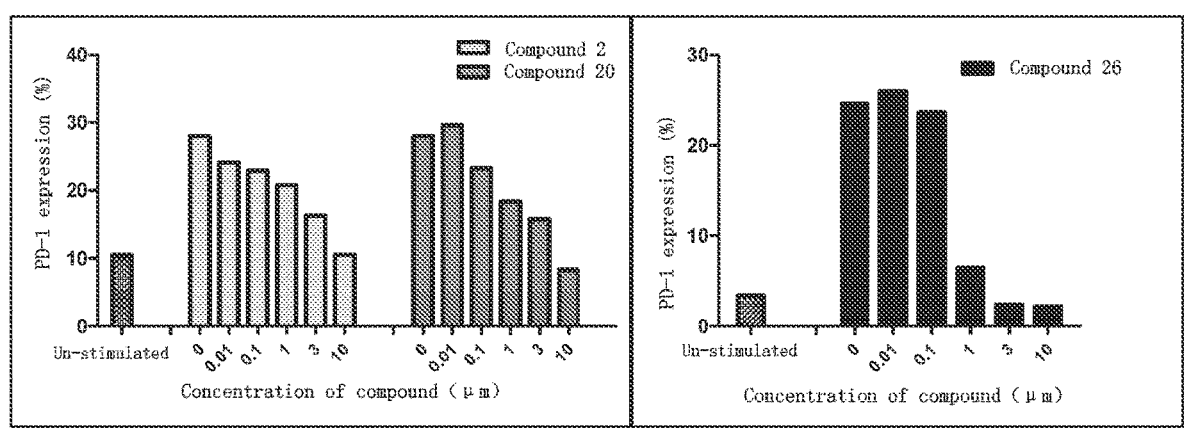
FIG. 2 shows the inhibition results of PD-1 expression by the compound of the present application.
Figure 3:
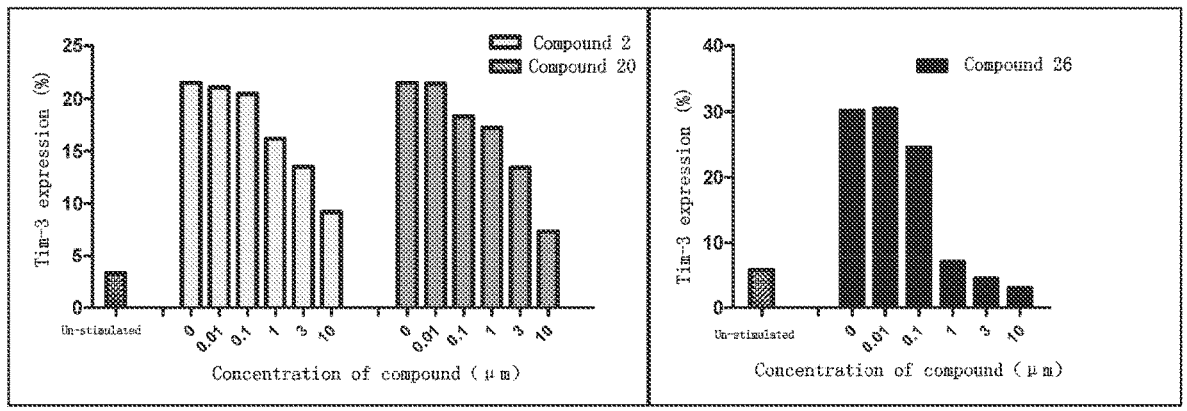
FIG. 3 shows the inhibition of Tim-3 expression by the compound of the present application.
Figure 4:
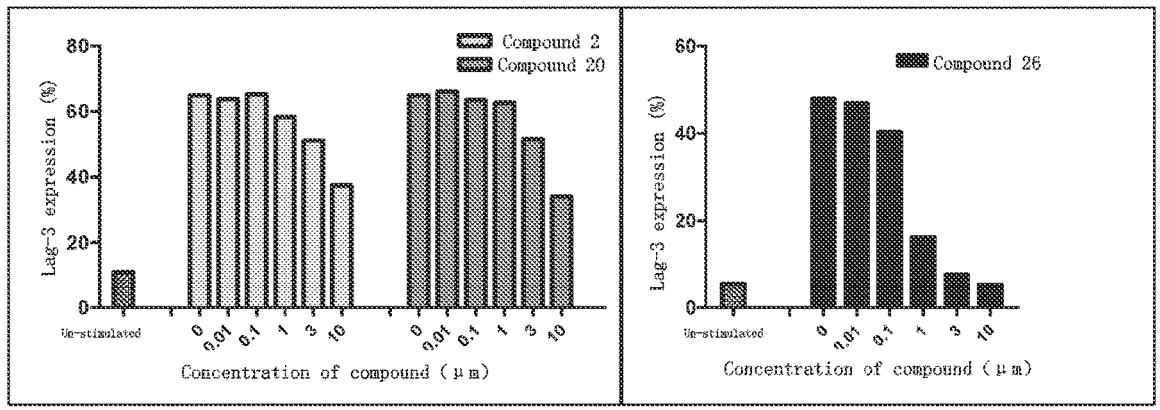
FIG. 4 shows the inhibition of Lag-3 expression by the compound of the present application.
Figure 5:
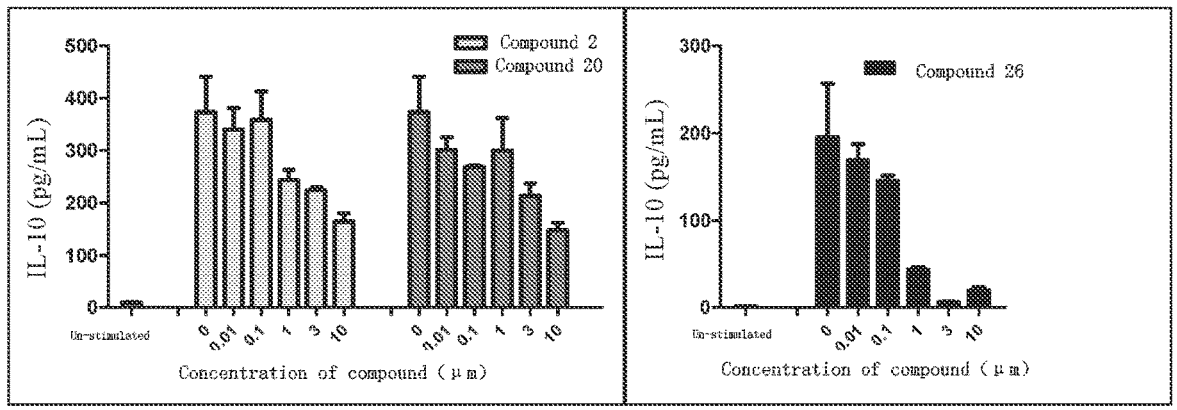
FIG. 5 shows the inhibition of the secretion level of cytokine IL-10 by the compound of the present application.
Figure 6:
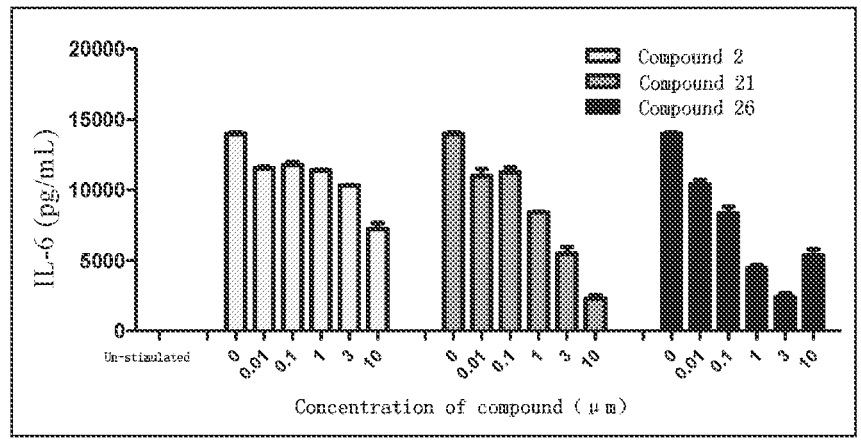
FIG. 6 shows the inhibition of the secretion level of cytokine IL-6 by the compound of the present application.
Figure 7:
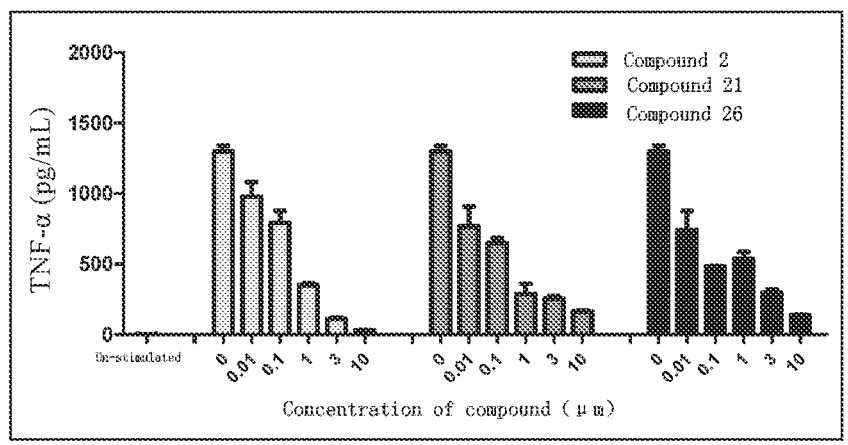
FIG. 7 shows the inhibition of the secretion level of cytokine TNF-α by the compound of the present application.

The present application relates to compounds that inhibit or regulate MNK activity, and stereoisomers, tautomers, prodrugs, solvates, hydrates, stable isotope derivatives and pharmaceutically acceptable salts thereof. The present application also relates to pharmaceutically acceptable compositions comprising the compounds, and related methods for the treatment of diseases that can be beneficial from the inhibition of MNK, such as cancer, inflammatory diseases and neurodegenerative diseases, like Alzheimer's disease and Parkinson's disease.

Terminology

Unless otherwise specified, the term "substitution" herein refers to the substitution of one or more hydrogen atoms on a radical with the substituents selected from the group consisting of: halogen, amino, hydroxy, nitro, cyano, trifluoromethyl, $C_1$-$C_{12}$ alkyl or cycloalkyl, $C_1$-$C_{12}$ alkoxy, oxygen atom (i.e. =O), unsubstituted $C_1$-$C_{12}$ alkylamino or $C_1$-$C_{12}$ alkylamino substituted with $C_1$-$C_4$ alkylamino, $C_2$-$C_6$ ester, $C_2$-$C_6$ acyl, $C_2$-$C_6$ amide, $C_1$-$C_{12}$ thioalkyl, carboxyl, $C_5$-$C_{12}$ aryl or heteroaryl, $C_5$-$C_{12}$ heterocyclyl (containing 1-5, preferably 1-3 heteroatoms selected from N, O or S).

The term "$C_1$-$C_8$ alkyl" refers to a linear or branched alkyl group with 1 to 8 carbon atoms, such as methyl, ethyl, propyl, isopropyl, butyl, isobutyl, sec-butyl, tert-butyl, or the like groups.

The term "$C_{3\text{-}}C_8$ cycloalkyl" refers to cycloalkyl group with 3 to 8 carbon atoms, such as cyclopropyl, cyclobutyl, cyclopentyl, cycloheptyl, or the like groups.

The term "$C_1$-$C_8$ alkoxy" refers to a linear or branched alkoxy group with 1 to 8 carbon atoms, such as methoxy, ethoxy, propoxy, isopropoxy, butyloxy, isobutyloxy, sec-butyloxy, tert-butyloxy, or the like groups.

The term "halogen" refers to F, Cl, Br and I.

The term "$C_1$-$C_8$ alkylamino" refers to a $C_1$-$C_8$ alkyl group substituted with an amino group, such as a group having the structure of "$C_1$-$C_8$ alkyl-NH—" or "(alkyl)$_2$-N—" (total number of carbon atoms is 1-8), "—$C_1$-$C_8$ alkylene-NH$_2$", "alkyl-N-alkylene- (total number of carbon atoms is 1-8)", or "(alkyl)$_2$-N-alkylene- (total number of carbon atoms is 1-8)", such as CH$_3$NH—, C$_2$H$_5$NH—, C$_3$H$_7$NH—, (CH$_3$)$_2$N—, —CH$_2$NH$_2$, —C$_2$H$_5$NH$_2$, —C$_3$H$_7$NH$_2$, —C$_2$H$_4$N(CH$_3$)$_2$, or the like groups. Wherein, the definition of $C_{1-8}$ alkyl is as described above.

The term "$C_1$-$C_8$ acyl" refers to a substituent of a structure such as "linear or branched alkyl/cycloalkyl/aryl/heteroaryl-carbonyl-amino having 0-7 carbon atoms", such as acetyl, propionyl, butanoyl, or the like groups.

The term "$C_6$-$C_{10}$ aryl" refers to an aryl group having 6-10 carbon atoms, such as phenyl, naphthyl, etc., which may be substituted or unsubstituted.

The term "5-12 membered heteroaryl" refers to a heteroaryl group having 1-12 carbon atoms and one or more (preferably 1-3) heteroatoms selected from O, S and/or N, preferably 5-8 membered heteroaryl group. The heteroaryl group can be substituted or unsubstituted.

The term "5-12 membered heterocycle" refers to a 5-12 membered cyclic saturated, partially unsaturated or aromatic group, wherein the heterocycle has at least one ring atom selected from the group consisting of O, S and/or N.

The term "5-12 membered heteroaryl" refers to a 5-12 membered cyclic aromatic group, wherein the heteroaryl has at least one ring atom selected from the group consisting of O, S and/or N.

In particular, the expression of "C1-Cn" means that the group has 1-n carbon atoms. For example, the expression of "C1-C8" means that the group has 1, 2, 3, 4, 5, 6, 7 or 8 carbon atoms; "C6-C10" means that the group has 6, 7, 8, 9 or 10 carbon atoms.

In the present application, the term "pharmaceutically acceptable" component refers to the substances that are suitable for human and/or animals without excessive adverse reactions (such as toxicity, stimulation and allergy), i.e. substances with a reasonable benefit/risk ratio.

In the present application, the term "effective amount" refers to the amount of a therapeutic agent for treating, alleviating or preventing a target disease or disorder, or the amount showing a detectable therapeutic or preventive effect. The exact effective amount for an object depends on the body shape and health status of the object, the nature and degree of the disease, and the selected therapeutic agent and/or combination of therapeutic agents. Therefore, it is useless to specify an accurate effective amount in advance. However, for a given condition, conventional experiments can be used to determine the effective amount, which can be done by a clinician.

Unless otherwise specified, all compounds present in the present application are intended to include all possible optical isomers, such as single chiral compounds, or mixtures of various chiral compounds (i.e., racemates). Among all compounds of the application, each chiral carbon atom can be optionally R configuration or S configuration, or a mixture of R configuration and S configuration.

As used herein, the term "compound of the application" refers to the compound of formula I. The term also includes various crystalline forms, pharmaceutically acceptable salts, hydrates or solvates of the compounds of formula I.

As used herein, the term "pharmaceutically acceptable salt" refers to a salt suitable for a medicament formed by the compound of the application with an acid or base. Pharmaceutically acceptable salts include inorganic salts and organic salts. A preferred type of salts is the salts formed by the compound of the application with acids. The acids suitable for forming the salts include but are not limited to: hydrochloric acid, hydrobromic acid, hydrofluoric acid, sulfuric acid, nitric acid, phosphoric acid and the like inorganic acids; formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid and the like organic acids; and aspartic acid, glutamic acid and the like acidic amino acids.

As used herein, the term "pharmaceutically acceptable salt" refers to a salt formed by a compound of the invention with an acid or base suitable for use as a drug. Pharmaceutically acceptable salts include inorganic salts and organic salts. A preferred type of salt is the salt formed by the compound of the invention and the acid. The acids suitable for salt formation include but are not limited to: hydrochloric acid, hydrobromic acid, hydrofluoric acid, sulfuric acid, nitric acid, phosphoric acid and other inorganic acids; formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenesulfonic acid, benzenesulfonic acid and other organic acids; And aspartic acid, glutamic acid and other acidic amino acids.

The terms "treatment", "treating" and "therapy" refer to the alleviation or eradication of disease or disease-related symptom. In some embodiments, such terms refer to minimizing the spread or deterioration of a disease by administering one or more prophylactic or therapeutic agents to a patient with the disease. In the content of the present application, the terms "treatment", "treating" and "therapy" also refer to:
(i) preventing the occurrence of the disease or disorder in a mammal, particularly when the mammal tends to suffer from the disease but has not been diagnosed to have the disease;
(ii) inhibiting (the development of) the disease or disorder;
(iii) alleviating (i.e., recessing) the disease or disorder; or
(iv) alleviating the symptoms caused by the disease or disorder, i.e. alleviating the pain without solving the underlying disease or disorder.

The terms "disease" and "disorder" used herein can be used interchangeably, or be different, in which the specific disease or disorder may not have a known pathogen (so that the etiology may not be known), and thus, it has not been recognized as a disease, but as an undesired condition or syndrome, in which the clinician more or less identifies a specific set of symptoms.

The terms "regulation" and "regulating" refer to the ability of a compound increasing or decreasing, for example, the function or activity of MAP kinase interacting-kinase (MNK) "Regulation" and its various forms are intended to include inhibition, antagonism, partial antagonism, activation and/or partial activation of MNK related activities. MNK inhibitors are compounds that bind to, partially or completely block stimulation, reduce, prevent, delay activation, inactivate, reduce sensitivity or down regulate signal transduction. The ability of compounds to regulate MNK activity can be confirmed by enzyme assay or cell based assay.

"Patients" or "objects" include animals, such as human, cow, horse, sheep, lamb, pig, chicken, turkey, quail, cat, dog, mouse, rat, rabbit or guinea pig. The animals can be mammals, such as non-primates and primates (for example, monkey and human). In one embodiment, the patient is a human, for example, a human infant, child, adolescent or adult.

The term "prodrug" refers to the precursor of a drug, which is a compound that must undergo chemical transformation through the metabolic process after being given to a patient and then become an active pharmacology substance. The exemplary prodrug of the compound formula I is ester, acetamide, and amide.

The term "tautomer" refers to the proton transfer from one atom of a molecule to another atom of the same molecule. For example, when W1 and W2 are oxo substituents and $R^1$ is H, the application provides a tautomer of the compound of formula I as follows:

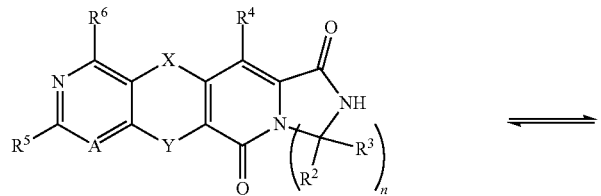

Compound of Formula I and Preparation Thereof

The application provides a compound of formula (I):

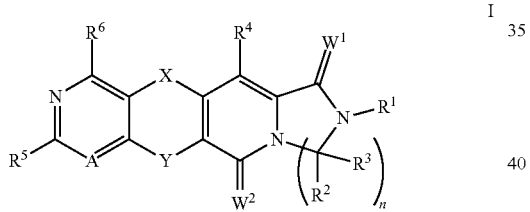

or a stereoisomer, tautomer, prodrug, solvate, hydrate, stable isotope derivative or pharmaceutically acceptable salt thereof, wherein:

A is —N— or —$CR^7$—;

X is —$(CR^{1a}R^{1b})_p$-M-$(CR^{2a}R^{2b})_q$—, wherein M is a chemical bond or selected from the group consisting of —N($R^9$)—, —O—, —S—, —C(O)—, —S=O, —S(O)$_2$—, —C(O)NH—, —C(=CH$_2$)—, or —NHC(O)—;

p and q are each independently 0, 1 or 2;

Y is selected from the group consisting of —N($R^8$)—, —O—, —S—, —C(O)—, —S=O, —S(O)$_2$—, or —CHR$^9$—;

$W^1$ and $W^2$ are independently selected from the group consisting of O, S or N—OR', wherein R' is hydrogen or C1-C8 alkyl;

$R^1$ is selected from the group consisting of hydrogen, —OH, acetyl, C1-C8 alkyl, —C(O)(C1-C8 alkyl), —C(O)(C3-C8 cycloalkyl), —COOH, —C(O)O—(C1-C8)alkyl, C3-C8 cycloalkyl, 5-12 membered aryl, 5-12 membered heteroaryl, or 5-12 membered heterocyclyl;

n is 1, 2 or 3;

$R^2$ and $R^3$ are each independently selected from the group consisting of hydrogen, C1-C8 alkyl, C2-C8 alkenyl, C2-C8 alkynyl, C6-C10 aryl, 5-12 membered heteroaryl, C1-C4 alkylene-(5-12) membered heteroaryl, C3-C8 cycloalkyl, C1-C4 alkylene-(C3-C8)cycloalkyl, 5-12 membered heterocyclyl, C1-C4 alkylene-(5-12) membered heterocyclyl; or $R^2$ and $R^3$ together with the carbon atom connected thereto form the radicals selected from the group consisting of: C3-C10 monocyclic alkyl, C3-C10 bicyclic or polycyclic alkyl, 5-12 membered heteromonocyclic alkyl containing 1-3 N, O or S atoms, 5-12 membered heterobicyclic or heteropolycyclic alkyl containing 1-3 N, O or S atoms; the substituted monocyclic alkyl, bicyclic or polycyclic alkyl, or the substituted heteromonocyclic alkyl, substituted heterobicyclic or heteropolycyclic alkyl contain 1-3 unsaturated double bonds or triple bonds; the substituted monocyclic alkyl, substituted bicyclic or

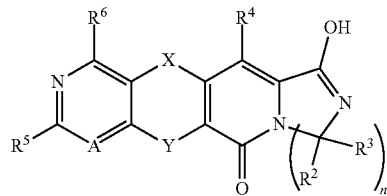

polycyclic alkyl, or the substituted heteromonocyclic alkyl, substituted heterobicyclic or heteropolycyclic alkyl are substituted at any position by one or more radicals selected from the group consisting of: deuterium, halogen, hydroxy, alkyl, heterocyclic alkyl, cycloalkyl, alkoxy, amino, aryl, heteroaryl, —$SR^{3a}$, —N($R^{3b}$)$_2$, —S(O)$_2$N($R^{3b}$)$_2$, —$NR^{3b}$C(O)N($R^{3b}$)$_2$, —$NR^{3b}$C(O)$R^{3a}$, —C(O)$R^{3a}$, —S(O)$_{0-2}R^{3a}$, —C(O)OR$_{3b}$, —(CH$_2$)$_u$OH or —(CH$_2$)$_u$N($R^{3b}$)$_2$;

$R^{1a}$, $R^{1b}$, $R^{2a}$ and $R^{2b}$ are each independently selected from the group consisting of hydrogen, deuterium, halogen, hydroxy, —SH, hydroxy-(C1-C4)alkylene, cyano, C1-C4 alkyl, C1-C4 alkoxy;

$R^{3a}$ and $R^{3b}$ are each independently selected from the group consisting of hydrogen, alkyl, haloalkyl, cycloalkyl, heterocyclic alkyl, aryl, heteroaryl, (heterocyclic alkyl)alkyl, (cycloalkyl)alkyl, arylalkyl, or arylalkyl, or two $R^b$ together with the N atom connected thereto form 3-8 membered heteromonocyclic alkyl;

$R^4$ is independently selected from the group consisting of hydrogen, halogen, hydroxy, —SH, hydroxy-(C1-C4) alkylene, cyano, C1-C4 alkyl, C1-C4 haloalkyl, C1-C4 alkoxy, C1-C4 haloalkoxy, —C(O)(C1-C8 alkyl), —C(O)(C3-C8 cycloalkyl), —COOH, —C(O)O—(C1-C8)alkyl, —S(C1-C8 alkyl), C2-C8 alkenyl, C2-C8 alkynyl, C3-C8 cycloalkyl, C6-C10 aryl, 5-12 membered heteroaryl or 5-12 membered heterocyclyl;

$R^5$, $R^6$ and $R^7$ are each independently selected from the group consisting of —H, —OH, —CN, —SR$^{10}$, halogen, —S(O)$_2$(C1-C8)alkyl, —NH—S(O)$_2$(C1-C8)alkyl, —C(O)N(R$^{10}$)$_2$, —NHC(O)R$^{10}$, —N(R$^{10}$)$_2$, —(C1-C4 alkylene)N(R$^{10}$)$_2$, C1-C8 alkyl, C2-C8 alkenyl, C2-C8 alkynyl, C1-C8 haloalkyl, —O(C1-C8 alkyl), —O(C1-C8 haloalkyl), —O(C1-C8 alkylene)NHR$^{10}$, —O(C1-C8 alkylene)N(R$^{10}$)$_2$, C6-C10 aryl, 5-12 membered heteroaryl, C1-C4 alkylene-(5-12) membered heteroaryl, C3-C8 monocyclic alkyl, C3-C10 bicyclic or polycyclic alkyl, C1-C4 alkylene-(C3-C8)cycloalkyl, 5-12 membered heterocyclyl, C1-C4 alkylene-(5-12) membered heterocyclyl; or $R^5$ and $R^7$ together with the carbon atom connected thereto form C6-C10 aryl, 5-12 membered heteroaryl, C3-C8 cycloalkyl, 5-12 membered heterocyclyl;

$R^{10}$ is selected from the group consisting of —H, —OH, —C(O)O(C1-C8 alkyl), —C(O)(C1-C8 alkyl), —C(O)—NH$_2$, —C(O)—NH(C1-C8 alkyl), —NH—(C1-C8 alkyl), —NH—C(O)(C1-C8 alkyl), NH$_2$—C(O)—(C1-C4 alkylene), —S(C1-C8 alkyl), acetyl, C1-C8 alkyl, C2-C8 alkenyl, C2-C8 alkynyl, —O(C1-C8 alkyl), —(C1-C8 haloalkyl), C1-C8 alkylamino, —C(O)(C1-C8 alkyl), —C(O)(C3-C8 cycloalkyl), —C(O)O—(C1-C8 alkyl), C3-C8 cycloalkyl, C6-C10 aryl, 5-12 membered heteroaryl or 5-12 membered heterocyclyl;

wherein, each of alkyl, alkylene, cycloalkyl, aryl, heteroaryl, heterocyclyl, amino are optionally substituted with 1, 2 or 3 J groups, the J group is selected from the group consisting of —SR$^9$, —S(O)R$^9$, —S(O)$_2$R$^9$, —S(O)N(R$^9$)$_2$, —N(R$^9$)$_2$, —C(O)OR$^9$, —C(O)R$^9$, —C(O)—N(R$^9$)$_2$, hydroxy, cyano, halogen, acetyl, C1-C4 alkyl, C2-C4 alkenyl, C2-C4 alkynyl, C1-C4 alkoxy, haloalkyl, —S—(C1-C4 alkyl), cyano-(C1-C4 alkylene), C1-C4 alkylamino, NH$_2$—C(O)—(C1-C4) alkylene, N(R$^9$)$_2$—C(O)—(C1-C4)alkylene, —CHR$^9$—C(O)—(C1-C4)alkyl, —C(O)—(C1-C4)alkyl, 5-12 membered heterocyclyl, C1-C4 alkylene-(5-12) membered heterocyclyl, C3-C8 cycloalkyl, C1-C4 alkylene-(C3-C8)cycloalkyl, C2-C4 alkylene-(C3-C8) cycloalkyl, —CHR$^9$—C(O)—(C3-C8)cycloalkyl, —C(O)—(C3-C8)cycloalkyl, —CHR$^9$—C(O)—(C6-C10)aryl, —CHR$^9$—(C6-C10)aryl, —C(O)—(C6-C10)aryl, —CHR$^9$—C(O)-(5-12) membered heterocyclyl, —C(O)-(5-12) membered heterocyclyl; or two J groups connected to the same atom form oxo (=O); and $R^8$ and $R^9$ are hydrogen, C1-C4 alkyl, hydroxy-(C1-C4) alkyl, C3-C8 cycloalkyl, 5-12 membered heterocyclyl, —NH$_2$ or —OH.

In one embodiment, the compound has the structure as shown in formula IIa or IIb:

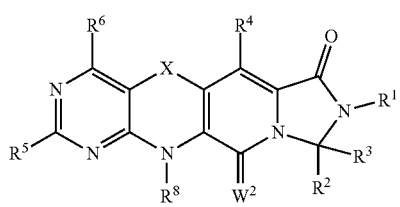

IIa

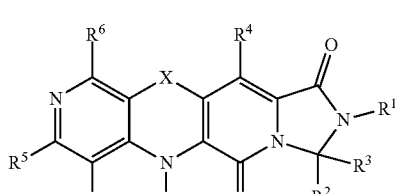

IIb

In another preferred example, X is selected from the group consisting of: —CH$_2$—, CD$_2$, —CH(OH)—, —C(=CH$_2$)—, —C(O)— or —CF$_2$—.

In one embodiment, the compound has the structure as shown in formula IIIa or IIIb:

when "Y" is —CHR$^9$— in formula IIIa or IIIb, the substituent R$^9$ is hydrogen, lower alkyl, amino or hydroxy.

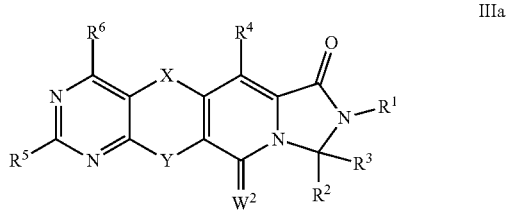

IIIa

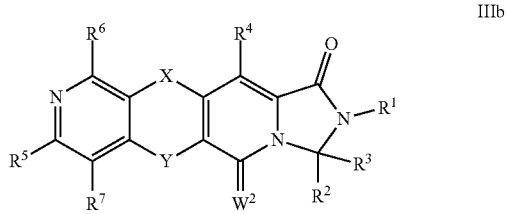

IIIb

In another preferred example, Y is selected from the group consisting of: —O—, —S—, —C(O)—, —S=O, —S(O)$_2$—, or —CHR$^9$—.

In one embodiment, in formula IIIa or IIIb, X is preferably selected from the group consisting of —(CR$^{1a}$R$^{1b}$)—, —C(O)—, N(R$^8$)—, —O—, —S—, —S=O, —S(O)$_2$—, —C(O)NH—, or —NHC(O)—; more preferably, X is selected from the group consisting of: —CH$_2$—, CD$_2$, —CH(OH)—, —C(O)— or —CF$_2$—.

In another embodiment of the application, the compound has the structure as shown in formula IVa or formula IVa:

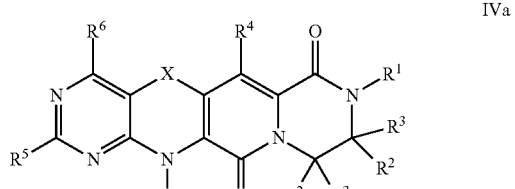

IVa

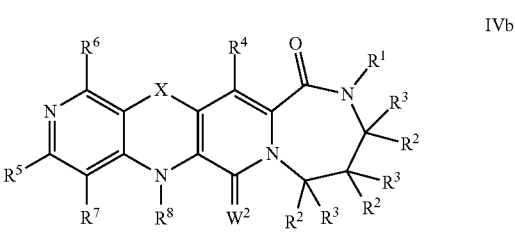

IVb

In another embodiment of the application, the compound has the structure as shown in formula Va or formula Va:

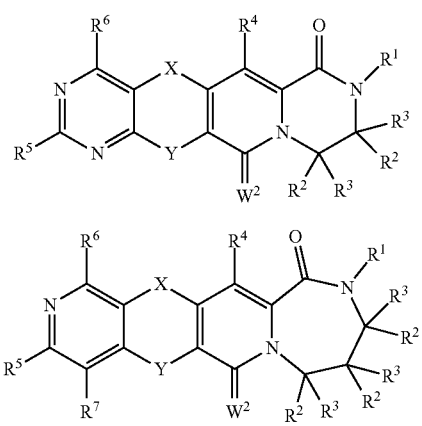

Va

Vb

In another preferred example, each of $R^2$ and $R^3$ in formula IIa, IIb, IIIa, IIIb, IVa, IVb, Va and Vb are hydrogen. Alternatively, one of $R^2$ or $R^3$ groups in formula IIa, IIb, IIIa, IIIb, IVa, IVb, Va and Vb is hydrogen, and the other group is a substituted or unsubstituted C1-C8 alkyl (i.e. substituted with 1, 2 or 3 J substituents).

In another preferred example, $R^2$ is unsubstituted alkyl, and $R^3$ is alkyl substituted with 1, 2 or 3 J groups.

In another preferred example, the compound has the structure as shown in the formula VIa or VIb, wherein A is C3-C8 cycloalkyl or 5-12 membered heterocyclyl group; moreover, the cycloalkyl or heterocyclyl ring "A" may be optionally substituted with 1, 2 or 3 J groups:

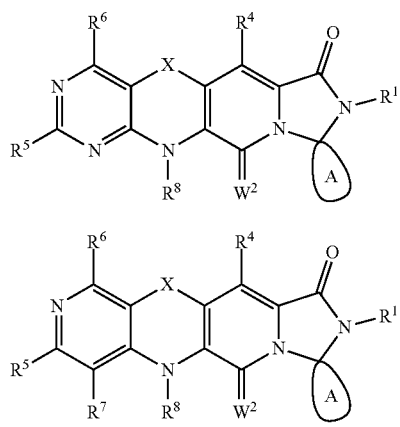

VIa

VIb

In one embodiment, in formula VIa or VIb, X is preferably selected from the group consisting of —CHR⁹—, —CR⁹R⁹—, —C(O)—, —N(R⁸)—, —O—, —S—, —S═O, —S(O)₂—, —C(O)NH—, or —NHC(O)—; substituent $R^9$ is preferably selected from the group consisting of hydrogen, deuterium, halogen, lower alkyl, amino or hydroxy; $R^8$ is preferably selected from the group consisting of hydrogen, lower alkyl, amino or hydroxy. X is more preferably selected from the group consisting of —CH₂—, CD₂, —CH(OH)—, —C(O)— or —CF₂—.

In another preferred example, the compound has the structure as shown in the formula VIIa or VIIb, wherein A is C3-C8 cycloalkyl or 5-12 membered heterocyclyl group; moreover, the cycloalkyl or heterocyclyl ring "A" may be optionally substituted with 1, 2 or 3 J groups:

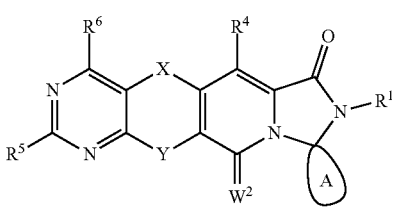

VIIa

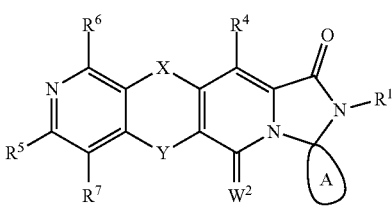

VIIb

In a preferred embodiment, when A is a fused ring, the J group is selected from the group consisting of: halogen, amino, C1-C4 alkyl amino and C1-C4 alkyl.

In another preferred example, ring A of formula VIa, VIb, VIIa, or VIIb is a heterocyclyl group, such as pyrrolidinyl, piperidinyl, tetrahydropyranyl, thietanyl, or azetidinyl.

In another preferred example, ring A is substituted with J group selected from the group consisting of: halogen, cyano, hydroxy, trifluoromethyl, N-methylamino, methyl, difluoroethenyl, and methylenenitrile.

In another preferred example, the compound has the structure as shown in formula VIII, wherein B is 5-12 membered heterocyclyl, and may be optionally substituted with 1, 2 or 3 J groups:

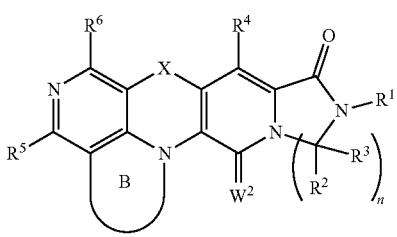

VIII

In another preferred example, the compound has the structure as shown in formula IXa, wherein C is C3-C8 cycloalkyl, 5-12 membered aryl, 5-12 membered heteroaryl or 5-12 membered heterocyclyl, and may be optionally substituted with 1, 2 or 3 J groups:

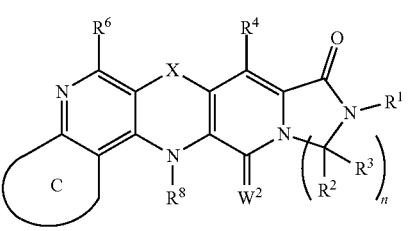

IXa

In another preferred example, the compound has the structure as shown in formula IXb, wherein C is C3-C8 cycloalkyl, 5-12 membered aryl, 5-12 membered heteroaryl or 5-12 membered heterocyclyl, and may be optionally substituted with 1, 2 or 3 J groups:

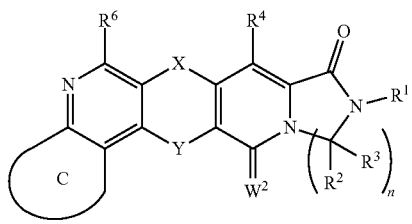

IXb

In a preferred embodiment of the application, $W^2$ is oxo group.

In another preferred example, $R^1$ is selected from the group consisting of: hydrogen, methyl, ethyl, propyl, butyl, isopropyl, sec-butyl, or tert-butyl.

The compound of the application may also include isotope markers, for example, one or more atoms in the compound are substituted with atoms having different atomic masses or atomic mass numbers, including isotopes of hydrogen, carbon, nitrogen, oxygen, phosphorus, fluorine, chlorine or iodine.

Preparation of Compound of Formula I

The compound of the application is synthesized through traditional synthesis methods, and more specifically, through the general methods as described below. A specific synthesis scheme for the compound of the present application is described in the following examples.

General Synthesis Methods

Method 1

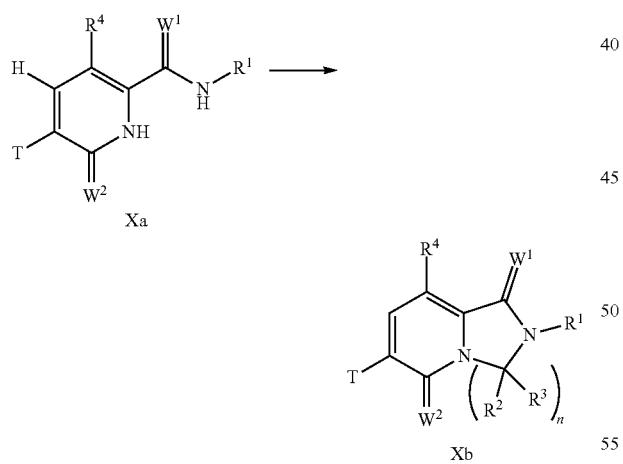

Xb (when n=1 and X=halogen or other leaving group, such as —OTf, —OTs or —OMs) is obtained by reacting an intermediate Xa with an aldehyde or a ketone equivalent Xc-f under acidic condition, wherein $R^2$ and $R^3$ are defined as above, and $R^m$ is H, $CH_3$, $CH_2CH_3$ or alkyl, and more specifically, under heating condition, Xa (where T is Cl or Br) is added to a solvent (e.g. 1,4-dioxane) containing an aldehyde or a ketone equivalent Xc-f and an acid (e.g. concentrated sulfuric acid or hydrochloric acid) to produce intermediate Xb (n=1).

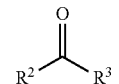 Xc

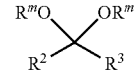 Xd

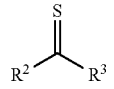 Xe

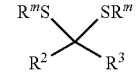 Xf

Compounds of formula XIIa or XIIb (wherein Y is $N(R^8)$, O or S and P is a protecting group) can be obtained from XI through a variety of methods, for example, by replacing the leaving group U of compound XI with a suitable N, O or S nucleophile. The obtained compound XIIb can be deprotected to produce XIIa.

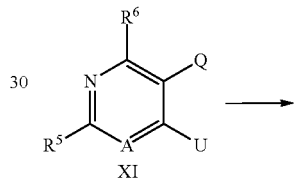

XI

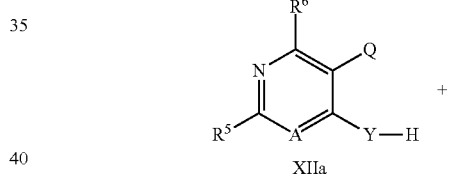

XIIa

XIIb

When Y is $NR^8$ in formula XIII, compound XIIa (Q is a precursor group of X in formula I, such as ester, alkylene ester, —O—P, —S—P, etc., P is an optional protecting group) and compound Xb (T is a leaving group, such as halogen, —OTf, —OTs or —OMs) are reacted under Buchwald-Hartwig condition (such as palladium catalyst, ligand, base, solvent and heat) to give compound XIII.

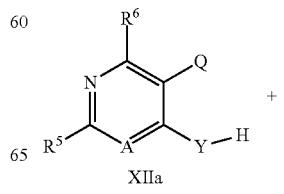

XIIa

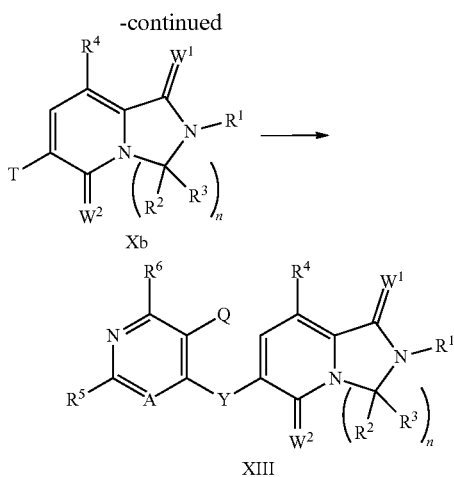

Xb

XIII

Alternatively, XIII (Y is —NR$^8$, —O—) is formed by reacting compound XIIa and compound XB (T is a leaving group, such as halogen, —OTf, —OTs or —OMs) under copper mediated Ullmann type condition (such as copper iodide (I), alkali, solvent and heat).

I (Q is ester group) is formed by the following process: compound XIII forms an acid intermediate under alkali condition; the acid intermediate undergoes heating treatment under the optional conditions including polyphosphoric acid, trifluoromethanesulfonic acid-polyphosphoric acid, POCl$_3$ and AlCl$_3$, and an additional reaction when necessary (such as reduction or deprotection, etc.) to give Compound I.

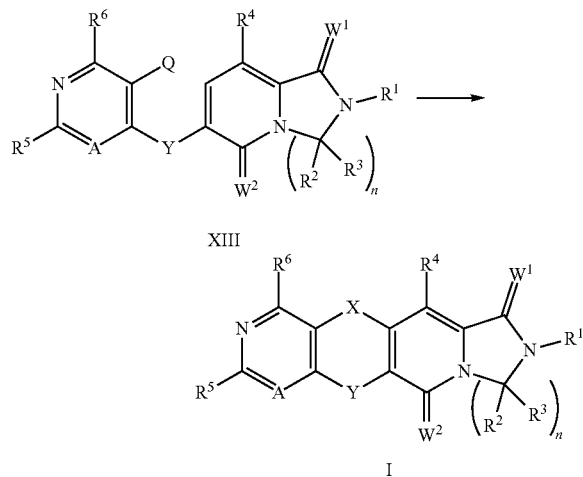

XIII

I

Pharmaceutical Preparation and Therapeutic Application

A therapeutically effective amount of a compound of the application or a pharmaceutically acceptable salt thereof is administrated, and the therapeutically effective amount varies depending on a variety of factors, including the activity of the specific compound used, the metabolic stability and duration of action of the compound, the age, weight, general health status, gender, diet of the patient, mode and time of administration, excretion rate, combination of medication, the severity of a specific disease or disorder, and the subject of treatment.

"Effective amount" or "therapeutically effective amount" means an amount of a compound of the present application (when given to a mammal, preferably a human) sufficient to provide effective treatment for a MNK related disorder or disease in the mammal (preferably human), as described below. The amount of the compound of the present application constituting the "therapeutically effective amount" may vary depending on the compound, the disease and its severity, the mode of administration, and the age of the mammal to be treated, but it can be routinely determined by those skilled in the art according to their knowledge and the content of the present application.

The compound of the application, or the pharmaceutically acceptable salt thereof, can also be administrated before, at the same time or after the administration of one or more other therapeutic agents. Such combination therapy includes administration of a single dose formulation comprising the compound of the application and one or more other active substances, or administration of the compound of the application and each active substance in separated drug dose formulations. For example, the compound of the application and other active substances may be administered to a patient together in a single oral dose composition, such as a tablet or capsule, or the substances may be administered in separated oral dose formulations. When using a separated dose formulations, the compound of the application and one or more other active agents can be administered substantially at the same time (i.e., simultaneously), or at separated staggered time (i.e., sequentially); it should be understood that combination therapy includes all of these options.

In some embodiments, the compounds disclosed herein are useful for inhibiting MNK activity and/or for analyzing MNK signal transduction activity in a model system, and/or for preventing, treating or alleviating symptoms associated with diseases, disorders or pathological conditions involving MNK, preferably those causing suffering in human. Compounds capable of inhibiting MNK activity may be used to prevent, treat, alleviate or reduce symptoms or disease progression in the following events: uncontrolled cell growth, proliferation and/or survival, improper cellular immune response, or improper cellular inflammatory response, or diseases accompanied by uncontrolled cell growth, proliferation and/or survival, improper cellular immune response, or improper cellular inflammatory response, especially in which the uncontrolled cell growth, proliferation and/or survival, improper cellular immune response, or improper cellular inflammatory response is mediated by MNK, such as hematological tumor, solid tumor and/or its metastasis, including leukemia and myelodysplastic syndrome, Waldenstrom's macroglobulinemia and malignant lymphoma, such as B-cell lymphoma, T-cell lymphoma, hairy cell lymphoma, Hodgkin's lymphoma, non-Hodgkin's lymphoma and Burkitts's lymphoma, head and neck tumor, including brain tumor and brain metastasis, chest tumor, including non-small cell and small cell lung tumor, gastrointestinal tumor, endocrine tumor, breast and other gynecological tumors, urinary system tumors, including renal, bladder and prostate tumors, skin tumors, and sarcomas, and/or their metastases.

In addition, compounds and pharmaceutical compositions thereof of the application are candidate therapeutic agents for the prevention and/or treatment of cytokine related diseases, such as inflammatory diseases, allergies, or other diseases associated with pro-inflammatory cytokines. Exemplary inflammatory diseases include, but not limited to, chronic or acute inflammation, arthritis, such as chronic inflammatory arthritis, rheumatoid arthritis, psoriatic arthritis, osteoarthritis, juvenile rheumatoid arthritis, Reiter's syndrome, rheumatoid arthritis, rubella arthritis, acute synovitis, and gouty arthritis; inflammatory skin diseases such as sunburn, psoriasis, erythrodermatic psoriasis, pustular psoriasis, eczema, dermatitis, acute or chronic graft formation, atopic dermatitis, contact dermatitis, urticaria and scleroderma; gastrointestinal inflammation, such as inflammatory bowel disease, Crohn's disease and related diseases, ulcerative colitis, colitis and diverticulitis; nephritis, urethritis, salpingitis, ovaritis, endometritis, spondylitis, systemic lupus erythematosus and related diseases, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory pulmonary disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondyloarthropathy, ankylosing spondylitis, synovitis, tenosynovitis, myositis, pharyngitis, rheumatic polymyalgia, shoulder tendinitis or bursitis, gout, pseudogout, vasculitis, thyroiditis selected from granulomatous thyroiditis, lymphocytic thyroiditis, infiltrative fibrous thyroiditis and acute thyroiditis; Hashimoto's thyroiditis, Kawasaki's disease, Raynaud's phenomenon, Sjogren's syndrome, neuroinflammatory diseases, sepsis, conjunctivitis, keratitis, iridocyclitis, optic neuritis, otitis, lymphadenitis, nasopharyngitis, sinusitis, pharyngitis, tonsillitis, laryngitis, epiglottitis, bronchitis, pneumonia, stomatitis, gingivitis, esophagitis, gastritis, peritonitis, hepatitis, cholelithiasis, gallbladder, glomerulonephritis, benign pneumonia, crescentic glomerulonephritis, pancreatitis, endometritis, myometritis, metritis, cervicitis, ectocervicitis, paracervicitis, tuberculosis, vaginitis, vulvitis, silicosis, sarcomatosis, pneumoconiosis, abscess, inflammatory polyarthritis, psoriatic arthritis, intestinal fibrosis, bronchiectasis and enteropathic arthritis.

Although inflammation is the unified pathogenic course of these diseases, current therapies only treat the symptoms of the diseases, not the underlying causes of inflammation.

The compositions of the present application are useful for the treatment and/or prevention of inflammatory diseases and related complications and disorders.

Accordingly, certain embodiments relate to methods for the treatment of MNK dependent disorders in a mammal in need, comprising administering an effective amount of the above pharmaceutical composition (i.e., a pharmaceutical composition comprising any one or more compounds of formula I) to the mammal.

As mentioned above, the disorder of protein synthesis is a common event in human cancer. The key regulator of translation control is eIF4E, whose activity is the key determinant of tumorigenicity. Because the activation of eIF4E involves the phosphorylation of a key serine (Ser209) specifically affected by MAP kinase interacting kinase (MNK), MNK inhibitors are suitable candidates for the treatment of proliferative diseases (e.g., cancer). The compositions and methods described herein can be used to treat a variety of cancers including solid tumors, lymphoma and leukemia. The types of cancer that can be treated include but not limited to breast, prostate and colon adenocarcinoma; all forms of lung bronchial carcinoma; bone marrow; melanoma; liver cancer; neuroblastoma; papilloma; apudomas; myxoblastoma; branching tumor; malignant carcinoid syndrome; carcinoid heart disease; and cancer (e.g., Walker, basal cell, basal squamous cell, Brown-Pearce, duct, Ehrlich tumor, Krebs 2, Merck cell, mucus, non-small cell lung, oat cell, papillary cell, scirrhus, bronchus, bronchogenic, squamous cell and transitional cell). Other types of cancer that can be treated include: histiocytic diseases; acute and chronic leukemia, bone marrow and lymphoid/lymphoblastic, including hairy cell leukemia; malignant histiocytosis; Hodgkin's disease; immunoproliferative tumor; Hodgkin's lymphoma; B-cell and T-cell non-Hodgkin's lymphoma, including diffuse large B-cell lymphoma and Burkitt's lymphoma; plasmacytoma; reticuloendothelial tissue proliferated; melanoma; multiple myeloma; chondroblastoma; chondroma; chondrosarcoma; fibroma; fibrosarcoma; bone marrow fibrosis; giant cell tumor; histiocytoma; lipoma; liposarcoma; mesothelioma; myxoma; myxosarcoma; osteoma; osteosarcoma; chordoma; craniopharyngioma; dysgerminoma; hamartoma; mesenchymal tumor; mesonephroma; myoma; ameloblastoma; cementoma; odontoma; teratoma; thymoma; trophoblastic tumor.

Other cancers that can be treated with the compound of the application include but not limited to: adenomas; cholangioma; cholesteatoma; cylindricoma; cystadenocarcinoma; cystadenoma; granulosa cell tumor; amphoteric blastoma; hepatoma; sweat gland adenocarcinoma; pancreatic islet cell carcinoma; leydig cell tumor of testis; papilloma; sertoli cell tumor of testis; membranous cell tumor; leiomyoma; leiomyosarcoma; myoblastoma; myoma; myosarcoma; rhabdomyoma; rhabdomyosarcoma; ependymoma; ganglioma; gliomas; medulloblast; meningioma; schwannoma; neuroblastoma; neuroepithelioma; neurofibroma; neuroma; paraganglioma; non-chromaffin paraganglioma.

In one embodiment, the compound of the application is a candidate therapeutic agent for the treatment of, for example, hemangioma; the proliferation of vascular lymphocytes accompanied with eosinophilia; sclerosing hemangioma; angiomatosis; glomus tumor; hemangioendothelioma; hemangioma; hemangiopericytoma; angiosarcoma; lymphangioma; lymphangiomyoma; lymphangiosarcoma; pineal gland tumor; carcinosarcoma; chondrosarcoma; cystosarcoma phyllodes; fibrosarcoma; angiosarcoma; leiomyosarcoma; white cell sarcoma; liposarcoma; lymphangiosarcoma; myosarcoma; myxosarcoma; oophoroma; rhabdomyosarcoma; sarcoma; neoplasm; neurofibromatosis; and cervical atypical hyperplasia.

In a specific embodiment, the application provides a method for treating the following diseases: colon cancer, colorectal cancer, gastric cancer, thyroid cancer, lung cancer, leukemia, pancreatic cancer, melanoma, multiple myeloma, brain cancer, primary and secondary CNS cancer, including malignant neuroglial tumor and glioblastoma, renal cancer, prostate cancer, including castration resistant prostate cancer, ovarian cancer or breast cancer, including triple negative, HER2 positive and hormone receptor positive breast cancer. According to the method, a therapeutically effective amount of at least one compound of formula I or its stereoisomer, tautomer or pharmaceutically acceptable salt can be administrated to a subject diagnosed with a proliferative disease (such as cancer). Alternatively, a pharmaceutical composition comprising at least one compound of formula I or its stereoisomer, tautomer or pharmaceutically acceptable salt can be administrated to a subject diagnosed with cancer.

In some embodiments, the compounds of the present application and other conventional cancer therapeutics, such as radiotherapy or surgery, are administered in combination to a cancer subject. Radiotherapy is well known in the art and includes X-ray therapy, such as gamma radiation, and radiopharmaceutical therapy.

In some embodiments, the MNK inhibitor compound of the application is used in combination with at least one anticancer agent. Anticancer agents include chemotherapy agents. Chemotherapeutic agents include, but not limited to, chromatin function inhibitors, topoisomerase inhibitors, microtubule inhibitors, DNA disruptors, antimetabolizers (such as folate antagonists, pyrimidine analogues, purine analogues, and sugar modified analogues), DNA synthesis inhibitors, DNA interacting agents (such as intercalators), and DNA repair inhibitors.

Exemplary chemotherapy agents include, but not limited to, the group consisting of: immune checkpoint inhibitors, such as navulizumab, pablizumab, atzumab, duvalizumab, avelumab, sindilimab, treprizumab and epizumab; antimetabolic/anticancer agents, such as pyrimidine analogues (5-fluorouracil, fluorouridine, capecitabine, gemcitabine and cytarabine) and purine analogues, folate antagonists and related inhibitors (thiopurine, thioguanine, pemistatin and 2-chlorodeoxyadenosine (cladribine)); antiproliferative/antimitotic agents, including natural products such as vinca alkaloids (vinblastine, vincristine and vinorelbine), microtubule interfering agents such as taxane (paclitaxel, docetaxel), vincristine, vinblastine, nocodazole, epothilone and vinorelbine, epipodophyllotoxin (etoposide, teniposide), DNA damaging agents (actinomycin, acridine, anisomycin, bleomycin, busulfan, camptothecin, carboplatin, chlorambucil, cisplatin, cyclophosphamide, endoxan, pleistomycin, daunorubicin, doxorubicin, epirubicin, hexamethylmelamine oxime acid, isophosphamide, melphalan, meropenem, mitomycin, mitoxantrone, nitrosourea, procalcamycin, procarbazine, paclitaxel, taxotere, temozolomide, teniposide, triethylenethiophosphamide and etoposide (VP16)); antibiotics, such as dactinomycin (actinomycin D), daunorubicin, doxorubicin (doxorubicin), idarubicin, anthracycline, mitoxantrone, bleomycin, mithramycin (mirincamycin) and mitomycin; enzymes (L-asparaginase, which metabolizes L-asparagine and deprives of cells without the ability to synthesize their own asparagine); antiplatelet agents; antiproliferative/antimitotic alkylating agents, such as nitrogen mustard (methionine mustard, cyclophosphamide and analogues, melphalan, chlorambucil), ethyleneimine and methylmelamine (hexamethylmelamine and thiotepa), alkyl sulfonate-busulfan, nitrosourea (carmustine (BCNU) and analogues, streptozotocin), DTIC; antiproliferative/antimitotic antimetabolites, e.g., folate analogues (methotrexate); platinum coordination complexes (cisplatin, carboplatin), procarbazide, hydroxyurea, mitotan, aminoglutethimide; hormones, hormone analogues (estrogen, tamoxifen, goserelin, bicalutamide, niromide) and aromatase inhibitors (letrozole, anastrozole); anticoagulants (heparin, synthetic heparin salts and other thrombin inhibitors); fibrinolytic agents (e.g. tissue plasminogen activator, streptokinase and urokinase), aspirin, dipyridamole, ticlopidine, clopidogrel, acizumab; anti-mildew agents; breveldin; immunosuppressants (cyclosporin, tacrolimus (FK-506), sirolimus (rapamycin), azathioprine, mycophenolate mofeti); anti angiogenic compounds (TNP470, genistein) and growth factor inhibitors (vascular endothelial growth factor (VEGF) inhibitors, fibroblast growth factor (FGF) inhibitors); angiotensin receptor blockers; nitrogen monoxide donor; antisense oligonucleotides; antibody (trastuzumab, rituximab); chimeric antigen receptor; cell cycle inhibitors and differentiation inducers (retinoic acid); mTOR inhibitors, topoisomerase inhibitors (doxorubicin (adriamycin), acridine, camptothecin, daunorubicin, dactinomycin, enobicin, epirubicin, etoposide, idarubicin, irinotecan (CPT-11) and prednisolone, topotecan, irinotecan); corticosteroids (cortisone, dexamethasone, hydrocortisone, methylprednisolone, prednisone and prednisolone); growth factor signal transduction kinase inhibitors; mitochondrial dysfunction inducers, toxins such as cholera toxin, ricin, pseudomonas exotoxin, Diphtheria toxin, and cystatin activators; and, chromatin destructor.

In some embodiments, the MNK inhibitors of the present application are used in the same or separated formulations, simultaneously with or sequentially with, other reagents that are part of the combination therapy regimen.

MNK inhibitors of formula I, including the corresponding salts and pharmaceutical compositions of compounds of formula I, can also effectively treat or prevent cytokine mediated diseases as therapeutic agents, such as inflammation in patients (preferably human). In one embodiment, the compounds or compositions of the application are particularly beneficial for the treatment or prevention of diseases selected from the group consisting of: chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

The compounds and the corresponding salts and pharmaceutically acceptable compositions of the application are candidate therapeutic agents for the treatment of brain related diseases, including but not limited to autism, fragile X syndrome, Parkinson's disease and Alzheimer's disease. Treatment can be achieved by administrating to a subject in need of the treatment a compound of formula I, a pharmaceutically acceptable salt thereof, or a pharmaceutically acceptable composition of a compound of formula I or a salt thereof.

In another aspect of the invention, a compound of the application or a pharmaceutically acceptable formulation of the compound of the application is provided as an inhibitor of MNK activity. The inhibition is achieved by contacting MNK-expressing cells with the compound or the pharmaceutically acceptable formulation to reduce or inhibit MNK activity, so as to provide therapeutic efficacy against MNK dependent disorders in mammals in need.

The general range of therapeutically effective amount of a compound of formula I or a composition of the compound of formula I can be: about 1-2000 mg/day, about 10-1000 mg/day, about 10-500 mg/day, about 10-250 mg/day, about 10-100 mg/day, or about 10-50 mg/day. The therapeutically effective amount can be administrated in one or more doses. However, it should be understood that the specific dose of the compound of the application for any particular patient will depend on a variety of factors, such as the age, gender, weight, general health status, diet, individual response of the patient to be treated, administration time, severity of the disease to be treated, activity, dosage form of the specific compound administered, mode of application and concomitant drug. The therapeutically effective amount in a given situation can be determined by routine experiments and within the ability and judgment of clinicians or physicians. In any case, the compound or composition can be administered in multiple doses based on the individual circumstances of the patient and in a manner that allows delivery of a therapeutically effective amount.

The invention is further described in combination with specific examples. It should be understood that these examples are intended to illustrate the invention only and are not intended to limit the scope of the invention. The following examples do not indicate the specific conditions of the experimental method, usually according to the conventional conditions, or according to the conditions recommended by the manufacturer. Percentages and portions are calculated by weight unless otherwise stated.

Synthesis

The examples provided below are only for illustration and not by way of limitation.

Example 1: Compounds 1 and 2

Synthesis of Intermediate A

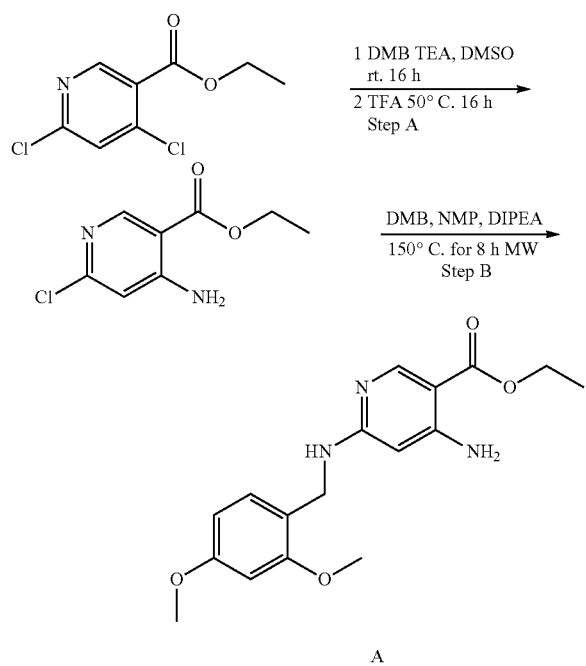

A

Step A: ethyl 4-amino-6-chloronicotinate

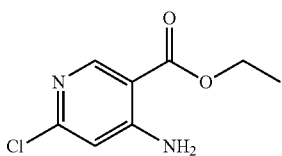

To a solution of ethyl 4,6-dichloronicotinate (60 g, 0.27 mmol) in dimethyl sulfoxide (500 ml), 2,4-dimethoxybenzylamine (47.8 g, 0.287 mmol) and triethylamine (55 g, 0.545 mmol) were added at room temperature, and the reaction mixture was stirred at room temperature overnight. Water (2 L) was added to the reaction, and the reaction mixture was extracted with ethyl acetate (2.5 L×2), washed with brine, dried over anhydrous sodium sulfate, filtered and concentrated under vacuum to give ethyl 6-chloro-4-(2,4-dimethoxybenzylamino)nicotinate. The product was dissolved in trifluoroacetic acid (300 ml), and the reaction mixture was heated and stirred at 50° C. overnight. The mixture was cooled to room temperature and concentrated to dryness. The mixture was extracted with ethyl acetate (2.5 L×2), washed with brine (500 ml), and then the organic phase was washed with saturated aqueous sodium bicarbonate solution (500 ml), dried and concentrated under vacuum. The obtained product was purified by silica gel column chromatography (petroleum/ethyl acetate=2/1) to give ethyl 4-amino-6-chloronicotinate (34 g, yield 62.3%) as a white solid.

$^1$H NMR (400 MHz, CDCl$_3$) δ 8.69 (s, 1H), 6.57 (s, 1H), 4.36 (q, J=7.1 Hz, 2H), 1.40 (t, J=7.1 Hz, 3H).

Step B: ethyl 4-amino-6-((2,4-dimethoxybenzyl)amino)nicotinate

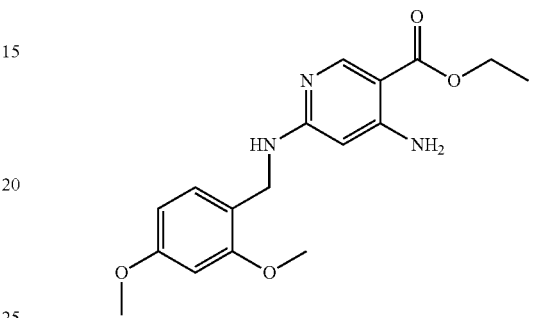

Ethyl 4-amino-6-chloronicotinate (2 g, 0.01 mmol) was dissolved in N-methylpyrrolidone (7.5 ml) at room temperature, followed by successive addition of 2,4-dimethoxybenzylamine (2.5 g, 0.015 mmol) and N,N-diisopropylethylamine (3.87 g, 0.03 mmol). Under the protection of nitrogen at room temperature, the reaction mixture was heated in a microwave at 150° C. for 8 h. The mixture was cooled to room temperature, added with water (50 ml), and extracted with ethyl acetate (200 ml). The organic phase was washed with brine, dried over anhydrous sodium sulfate and concentrated under vacuum. The obtained product was purified by silica gel column chromatography (petroleum/ethyl acetate=2/1) to give the desired compound (1.5 g, yield 45.4%) as a yellow solid.

$^1$H NMR (400 MHz, DMSO) δ 8.34 (s, 1H), 7.04 (d, J=8.3 Hz, 1H), 6.91 (t, J=6.1 Hz, 1H), 6.77 (s, 2H), 6.54 (d, J=2.3 Hz, 1H), 6.45 (dd, J=8.3, 2.4 Hz, 1H), 5.56 (s, 1H), 4.26 (d, J=5.9 Hz, 2H), 4.18 (q, J=7.1 Hz, 2H), 3.80 (s, 3H), 3.73 (s, 3H), 1.26 (t, J=7.1 Hz, 3H).

Synthesis of Intermediate B

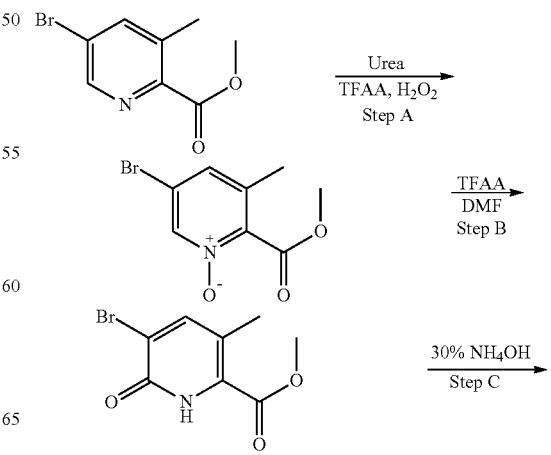

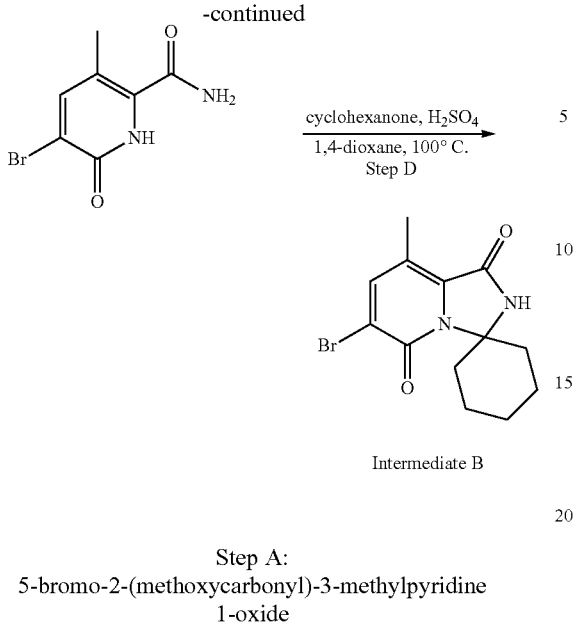

Intermediate B

Step A:
5-bromo-2-(methoxycarbonyl)-3-methylpyridine 1-oxide

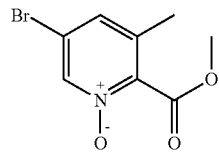

Methyl 5-bromo-3-methylpyridineformate (4.0 g, 17.4 mmol) was dissolved in 100 ml of dichloromethane. The reaction solution was cooled to 0° C., followed by addition of urea peroxide (4.91 g, 52.2 mmol), and then addition of trifluoroacetic anhydride (10.96 g, 52.2 mmol) dropwise at 0° C. The reaction solution was stirred at room temperature overnight, poured into ice water, and adjusted to a pH value of 7 with a saturated solution of dipotassium hydrogen phosphate. The mixture was extracted twice with dichloromethane (100 ml), and the organic phase was dried over anhydrous sodium sulfate, filtered, and concentrated to give the product (4.0 g, yield 93.4%).

LC-MS (ESI$^+$): m/z 246.24 248.24 (M+H)$^+$.

Step B: methyl 5-bromo-3-methyl-6-oxo-1,6-dihydropyridin-2-formate

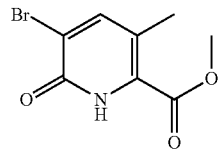

To a stirred solution of 5-bromo-2-(methoxycarbonyl)-3-methylpyridine 1-oxide (3.6 g, 14.6 mmol) in dimethylformamide (100 ml), trifluoroacetic anhydride (30.7 g, 146 mmol) was added dropwise at 0° C. The reaction mixture was warmed to 50° C., and stirred for another 3 hours. After the oxidation was completed, the reaction solution was cooled to room temperature, quenched with a saturated sodium bicarbonate solution, and extracted with dichloromethane (100 ml×2). The organic layers were separated, combined, dried over magnesium sulfate, and concentrated to the desired compound (1.21 g, yield 33.3%) as a white solid.

LC-MS (ESI$^+$): m/z 246.24 (M+H)$^+$.

$^1$H NMR (400 MHz, DMSO-d$_6$): δ 11.87 (s, 1H), 8.01 (s, 1H), 3.83 (s, 3H), 2.29 (s, 3H).

Step C: 5-bromo-3-methyl-6-oxo-1,6-dihydropyridin-2-formamide

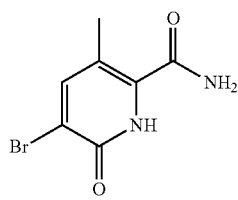

To a stirred solution of methyl 5-bromo-3-methyl-6-oxo-1,6-dihydropyridin-2-formate (2.7 g, 10.98 mmol) in methanol (10 ml), ammonia water (100 ml) was added in a 250 ml sealed tube. The reaction flask was sealed, and the reaction mixture was stirred and heated at 63° C. for 5 hours. TLC (petroleum ether/ethyl acetate=2/1, silica gel plate) showed that the raw materials had been completely consumed. The reaction mixture was concentrated under vacuum. The residue was purified by silica gel column chromatography and eluted with petroleum ether/ethyl acetate=1/1 to give the desired compound (2.1 g, yield 83.2%) as a white solid.

LC-MS (ESI$^+$): m/z 231.3, 233.23 (M+H)$^+$.

$^1$H NMR (400 MHz, DMSO-d$_6$): δ 11.87 (s, 1H), 7.88 (s, 2H), 7.77 (s, 1H), 2.15 (s, 3H).

Step D: 6'-bromo-8'-methyl-2'H-spiro[cyclohexane-1,3'-imidazo[1,5-a]pyridine]-1',5'-dione (Intermediate B)

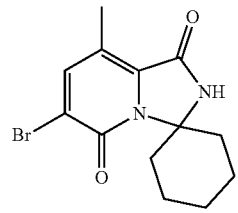 [SMILES: Cc1cc(Br)c(=O)n2c1C(=O)NC21CCCCC1]

To a solution of 5-bromo-3-methyl-6-oxo-1,6-dihydropyridin-2-foramide (2.1 g, 9.13 mmol) in 1,4-dioxane (50 ml), cyclohexanone (8.95 g, 91.3 mmol) and concentrated sulfuric acid (89.5 mg, 0.913 mmol) were added at room temperature, and the reaction mixture was heated at 100° C. for 8 h. TLC (petroleum ether/ethyl acetate=2/1) silica gel plate showed that the raw materials had been completely consumed. The reaction mixture was concentrated under reduced pressure, and the residue was purified by silica gel column chromatography and eluted with petroleum ether/ethyl acetate=1/1 to give the desired intermediate B (1.7 g, yield 60.1%) as a white solid.

LC-MS (ESI$^+$): m/z 311.3 313.3 (M+H)$^+$.

¹H NMR (400 MHz, DMSO-d₆): δ 10.38 (s, 1H), 8.02 (s, 1H), 2.91 (td, J=13.4, 4.3 Hz, 2H), 2.38 (s, 3H), 1.65 (dt, J=27.4, 13.1 Hz, 5H), 1.43 (d, J=12.0 Hz, 2H), 1.28-1.15 (m, 1H).

Synthesis of Compounds 1 and 2

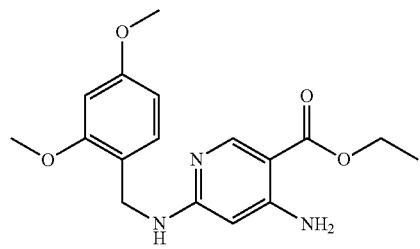

Intermediate A

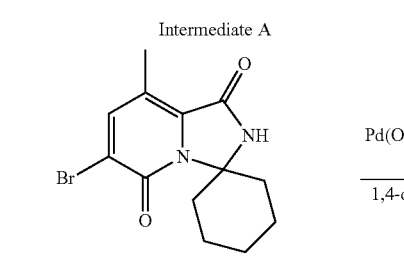

Intermediate B

Pd(OAc)₂, xantphos, Cs₂CO₃
1,4-dioxane, 95° C.,
Step A

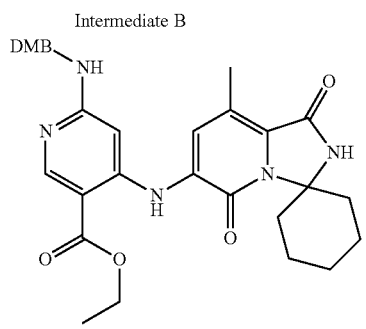

LiOH
Step B

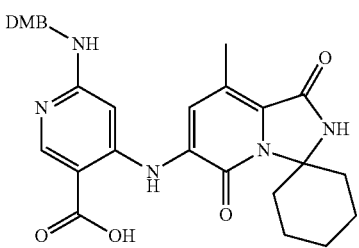

PPA
Step C

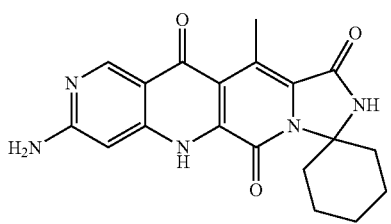

1

BH₃
THF
Step D

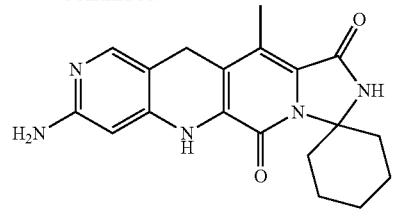

2

Step A: ethyl 6-((3,4-dimethylbenzyl)amino)-4-((8'-methyl-1',5'-dioxo-1',5'-dihydro-2'H-spiro[cyclohexane-1,3'-imidazo[1,5-a]pyridine]-6'-yl)amino)nicotinate

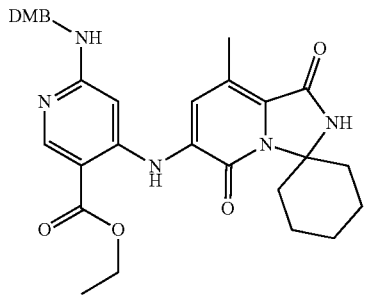

To a solution of 6'-bromo-8'-methyl-2'H-spiro[cyclohexane-1,3'-imidazo[1,5-a]pyridine]-1',5'-dione (1.32 g, 4.26 mmol) in 1,4-dioxane (70 ml), ethyl 4-amino-6-((2,4-dimethoxybenzyl)amino)nicotinate (1.69 g, 5.11 mmol), Pd₂(dba)₃ (585.3 mg, 0.639 mmol), x-phos (305 mg, 0.639 mmol), cesium carbonate (4.19 g, 12.8 mmol) were added at room temperature under the protection of nitrogen. The reaction solution was heated at 105° C. for 12 hours under the protection of nitrogen. TLC (petroleum ether/ethyl acetate=2/1, silica gel plate) indicated that the raw materials had been completely consumed. The mixture was cooled to room temperature, and extracted with ethyl acetate (150 ml×2). The organic layers were combined, washed with brine (50 ml×3), dried over anhydrous sodium sulfate, filtered and concentrated under vacuum. The product was purified with a chromatographic column (petroleum ether/ethyl acetate=1/1) to give the desired compound (850.0 mg, yield 35.6%) as a yellow solid.

LC-MS (ESI+): m/z 562.3 (M+H)+.

Step B: 64(3,4-dimethylbenzyl)amino)-4-((8'-methyl-1',5'-dioxo-1',5'-dihydro-2'H-spiro[cyclohexane-1,3'-imidazo[1,5-a]pyridine]-6'-yl)amino) nicotinic acid

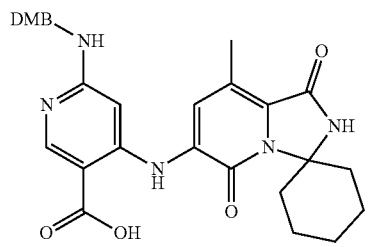

Ethyl 6-((2,4-dimethoxybenzyl)amino)-4-((8'-methyl-1',5'-dioxo-1',5'-dihydro-2'H-spiro[cyclohexane-1,3'-imidazo[1,5-a]pyridine]-6'-yl)amino)nicotinate (850 mg, 1.52 mmol) was dissolved in a mixed solution of tetrahydrofuran (200 ml) and methanol (100 ml), followed by addition of lithium hydroxide (191 mg, 4.55 mmol) and deionized water (2 ml). The reaction was heated at 40° C. for 12 hours. TLC (dichloromethane/methanol=10/1, silica gel plate) indicated that the raw materials had been completely consumed. The mixture was cooled to room temperature, and the residue was washed with diethyl ether (50 ml). The aqueous layer was acidified to pH=6 with 1M aqueous hydrochloric acid solution. The mixture was extracted with ethyl acetate (100 ml×2). The combined organic layers were washed with brine (50 ml×3), dried over anhydrous sodium sulfate, filtered and concentrated under vacuum to give the target compound (780 mg, crude) as a gray solid.

LC-MS (ESI+): m/z 534.3 (M+H)+.

Step C: 8'-amino-12'-methyl-2'H-spiro[cyclohexane-1,3'-imidazo[1',5':1,6]pyrido[3,4-b][1,6]naphthyridine]-1',5',11'(6'H)-trione (Compound 1)

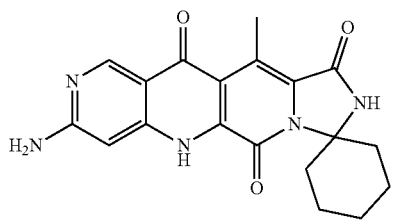 [SMILES: Cc1c2n(c(=O)c3[nH]c4cc(N)ncc4c(=O)c13)C1(CCCCC1)NC2=O]

A mixture of 64(3,4-dimethylbenzyl)amino)-4-((8'-methyl-1',5'-dioxo-1',5'-dihydro-2'H-spiro[cyclohexane-1,3'-imidazo[1,5-a]pyridine]-6'-yl)amino)nicotinic acid (700 mg, 1.313 mmol, crude) and polyphosphoric acid (10 g) was heated at 130° C. for 12 hours. TLC (dichloromethane/methanol=10/1, silica gel plate) indicated that the raw materials had been completely consumed. The mixture was cooled to room temperature and then poured into ice water. The aqueous layer was first washed with diethyl ether (50 ml), basified to pH=7.5 with 1M sodium hydroxide, and extracted with ethyl acetate (150 ml×2). The combined organic layers were washed with brine (50 ml×3), dried over anhydrous sodium sulfate, filtered, and concentrated under vacuum to give target compound 1 (291 mg, 61.7%) as a yellow solid.

LC-MS (ESI+): m/z 366.2 (M+H)+.

1H NMR (400 MHz, DMSO-d6) M1.42 (s, 1H), 10.08 (s, 1H), 8.73 (s, 1H), 6.64 (s, 2H), 6.55 (s, 1H), 2.90 (s, 3H), 1.93 (dd, J=24.7, 12.4 Hz, 1H), 1.80-1.53 (m, 6H), 1.44 (d, J=12.4 Hz, 3H).

Step D: 8'-amino-12'-methyl-6',11'-dihydro-2'H-spiro[cyclohexane-1,3'-imidazole[1',5':1,6]pyrido[3,4-B][1,6]naphthyridine]-1',5'-dione hydrochloride (Compound 2)

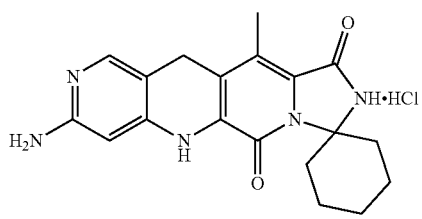

In a 250 ml sealed tube, zinc powder (448.1 mg, 6.85 mmol) was added to a mixed solution of 8'-amino-12'-methyl-2'H-spiro[cyclohexane-1,3'-imidazo[1',5':1,6]pyrido[3,4-b][1,6]naphthyridine]-1',5',11'(6'H)-trione (250 mg, 0.685 mmol) and NH4OH (50 ml) at room temperature. The reactants were stirred at 105° C. for 12 hours. TLC (dichloromethane/methanol=10/1, silica gel plate) indicated that the raw materials had been completely consumed. The reaction mixture was cooled to room temperature, concentrated to dryness under vacuum. The mixture was dissolved in 1 N aqueous hydrochloric acid solution (30 ml), and then extracted with a mixed solvent of dichloromethane and isopropanol (dichloromethane and isopropanol=3/1, 100 ml×5), and the organic phase was washed with brine, dry filtered and concentrated under vacuum. The obtained concentrate was purified by reverse phase column chromatography (acetonitrile/water) to give target compound 2 (108.3 mg, yield 45.04%) as a yellow solid.

LC-MS (ESI+): m/z 352.0 (M+H)+.

1H NMR (400 MHz, DMSO-d6): M2.33 (s, 1H), 10.14 (s, 1H), 9.97 (s, 1H), 7.63 (s, 1H), 7.37 (s, 2H), 6.46 (s, 1H), 3.88 (s, 2H), 3.03-2.92 (m, 2H), 2.39 (s, 3H), 1.79-1.59 (m, 5H), 1.43 (d, J=12.0 Hz, 2H), 1.27-1.14 (m, 1H).

Example 2: Synthesis of Compounds 3 and 4

Synthesis scheme

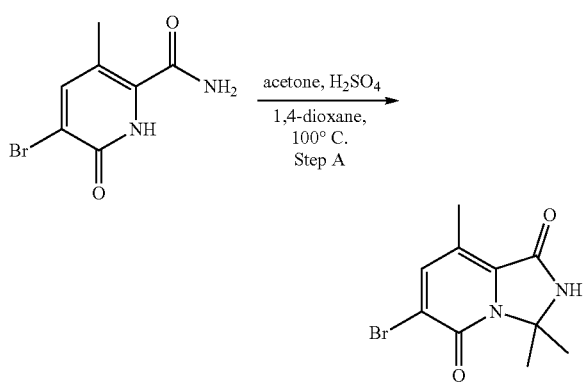

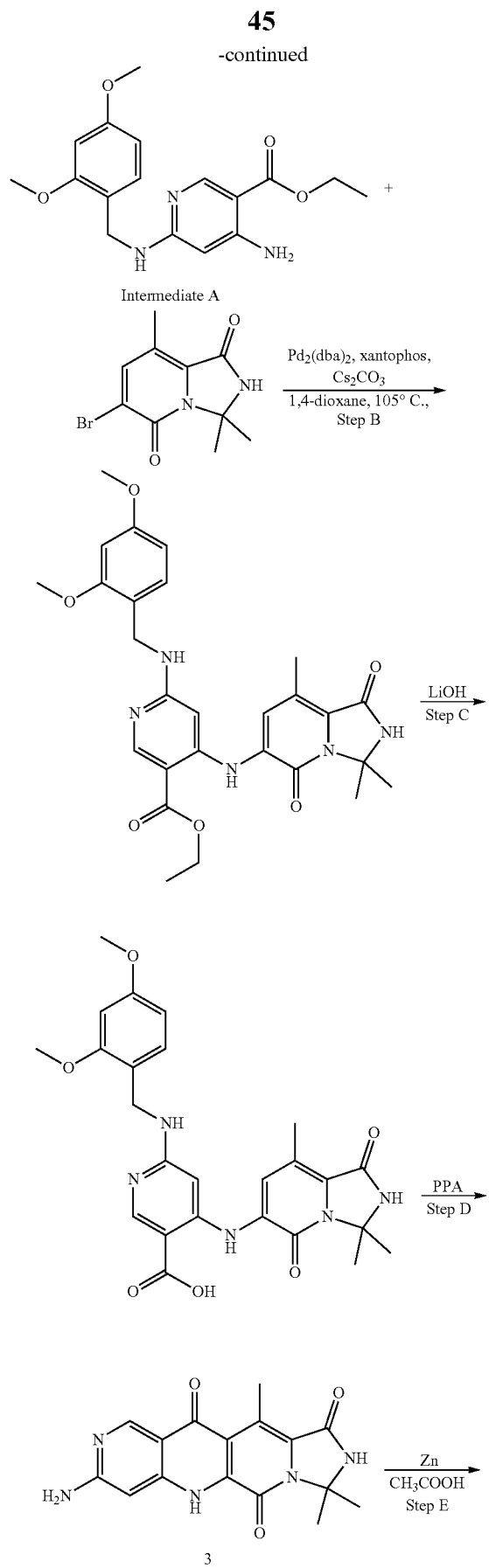

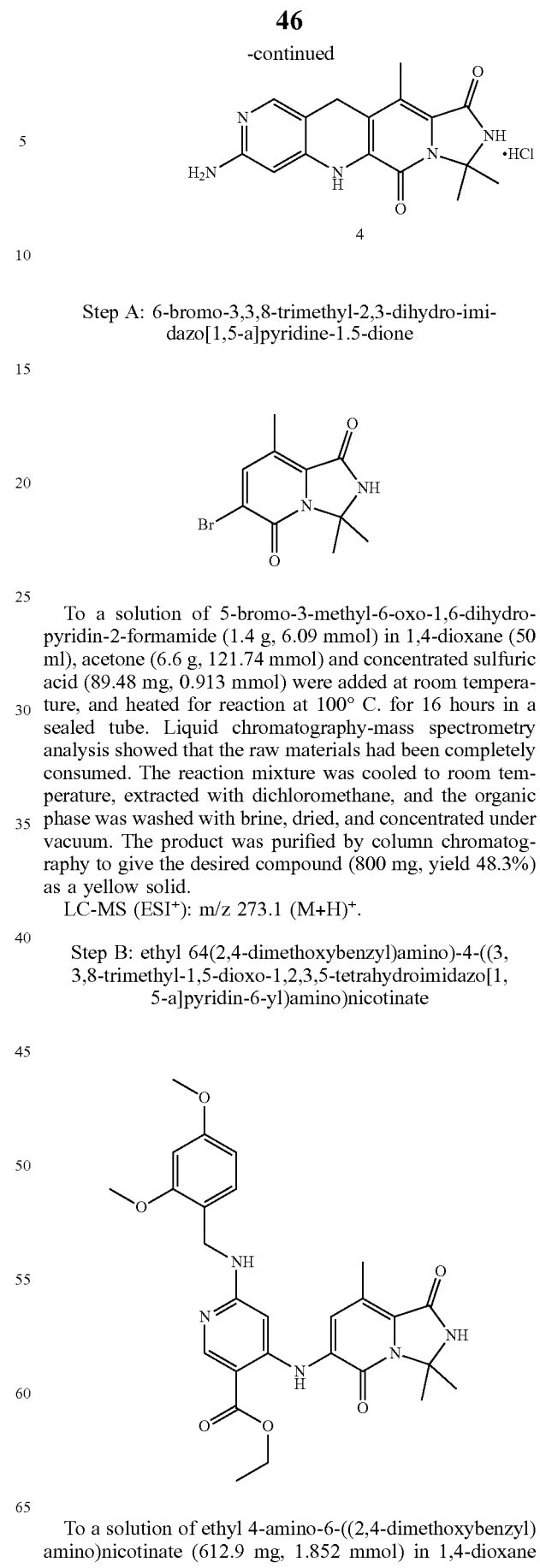

Step A: 6-bromo-3,3,8-trimethyl-2,3-dihydro-imidazo[1,5-a]pyridine-1.5-dione

To a solution of 5-bromo-3-methyl-6-oxo-1,6-dihydropyridin-2-formamide (1.4 g, 6.09 mmol) in 1,4-dioxane (50 ml), acetone (6.6 g, 121.74 mmol) and concentrated sulfuric acid (89.48 mg, 0.913 mmol) were added at room temperature, and heated for reaction at 100° C. for 16 hours in a sealed tube. Liquid chromatography-mass spectrometry analysis showed that the raw materials had been completely consumed. The reaction mixture was cooled to room temperature, extracted with dichloromethane, and the organic phase was washed with brine, dried, and concentrated under vacuum. The product was purified by column chromatography to give the desired compound (800 mg, yield 48.3%) as a yellow solid.

LC-MS (ESI$^+$): m/z 273.1 (M+H)$^+$.

Step B: ethyl 64(2,4-dimethoxybenzyl)amino)-4-((3, 3,8-trimethyl-1,5-dioxo-1,2,3,5-tetrahydroimidazo[1, 5-a]pyridin-6-yl)amino)nicotinate To a solution of ethyl 4-amino-6-((2,4-dimethoxybenzyl) amino)nicotinate (612.9 mg, 1.852 mmol) in 1,4-dioxane (50 Ml), 6-bromo-3,3,8-trimethyl-2,3-dihydroimidazo[1,5-a]pyridine-1,5-dione (500 mg, 1.852 mmol), Pd$_2$(dba)$_3$ (254.6 mg, 0.278 mmol), xantphos (160.8 mg, 0.278 mmol), cesium carbonate (1.822 g, 5.556 mmol) were added at room temperature under the protection of nitrogen. The reaction solution was evacuated and replaced with nitrogen 3 times. The reaction solution was heated at 105° C. for 12 hours under the protection of nitrogen. TLC (petroleum ether/ethyl acetate=2/1, silica gel plate) indicated that the raw materials had been completely consumed. The mixture was cooled to room temperature. The mixture was extracted with ethyl acetate (150 ml×2). The combined organic layers were washed with brine (50 ml×3), and the organic layers were combined, dried over anhydrous sodium sulfate, filtered and concentrated under vacuum. The product was purified with a chromatographic column (petroleum ether/ethyl acetate=1/1) to give the desired compound (311 mg, yield 32.2%) as a yellow solid.

LC-MS (ESI+): m/z 522.2 (M+H)+.

Step C: 6-((2,4-dimethoxybenzyl)amino)-4-((3,3,8-trimethyl-1,5-dioxo-1,2,3,5-tetrahydroimidazo[1,5-a]pyridin-6-yl)amino)nicotinic acid

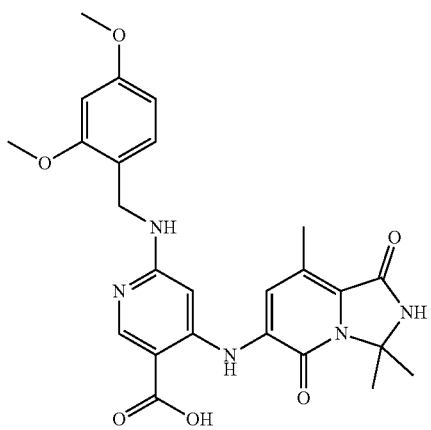

Ethyl 6-((2,4-dimethoxybenzyl)amino)-4-((3,3,8-trimethyl-1,5-dioxo-1,2,3,5-tetrahydroimidazo[1,5-a]pyridin-6-yl)amino)nicotinate (589 mg, 1.131 mmol) was dissolved in a mixed solution of tetrahydrofuran (55 ml) and methanol (10 ml) at room temperature, followed by addition of lithium hydroxide (142.4 mg, 3.392 mmol), and deionized water (10 ml). The reaction was heated at 40° C. for 12 hours. TLC (dichloromethane/methanol=10/1, silica gel plate) indicated that the raw materials had been completely consumed. The mixture was cooled to room temperature, and the residue was washed with diethyl ether (50 ml). The aqueous layer was acidified to pH=6 with 1M aqueous hydrochloric acid solution, and the aqueous phase was concentrated to dryness. The mixture was added with deionized water (10 ml), stirred for 5 minutes, filtered, washed with water and methanol. The obtained solid was dried under vacuum to give compound 6-((2,4-dimethoxybenzyl) amino)-4-((3,3,8-trimethyl-1,5-dioxo-1,2,3,5-tetrahydroimidazo[1,5-a]pyridin-6-yl)amino) nicotinic acid (491 mg, crude) as a yellow solid.

LC-MS (ESI$^+$): m/z 494.2 (M+H)$^+$.

$^1$H NMR (400 MHz, DMSO-d$_6$) δ 12.73 (s, 1H), 9.35 (s, 1H), 8.47 (s, 1H), 7.15 (d, J=8.3 Hz, 1H), 7.06 (s, 1H), 6.62 (s, 1H), 6.56 (d, J=2.3 Hz, 1H), 6.47 (dd, J=8.3, 2.3 Hz, 1H), 6.40 (s, 1H), 4.33 (d, J=5.5 Hz, 2H), 3.80 (s, 3H), 3.73 (s, 3H), 2.33 (s, 3H), 1.76 (s, 6H).

Step D: 8-amino-3,3,12-trimethyl-2,3,6,11-tetrahydroimidazo[1',5':1,6]pyrido[3,4-b][1,6]naphthyridine-1,5-dione (Compound 3)

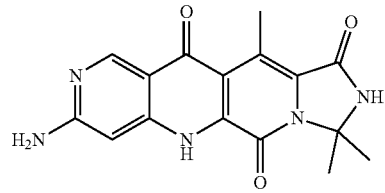 [SMILES: Cc1c2n(c(=O)c3[nH]c4cc(N)ncc4c(=O)c13)C(C)(C)NC2=O]

A mixture of 6-((2,4-dimethoxybenzyl)amino)-4-((3,3,8-trimethyl-1,5-dioxo-1,2,3,5-tetrahydroimidazo[1,5-a]pyridin-6-yl)amino)nicotinic acid (400 mg, 0.811 mmol) and polyphosphoric acid (15 g) was heated at 130° C. for 12 hours. TLC (dichloromethane/methanol=10/1, silica gel plate) indicated that the raw materials had been completely consumed. The mixture was cooled to room temperature and then poured into ice water. The aqueous layer was washed with diethyl ether (50 ml), basified to pH=7.5 with 1M sodium hydroxide, and extracted with ethyl acetate (150 ml×4), and the combined organic layers were washed with brine (50 ml×3), dried over anhydrous sodium sulfate, filtered, and concentrated under vacuum to give the target compound (251.1 mg, 95.2%) as a yellow solid compound 3.

LC-MS (ESI$^+$): m/z 326.0 (M+H)$^+$.

$^1$H NMR (400 MHz, DMSO-d$_6$) δ 11.88 (s, 1H), 9.69 (s, 1H), 8.80 (s, 1H), 7.43 (s, 2H), 6.88 (s, 1H), 2.92 (s, 3H), 1.81 (s, 6H).

Step F: 8-amino-3,3,12-trimethyl-2,3,6,11-tetrahydroimidazo[1,5':1.6]pyrido[3,4-b][1,6]naphthyridine derivative-1,5-dione hydrochloride (Compound 4)

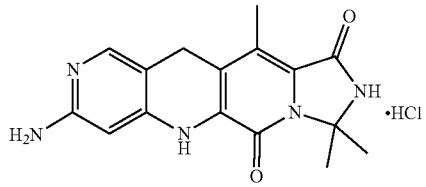 [SMILES: Cc1c2c(c(=O)n3c1C(=O)NC3(C)C)Nc1cc(N)ncc1C2 ; Cl]

In a 250 ml sealed tube, zinc powder (302 mg, 4.62 mmol) was added to a mixed solution of 8-amino-3,3,12-trimethyl-2,3-dihydroimidazo[1,5':1.6]pyrido[3,4-b][1,6]naphthyridine-1,5,11(6H)-trione (150 mg, 0.462 mmol) and acetic acid (10 ml) at room temperature. The reactants were stirred at 147° C. for 3 hours. TLC (dichloromethane/methanol=10/1, silica gel plate) indicated that the raw materials had been completely consumed. The reaction mixture was cooled to room temperature, and filtered, and the filtrate was concentrated to dryness under vacuum. The mixture was dissolved in 4 M dioxane in hydrochloric acid (30 ml), and the product was concentrated under vacuum. The obtained concentrate was purified by reverse phase column chromatography (acetonitrile/water), and purified by preparative silica gel plate to give compound 4 (6.1 mg, yield 4.2%) as a brown solid.

LC-MS (ESI+): m/z 312.0 (M+H)+.

$^1$H NMR (400 MHz, DMSO-d$_6$): δ 12.49 (s, 1H), 9.69 (s, 1H), 9.57 (s, 1H), 7.63 (s, 1H), 6.95 (s, 2H), 6.37 (s, 1H), 3.86 (s, 2H), 2.37 (s, 3H), 1.77 (s, 6H).

Example 3: Synthesis of Compounds 5 and 6

Synthesis scheme

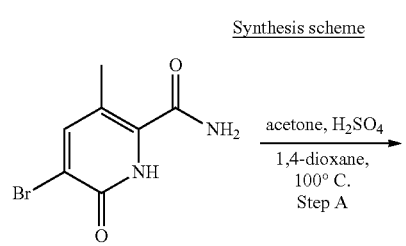

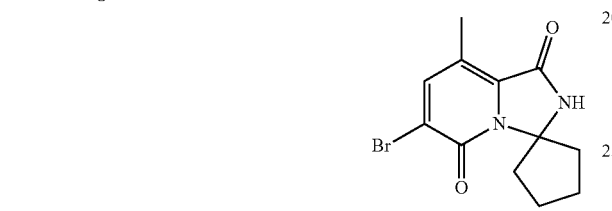

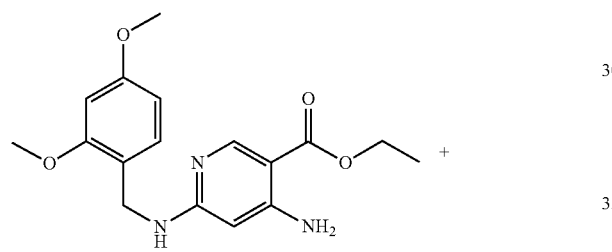

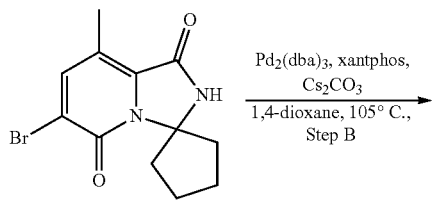

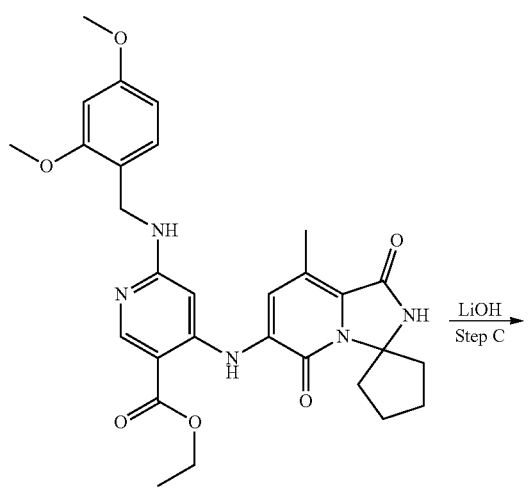

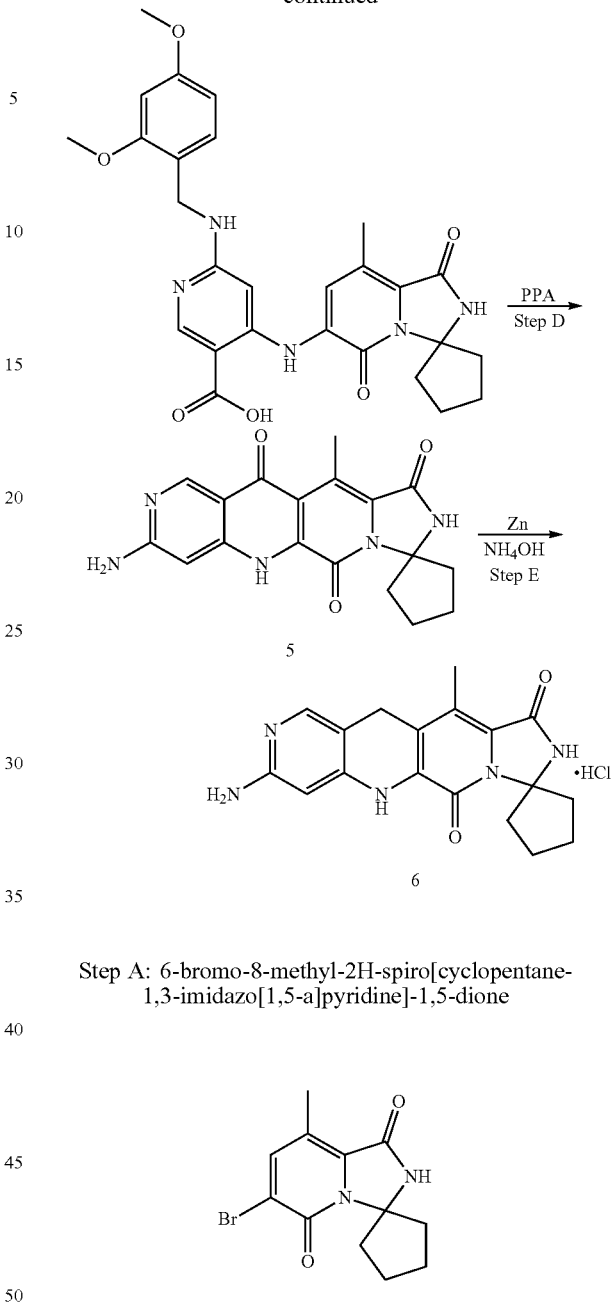

Step A: 6-bromo-8-methyl-2H-spiro[cyclopentane-1,3-imidazo[1,5-a]pyridine]-1,5-dione To a solution of 5-bromo-3-methyl-6-oxo-1,6-dihydropyridin-2-formamide (1.5 g, 6.522 mmol) in 1,4-dioxane (50 ml), cyclopentanone (8.229 g, 97.83 mmol) and concentrated sulfuric acid (95.87 mg, 0.978 mmol) were added at room temperature, and the reaction mixture was heated at 100° C. for 16 hours. Liquid chromatography-mass spectrometry analysis showed that the raw materials had been completely consumed. The reaction mixture was cooled to room temperature and extracted with ethyl acetate, and the organic phase was washed with brine, dried, and concentrated under vacuum. The product was purified by column chromatography to give the desired compound. The reaction mixture was concentrated under reduced pressure, and the residue was purified by silica gel column chromatography and eluted with petroleum ether/ethyl acetate=1/1 to give the desired compound (1.4 g, yield 72.0%) as a yellow solid.

LC-MS (ESI+): m/z 297.1 (M+H)+.

Step B: ethyl 6-((2,4-dimethoxybenzyl)amino)-4-((8-methyl-1,5-dioxo-1,5-dihydro-2H-spiro[cyclopentane-1,3-imidazo[1,5-a]pyridine]-6-yl)amino)nicotinate

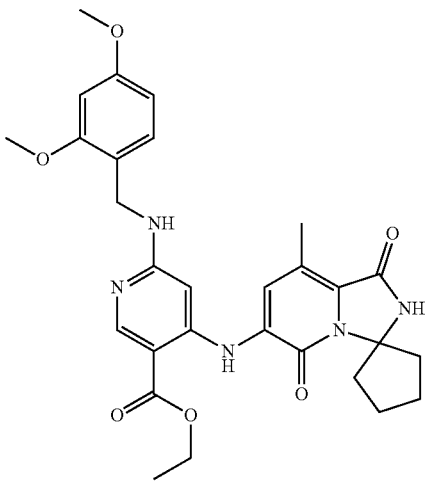 [SMILES: CCOC(=O)c1cnc(NCc2ccc(OC)cc2OC)cc1Nc1cc(C)c2n(c1=O)C1(CCCC1)NC2=O]

To a solution of 6-bromo-8-methyl-2H-spiro[cyclopentane-1,3-imidazo[1,5-a]pyridine]-1,5-dione (1.0 g, 3.78 MM) in 1,4-dioxane (100 ml), ethyl 4-amino-6-((2,4-dimethoxybenzyl) amino)nicotinate (1.118 g, 3.378 mmol), $Pd_2(dba)_3$ (464.1 mg, 0.507 mmol), xantphos (293.2 mg, 0.507 mmol), cesium carbonate (2.77 g, 8.45 mmol) were added at room temperature under the protection of nitrogen. The reaction solution was heated at 105° C. for 12 hours under the protection of nitrogen. TLC (petroleum ether/ethyl acetate=2/1, silica gel plate) indicated that the raw materials had been completely consumed. The mixture was cooled to room temperature, and extracted with ethyl acetate (150 ml×2). The combined organic layers were washed with brine (50 ml×3), dried over anhydrous sodium sulfate, filtered and concentrated under vacuum. The product was purified with a chromatographic column (petroleum ether/ethyl acetate=1/1) to give the desired compound (611.0 mg, yield 33.1%) as a yellow solid.

LC-MS (ESI+): m/z 548.2 (M+H)+.

Step F: 6-((2,4-dimethoxybenzyl)amino)-4-((8-methyl-1,5-dioxo-1,5-dihydro-2H-spiro[cyclopentane-1,3-imidazo[1,5-a]pyridine]-6-yl)amino)nicotinic acid

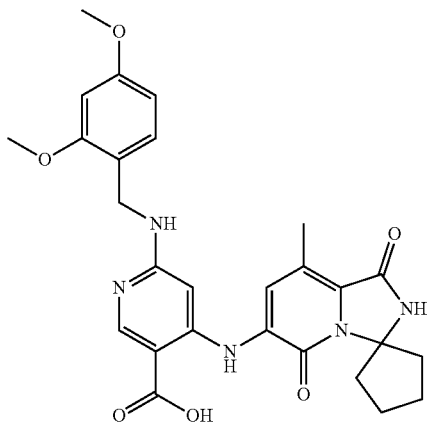 [SMILES: COc1ccc(CNc2cc(Nc3cc(C)c4n(c3=O)C3(CCCC3)NC4=O)c(C(=O)O)cn2)c(OC)c1]

Ethyl 6-((2,4-dimethoxybenzyl) amino)-4-((8-methyl-1,5-dioxo-1,5-dihydro-2H-spiro[cyclopentane-1,3-imidazo[1,5-a]pyridine]-6-yl)amino)nicotinate (611 mg, 1.117 mmol) was dissolved in a mixed solution of tetrahydrofuran (115 ml) and methanol (15 ml), followed by addition of lithium hydroxide (141 mg, 3.35 mmol) and deionized water (12 ml). The reaction was heated at 60° C. for 12 hours. TLC (dichloromethane/methanol=10/1, silica gel plate) indicated that the raw materials had been completely consumed. The mixture was cooled to room temperature, and the residue was washed with diethyl ether (50 ml). The aqueous layer was acidified to pH=6 with 1M aqueous hydrochloric acid solution. The mixture was concentrated to dryness. The mixture was added with deionized water (10 ml), stirred for 5 minutes, filtered, and washed with water and methanol. The obtained solid was dried under vacuum to give the target compound (551 mg, 95%) as a yellow solid.

LC-MS (ESI+): m/z 520.2 (M+H)+.

1H NMR (400 MHz, DMSO-$d_6$) δ 11.03 (s, 1H), 9.83 (s, 1H), 8.55 (s, 1H), 7.23 (s, 2H), 7.15 (d, J=8.3 Hz, 1H), 6.58 (d, J=2.0 Hz, 2H), 6.49 (dd, J=8.3, 2.1 Hz, 1H), 4.39 (d, J=4.4 Hz, 2H), 3.80 (s, 3H), 3.74 (s, 3H), 2.88-2.72 (m, 2H), 2.38 (s, 3H), 2.04-1.91 (m, 2H), 1.88-1.73 (m, 2H), 1.70-1.58 (m, 2H).

Step G: 8-amino-12-methyl-2H-spiro[cyclopentane-1,3-imidazo[1,5:1,6]pyridine[3,4-b][1,6]naphthyridine]-1,5,11(6H)-trione (Compound 5)

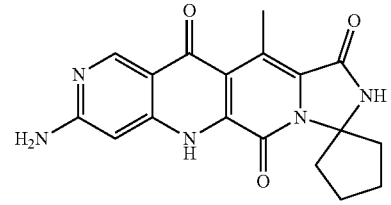 [SMILES: Cc1c2n(c(=O)c3[nH]c4cc(N)ncc4c(=O)c13)C1(CCCC1)NC2=O]

A mixture of 6-((2,4-dimethoxybenzyl)amino)-4-((8-methyl-1,5-dioxo-1,5-dihydro-2H-spiro[cyclopentane-1,3-imidazo[1,5-a]pyridine]-6-yl)amino)nicotinic acid (551 mg, 1.062 mmol) and polyphosphoric acid (20 g) was heated at 130° C. for 12 hours. TLC (dichloromethane/methanol=10/1, silica gel plate) indicated that the raw materials had been completely consumed. The mixture was cooled to room temperature and then poured into ice water. The aqueous layer was washed with diethyl ether (50 ml), basified to pH=7.5 with 1M sodium hydroxide, and then extracted with a mixed solvent of dichloromethane and isopropanol (dichloromethane and isopropanol=3/1, 100 ml×8). The combined organic layers were washed with brine (50 ml), dried over anhydrous sodium sulfate, filtered, and concentrated under vacuum. The product was adjusted to pH=6.0 with 1 N aqueous hydrochloric acid solution, dissolved in methanol (10 ml), and prepared into a sample with silica gel, which was purified by reverse phase column chromatography (acetonitrile/water) to give compound 5 (166.1 mg, 44.6%) as a yellow solid.

LC-MS (ESI+): m/z 352.0 (M+H)+.

1H NMR (400 MHz, DMSO-$d_6$) δ 11.70 (s, 1H), 9.96 (s, 1H), 8.79 (s, 1H), 6.98 (s, 2H), 6.70 (s, 1H), 2.94 (s, 3H), 2.86-2.74 (m, 2H), 2.02 (qt, J=9.9, 5.1 Hz, 2H), 1.84 (dd, J=15.4, 10.9 Hz, 2H), 1.73 (dd, J=12.3, 5.8 Hz, 2H).

Step H: 8'-amino-12'-methyl-6',11'-dihydro-2'H-spiro[cyclopentane-1,3'-imidazo[1',5':1,6]pyrido[3,4-b][1,6]naphthyridine]-1',5'-dione (Compound 6)

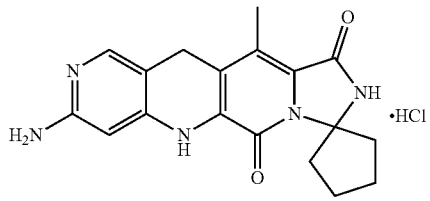 [SMILES: Cc1c2c(c(=O)n3c1C(=O)NC31CCCC1)Nc1cc(N)ncc1C2 ; Cl]

In a 250 ml sealed tube, zinc powder (224 mg, 3.42 mmol) was added to a mixed solution of 8-amino-12-methyl-2H-spiro[cyclopentane-1,3-imidazo[1,5:1,6]pyrido[3,4-b][1,6]naphthyridine]-1,5,11(6H)-trione (compound 5) (120 mg, 0.342 mmol) and NH₄OH (15 ml) at room temperature. The reactants were stirred at 105° C. for 12 hours. TLC (dichloromethane/methanol=10/1, silica gel plate) indicated that the raw materials had been completely consumed. The reaction mixture was cooled to room temperature, concentrated to dryness under vacuum. The mixture was dissolved in tetrahydrofuran (25 ml) and methanol (25 ml) and filtered, and then the filtrate was concentrated, adjusted to pH=6.0 with 1 N aqueous hydrochloric acid solution, and concentrated under vacuum to dryness. The obtained concentrate was purified by reverse phase column chromatography (acetonitrile/water) to give compound 6 (21.1 mg, yield 18.3%) as a yellow solid.

LC-MS (ESI⁺): m/z 338.0 (M+H)⁺.

¹H NMR (400 MHz, DMSO-d₆): δ 12.34 (s, 1H), 10.02 (s, 1H), 9.93 (s, 1H), 7.63 (s, 1H), 7.37 (s, 2H), 6.44 (s, 1H), 3.88 (s, 2H), 2.85-2.71 (m, 2H), 2.38 (s, 3H), 2.04-1.92 (m, 2H), 1.89-1.76 (m, 2H), 1.74-1.62 (m, 2H).

Example 4: Synthesis of Compounds 7 and 8

Synthesis scheme

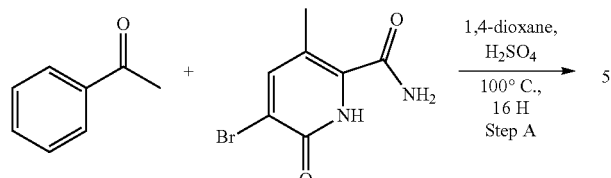

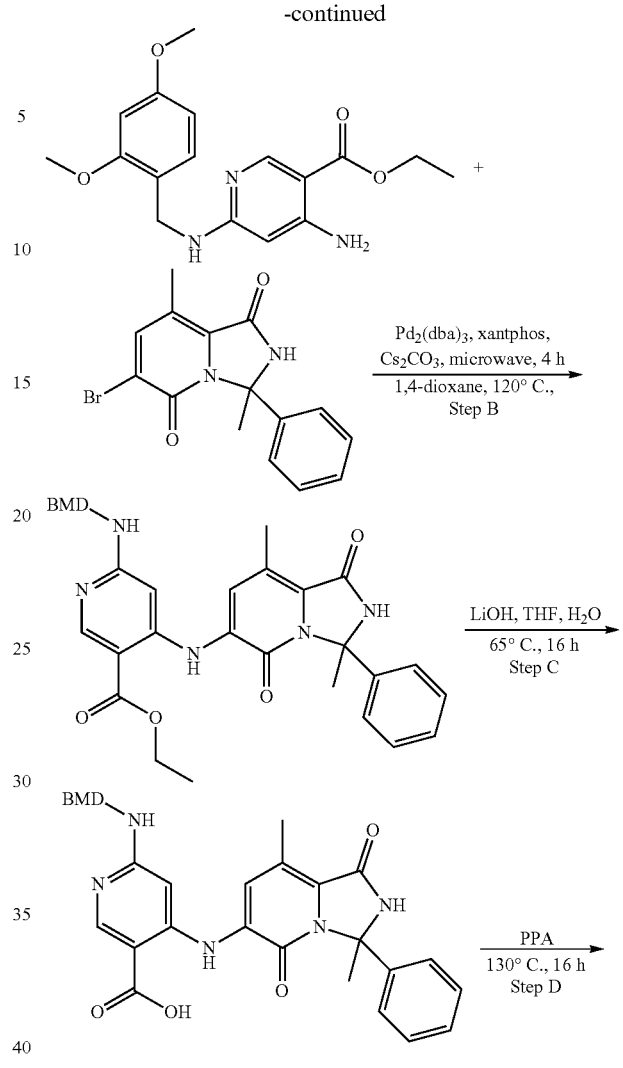

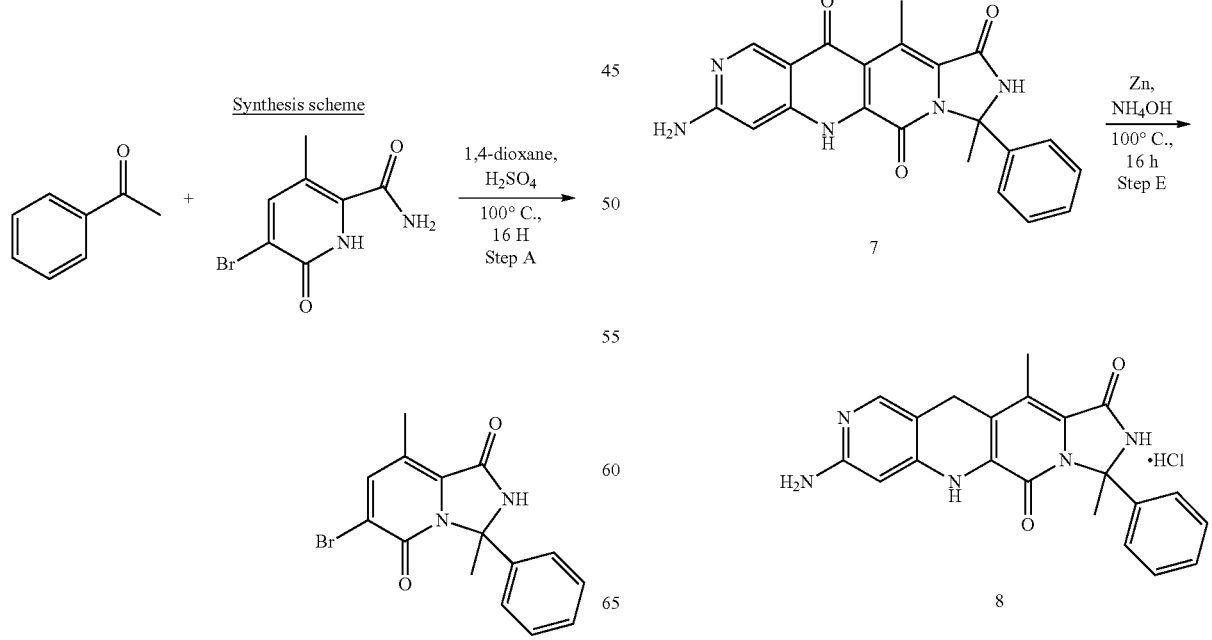

Step A: 6-bromo-3,8-dimethyl-3-phenyl-2,3-dihydroimidazo[1,5-a]pyridin-1,5-dione

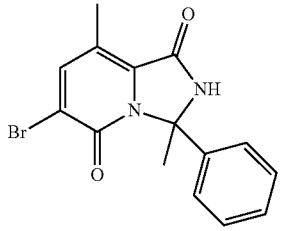 [SMILES: Cc1cc(Br)c(=O)n2c1C(=O)NC2(C)c1ccccc1]

To anhydrous 1,4-dioxane (50 ml), 5-bromo-3-methyl-6-oxo-1,6-dihydropyridin-2-formamide (2.2 g, 9.57 mmol), acetophenone (17.24 g, 143.44 mmol) and concentrated sulfuric acid (140.6 mg, 1.43 mmol) were added at room temperature, and heated to 100° C. and stirred for 16 hours. TLC plate (petroleum ether/ethyl acetate=2/1, silica gel plate) showed that the starting materials had been completely consumed. The reaction solution was cooled to normal temperature, extracted with ethyl acetate, washed with brine, dried over anhydrous sodium sulfate, and then concentrated under vacuum under reduced pressure. The concentrated residue was purified by silica gel elution column chromatography (petroleum ether/ethyl acetate=1/1) to give the white target product (1.676 g, conversion 52.6%)

LC-MS (ESI$^+$): m/z 333.0 (M+H)$^+$.

Step B: ethyl methyl-4-((3,8-dimethyl-1,5-dioxo-3-phenyl-1,2,3,5-tetrahydroimidazo[1,5-a]pyridin-6-yl)amino)-6-((3-,4-methylbenzyl)amino)nicotinate

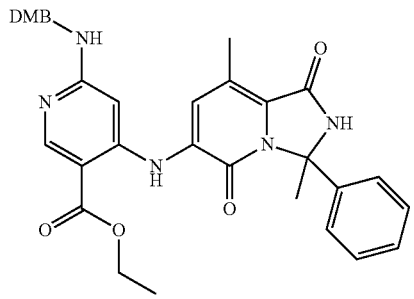

To anhydrous 1,4-dioxane (14 ml), 6-bromo-3,8-dimethyl-3-phenyl-2,3-dihydroimidazo[1,5-a]pyridin-1,5-dione (550 mg, 1.66 mmol), ethyl 4-amino-6-((2,4-dimethoxybenzyl) amino)nicotinate (500 mg, 1.49 mmol), tris(dibenzylideneacetone)dipalladium (152 mg, 0.166 mmol), 4,5-bis(diphenylphosphine)-9,9-dimethylxanthene (192 mg, 0.332 mmol), cesium carbonate (1.09 g, 3.323 mmol) were added at room temperature under anhydrous and oxygen-free conditions. The reaction solution was evacuated and replaced with nitrogen 3 times, and then the reaction mixture was reacted in a microwave at 120° C. for 3.5 hours. LC-MS indicated that the raw materials had been completely consumed. The mixture was added with water (50 ml), and extracted with ethyl acetate (50 ml×3). The combined organic layers were washed with brine (50 ml×3), dried over anhydrous sodium sulfate, filtered and concentrated under vacuum. The concentrated product was purified with a chromatographic column (petroleum ether/ethyl acetate=1/1) to give the yellow target product (725 mg, conversion 82.4%).

LC-MS (ESI$^+$): m/z 584.4 (M+H)$^+$.

Step C: 4-((3,8-dimethyl-1,5-dioxo-3-phenyl-1,2,3,5-tetrahydroimidazo[1,5-a]pyridin-6-yl)amino)-6-((3-,4-dimethylbenzyl)amino)nicotinic acid

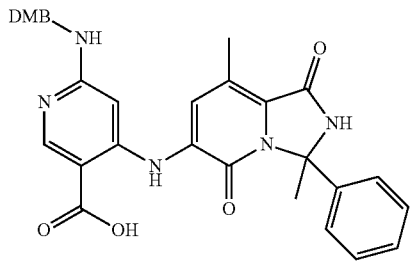

To tetrahydrofuran (40 ml), ethyl 4-((3,8-dimethyl-1,5-dioxo-3-phenyl-1,2,3,5-tetrahydroimidazo[1,5-a]pyridin-6-yl)amino)-6-((3,4-dimethylbenzyl)amino)nicotinate (1.45 g, 2.49 mmol), water (10 ml), lithium hydroxide (627 mg, 14.9 mmol) were added at room temperature in an oxygen-free environment, heated to 65° C. and stirred for 16 hours. LC-MS indicated that the raw materials had been completely consumed. The mixture was cooled to room temperature, and concentrated under vacuum. The mixture was added with water (10 ml), stirred for 5 minutes, adjusted to pH 5 with 1M hydrochloric acid solution, and filtered o give the target product (1.34 g, yield 97%) as a yellow solid.

LC-MS (ESI$^+$): m/z 556.4 (M+H)$^+$.

Step D: 8-amino-3,12-dimethyl-3-phenyl-2,3-dihydroimidazo[1',5':1,6]pyrido[3,4-B][1,6]naphthyridine-1,5,11(6H)-trione (Compound 7)

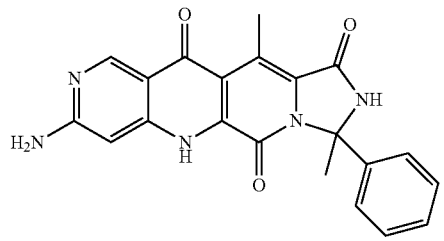 [SMILES: Cc1c2n(c(=O)c3[nH]c4cc(N)ncc4c(=O)c13)C(C)(c1ccccc1)NC2=O]

A mixture of polyphosphoric acid (30 ml) and 4-((3,8-dimethyl-1,5-dioxin-3-phenyl-1,2,3,5-tetrahydroimidazo[1,5-a]pyridin-6-yl)amino)-6-((3,4-dimethylphenyl)amino) nicotinic acid (1.2 g, 2.162 mmol) was heated to 130° C. and reacted for 16 hours. LC-MS indicated that the raw materials had been completely consumed. The mixture was cooled to normal temperature, poured into ice water, adjusted to pH 7.0 with a saturated sodium carbonate solution, extracted with a mixed organic solvent of dichloromethane/isopropanol (dichloromethane/isopropanol=3/1) (150 ml×4), and filtered off floccules. The organic phase was concentrated, and purified by reversed phase column chromatography, to give the target product 7 (182 mg, yield 21.71%) as a green solid.

LC-MS (ESI+): m/z 388.0 (M+H)⁺.

¹H NMR (400 MHz, DMSO-d₆) δ 11.67 (s, 1H), 10.00 (s, 1H), 8.80 (s, 1H), 7.44-7.35 (m, 5H), 7.35 (s, 2H), 6.70 (s, 1H), 2.99 (s, 3H), 2.66 (s, 3H).

Step 5: 8-amino-3,12-dimethyl-3-phenyl-2,3,6,11-tetrahydroimidazo[1',5':1,6]pyrido[3,4-b][1,6]naphthyridine-1,5-dione, hydrochloride (Compound 8)

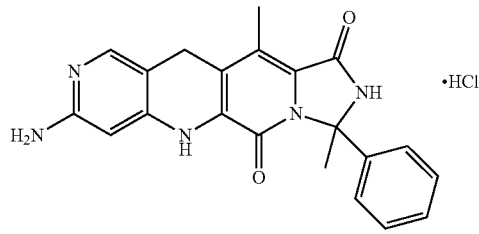 [SMILES: Cc1c2c(c(=O)n3c1C(=O)NC3(C)c1ccccc1)Nc1cc(N)ncc1C2 ; Cl]

Zinc powder (281 mg, 4.4 mmol) was added to an ammonia solution (40 ml) containing 8-amino-3,12-dimethyl-3-phenyl-2,3-dihydroimidazo[1',5':1,6]pyrido[3,4-B][1,6]naphthyridine-1,5,11(6H)-trione (170 mg, 0.44 mmol) at room temperature. The reaction was stirred at 100° C. for 16 hours in a 350 ml sealed tube. LC-MS indicated that the raw materials had been completely consumed. The reaction mixture was cooled to room temperature and filtered, and the filtrate was concentrated under vacuum. The concentrated product was dissolved in hydrochloric acid in methanol and purified by reversed phase column chromatography (methanol/water=33/100) to give the target product 8 (10.6 mg, yield 6.4%) as a pink solid.

LC-MS (ESI+): m/z 374.0 (M+H)⁺.

1H NMR (400 MHz, DMSO) δ 12.32 (s, 1H), 9.94 (s, 1H), 9.88 (s, 1H), 7.63 (s, 1H), 7.41-7.26 (m, 7H), 6.35 (s, 1H), 3.91 (s, 2H), 2.45 (s, 3H), 2.23 (s, 3H).

Example 5: Synthesis of Compounds 9 and 10

Synthesis scheme

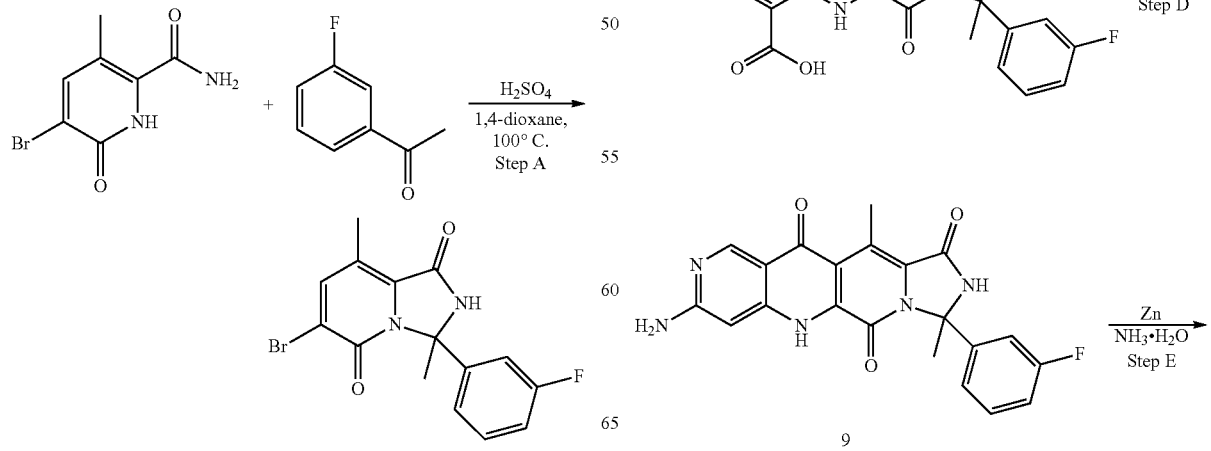

-continued

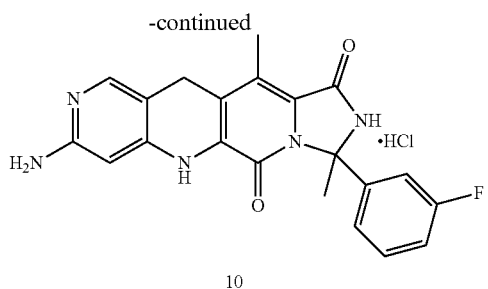

Step A: 6-bromo-3-(3-fluorophenyl)-3,8-dimethyl-2,3-dihydroimidazo[1,5-a]pyridin-1,5-dione

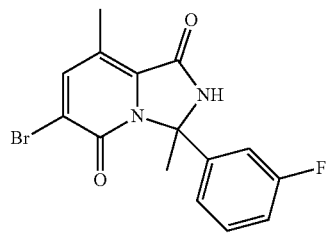 [SMILES: Cc1cc(Br)c(=O)n2c1C(=O)NC2(C)c1cccc(F)c1]

To a dioxane (50 ml) solvent, 5-bromo-3-methyl-6-oxo-1,6-dihydropyridin-2-formamide (1.7 g, 7.35 mmol), 3-fluorobenzophenone (10.1 g, 73.5 mmol), concentrated sulfuric acid (72 mg, 0.74 mmol) were successively added, and the reaction was heated at 100° C. for 16 hours. The reaction mixture was cooled to room temperature, diluted with water, and extracted with ethyl acetate (50 ml×2). The organic phase was dried, concentrated, and subjected to column chromatography (mobile phase: petroleum ether/ethyl acetate=1/1) to give a white product (1.4 g, yield: 54.3%).

$^1$H NMR (400 MHz, CDCl$_3$) δ 7.77 (s, 1H), 7.34 (td, J=8.1, 5.9 Hz, 1H), 7.23 (ddd, J=7.9, 1.8, 0.9 Hz, 1H), 7.14 (dt, J=9.9, 2.2 Hz, 1H), 7.06 (tdd, J=8.2, 2.5, 0.8 Hz, 1H), 6.90 (s, 1H), 2.53 (s, 3H), 2.34 (s, 3H).

LC-MS (ESI$^+$): m/z 352.2 (M+H)$^+$.

Step B: ethyl 6-(2,4-dimethoxybenzylamino)-4-(3-(3-fluorophenyl)-3,8-dimethyl-1,5-dioxo-1,2,3,5-tetrahydroimidazo[1,5-a]pyridin-6-ylamino)nicotinate

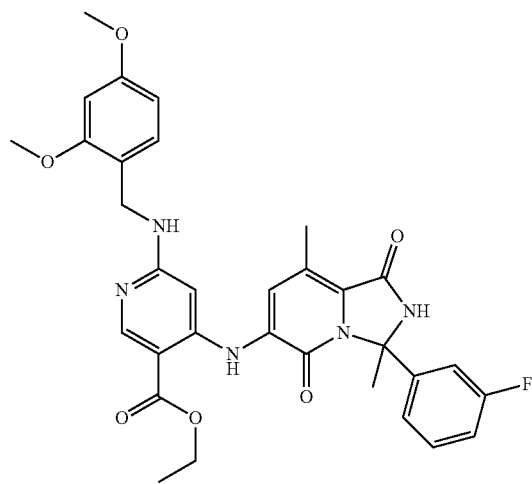 [SMILES: CCOC(=O)c1cnc(NCc2ccc(OC)cc2OC)cc1Nc1cc(C)c2n(c1=O)C(C)(c1cccc(F)c1)NC2=O]

To a 25 ml microwave tube, dioxane (2 ml), ethyl 4-amino-6-(2,4-dimethoxybenzylamino)nicotinate (1.4 g, 3.98 mmol), 6-bromo-3-(3-fluorophenyl)-3,8-dimethyl-2,3-dihydroimidazo[1,5-a]pyridin-1,5-dione (1.15 g, 3.48 mmol), bi-tris(dibenzylideneacetone)dipalladium (354 mg, 0.386 mmol), 4,5-bis(diphenylphosphine)-9,9-dimethylxanthene (449 Mg, 0.77 mmol), cesium carbonate (2.54 g, 7.73 mmol) were successively added under the protection of nitrogen, and reacted in a microwave at 120° C. for 4 hours. The reaction solution was cooled to room temperature, poured into water, and extracted with ethyl acetate (50 ml×2). The organic phase was dried, concentrated, and subjected to column chromatography (petroleum ether:ethyl acetate=1:1), to give a yellow solid (1.5 g, yield: 62.5%).

LC-MS (ESI$^+$): m/z 602.3 (M+H)$^+$.

Step C: 6-(2,4-dimethoxybenzylamino)-4-(3-(3-fluorophenyl)-3,8-dimethyl-1,5-dioxo-1,2,3,5-tetrahydroimidazo[1,5-a]pyridin-6-ylamino)nicotinic acid

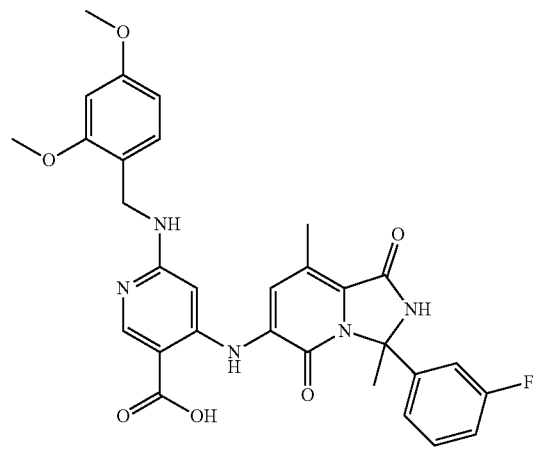 [SMILES: COc1ccc(CNc2cc(Nc3cc(C)c4n(c3=O)C(C)(c3cccc(F)c3)NC4=O)c(C(=O)O)cn2)c(OC)c1]

To a mixed solution of tetrahydrofuran (150 ml) and water (100 ml), ethyl 6-(2,4-dimethoxybenzylamino)-4-(3-(3-fluorophenyl)-3,8-dimethyl-1,5-dioxo-1,2,3,5-tetrahydroimidazo[1,5-a]pyridin-6-ylamino)nicotinate (1.5 g, 2.5 mmol), lithium hydroxide (1.05 g, 25 mmol) were added, and the mixture was heated for reaction at 60° C. for 12 hours. The mixture was cooled to room temperature and subjected to reduced pressure to remove tetrahydrofuran, and the aqueous phase was adjusted to pH 6 with 1M hydrochloric acid.

Precipitation of solid was observed. A filter cake was obtained after filtration and dried under vacuum to give a yellow solid (1.6 g, crude).

LC-MS (ESI$^+$): m/z 574.3 (M+H)$^+$.

Step D: 8-amino-3-(3-fluorophenyl)-3,12-dimethyl-2,3-dihydroimidazo[1',5':1,6]pyrido[3,4-b][1,6]naphthopyridin-1,5,11(6H)-trione (Compound 9)

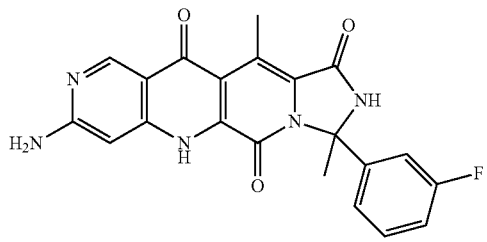 [SMILES: Cc1c2n(c(=O)c3[nH]c4cc(N)ncc4c(=O)c13)C(C)(c1cccc(F)c1)NC2=O]

To a mixed solvent of trifluoromethanesulfonic acid and polyphosphoric acid (trifluoromethanesulfonic acid/polyphosphoric acid=5/1, 10 ml), 6-(2,4-dimethoxy benzylamino)-4-(3-(3-fluorophenyl)-3,8-dimethyl-1,5-dioxo-1,2,3,5-tetrahydroimidazo[1,5-a]pyridin-6-ylamino)nicotinic acid (700 mg, 1.22 mmol) was added, and the reaction system was heated for reaction at 130° C. for 12 hours. After being cooled to room temperature, the mixture was poured into ice water, adjusted to pH=7.5 with a saturated sodium carbonate solution, and then extracted with a mixed solvent of dichloromethane and isopropanol (dichloromethane and isopropanol=3/1, 100 ml×8). The combined organic layers were washed with brine (50 ml×1), dried over anhydrous sodium sulfate, filtered, and concentrated under vacuum. The product was purified by reverse phase column chromatography (acetonitrile/water) to give the target product 9 (103 mg, yield: 20.8%) as a yellow solid.

$^1$H NMR (400 MHz, DMSO-$d_6$) δ 11.44 (s, 1H), 9.95 (s, 1H), 8.79 (s, 1H), 7.49-7.36 (m, 1H), 7.31 (dt, J=10.5, 2.1 Hz, 1H), 7.20 (td, J=8.3, 2.3 Hz, 2H), 6.70 (s, 2H), 6.50 (s, 1H), 3.00 (s, 3H), 2.23 (s, 3H).

LC-MS (ESI$^+$): m/z 406.3 (M+H)$^+$.

Step E: 8-amino-3-(trifluorophenyl)-3,12-dimethyl-2,3,6,11-tetrahydroimidazo[1,5':1.6]pyrido[3,4-b][1,6]naphthyridine derivative-1,5-dione hydrochloride (Compound 10)

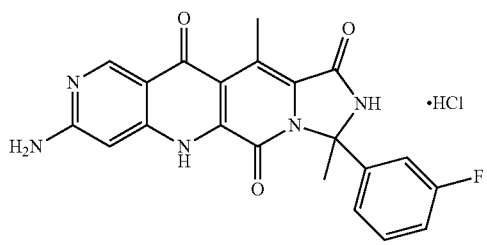 [SMILES: Cc1c2n(c(=O)c3[nH]c4cc(N)ncc4c(=O)c13)C(C)(c1cccc(F)c1)NC2=O ; Cl]

In a 250 ml sealed tube, 8-amino-3-(3-fluorophenyl)-3,12-dimethyl-2,3-dihydroimidazo[1',5':1,6]pyrido[3,4-b][1,6]naphthopyridin-1,5,11(6H)-trione (78 mg, 0.19 mmol) and zinc powder (128 mg, 1.97 mmol) were added to 10 ml of ammonia water, and heated at 100° C. overnight. The reaction mixture was cooled to room temperature, and filtered off the solid residue, and the filtrate was concentrated under vacuum. The product was dissolved in hydrochloric acid in dioxane (20 ml), and purified by reverse phase column chromatography (acetonitrile/water) to give a red solid compound 10 (15 mg, yield: 19.9%).

$^1$H NMR (400 MHz, DMSO-$d_6$): δ 12.45 (s, 1H), 9.97 (s, 1H), 9.90 (s, 1H), 7.64 (s, 1H), 7.48-7.34 (m, 3H), 7.27-7.13 (m, 3H), 6.36 (s, 1H), 3.91 (s, 2H), 2.43 (s, 3H), 2.21 (s, 3H).

LC-MS (ESI$^+$): m/z 392.2 (M+H)$^+$.

Example 6: Synthesis of Compounds 11 and 12

Synthesis scheme

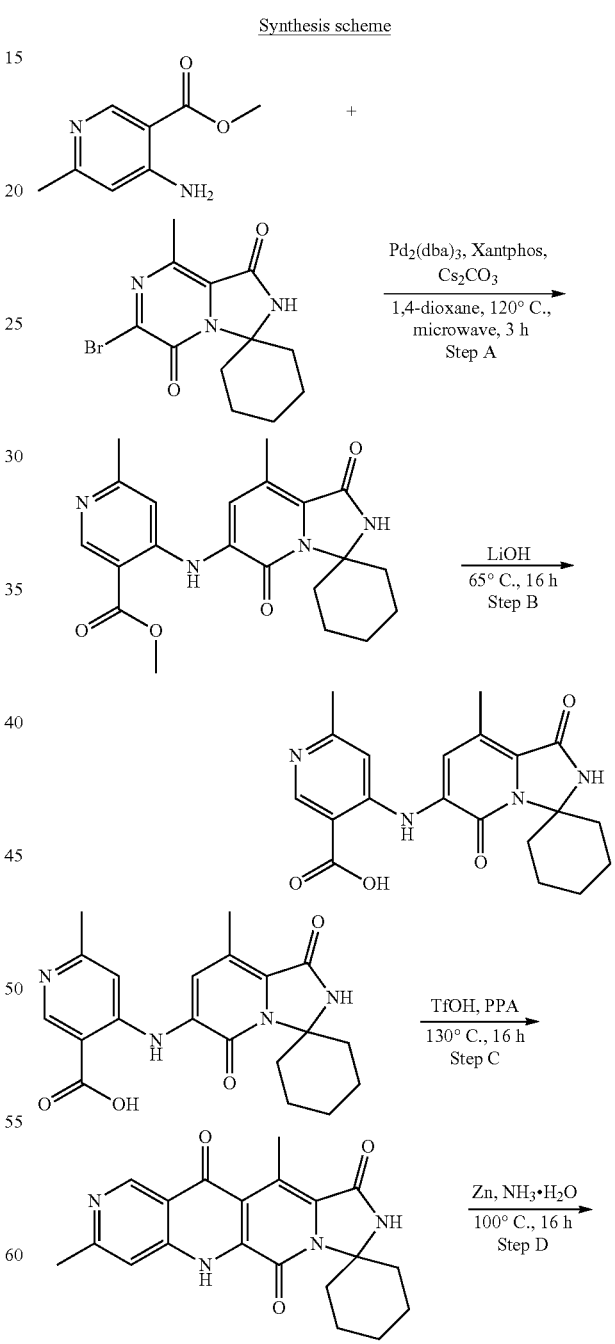

11

-continued

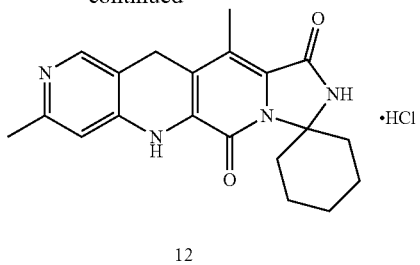

12

Step A: methyl 6-methyl-4-((8-methyl-1,5-dioxo-2,5-dihydro-1H-spiro[cyclohexane-1,3-imidazo[1,5-a]pyridine]-6-yl)amino)nicotinate

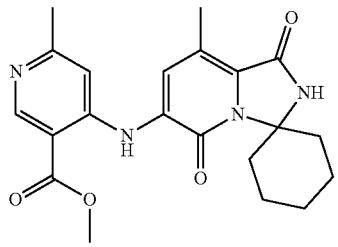 [SMILES: COC(=O)c1cnc(C)cc1Nc1cc(C)c2n(c1=O)C1(CCCCC1)NC2=O]

The raw material methyl 4-amino-6-methylnicotinate (510 mg, 3.07 mmol), the raw material 6-bromo-8-methyl-1H-spiro[cyclohexane-1,3-imidazo[1,5-a]pyridine]-1,5(2H)-dione (1.05 g, 3.38 mmol), $Pd_2(dba)_3$ (280 mg, 0.31 mmol), Xantphos (356 mg, 0.61 mmol) and cesium carbonate (2.0 g, 6.14 mmol) were mixed in 1,4-dioxane (15 ml) at room temperature under the protection of nitrogen. After being replaced with nitrogen, the reaction was carried out under microwave conditions at 120° C. for 3.5 hours. LC-MS detection showed that the raw materials had been completely converted. The reaction solution was cooled to room temperature and poured into a mixture of ethyl acetate (50 ml) and water (100 ml). Then the mixture was filtered, and the filter cake was washed with 20 ml of ethyl acetate, evacuated to dryness, and subjected to water removal with toluene twice, to give the product (1.41 g, yield 90%) as a yellow solid.

LC-MS (ESI$^+$): m/z 397.0 (M+H)$^+$.

Step B: 6-methyl-44(8-methyl-1,5-dioxo-2,5-dihydro-1H-spiro[cyclohexane-1,3-imidazo[1,5-a]pyridine]-6-yl)amino)nicotinic acid

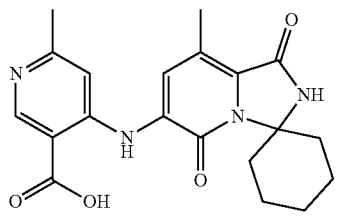 [SMILES: Cc1cc(Nc2cc(C)c3n(c2=O)C2(CCCCC2)NC3=O)c(C(=O)O)cn1]

Methyl 6-methyl-4-((8-methyl-1,5-dioxo-2,5-dihydro-1H-spiro[cyclohexane-1,3-imidazo[1,5-a]pyridine]-6-yl)amino)nicotinate (1.4 g, 3.5 mmol) and lithium hydroxide monohydrate (600 mg, 14.0 mmol) were mixed in tetrahydrofuran (40 ml) and water (20 ml) at room temperature. The reaction was heated at 65° C. for 16 hours. LC-MS showed complete conversion. The organic solvent was removed by rotary evaporation. The remaining aqueous phase was extracted with dichloromethane (40 ml), and then the aqueous layer was acidified to pH=4 with 4 M hydrochloric acid solution. The mixture was filtered, and the filter cake was dried to give a yellow solid product (1.07 g, yield 80%).

LC-MS (ESI$^+$): m/z 383.0 (M+H)$^+$.

Step C: 8',12'-dimethyl-1'H-spiro[cyclohexane-1,3'-imidazo[1',5':1,6]pyrido[3,4-b][1,6]naphthyridine]-1',5',11'(2'H,6'H)-trione (Compound 11)

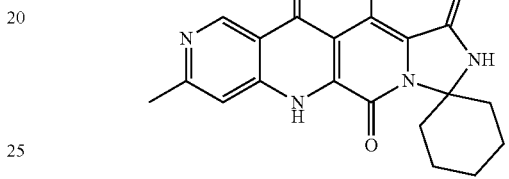

6-Methyl-4-((8-methyl-1,5-dioxo-2,5-dihydro-1H-spiro[cyclohexane-1,3-imidazo[1,5-a]pyridine]-6-yl)amino)nicotinic acid (450 mg, 1.18 mmol) was mixed in trifluoromethanesulfonic acid and polyphosphoric acid (trifluoromethanesulfonic acid/polyphosphoric acid=5/1, 7 ml). The mixture was stirred at 130° C. for 18 hours. LC-MS showed that the raw materials had been completely consumed. The reaction solution was cooled to room temperature and poured into ice water (10 ml) and methanol (10 ml), and the mixture was poured into a saturated sodium carbonate solution (60 ml), and extracted with a mixed solvent of dichloromethane and isopropanol (dichloromethane and isopropanol=3/1, 70 ml×6). The extracts were combined, dried over anhydrous sodium sulfate, and concentrated under vacuum. The residue was stirred in dichloromethane/methanol (30 ml/1.5 ml) for half an hour, and then the mixture was filtered. The filter cake was dried to give the product (400 mg, yield 93%) as a yellow solid compound 11.

$^1$H NMR (400 MHz, DMSO-d$_6$): δ 12.07 (s, 1H), 10.23 (s, 1H), 9.15 (s, 1H), 7.66 (s, 1H), 2.97 (m, 5H), 2.55 (s, 3H), 1.70 (m, 5H), 1.53 (d, J=12.1 Hz, 2H), 1.25 (m, 1H).

LC-MS (ESI$^+$): m/z 365.0 (M+H)$^+$.

Step D: 8,12-dimethyl-6,11-dihydro-1H-spiro[cyclohexane-1,3-imidazo[1,5:1,6]pyrido[3,4-b][1,6]naphthyridine]-1,5(2H)-dione hydrochloride (Compound 12)

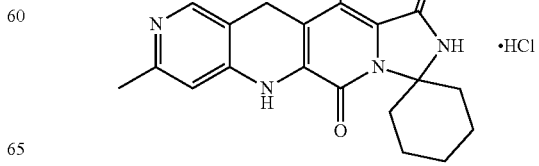

8,12-Methyl-1H-spiro[cyclohexane-1,3-imidazo[1,5:1,6]pyrido[3,4-b][1,6]cycloalkane]-1,5,11(2H,6H)-trione (100 mg, 0.275 mmol) and zinc powder (180 mg, 2.75 mmol) were mixed in ammonia water (15 ml). The reaction was heated and stirred at 100° C. for 16 hours in a sealed tube. LC-MS detection showed that the raw materials had been completely consumed. The reaction mixture was cooled to room temperature. After rotary evaporation, the mixture was dissolved in tetrahydrofuran (25 ml) and methanol (25 ml) and filtered, and the filtrate was concentrated under vacuum. The product was acidified to pH=6.0 with 1 N hydrochloric acid solution. The product was concentrated under vacuum and purified by reverse phase column chromatography (methanol/water) to give the target compound (15.0 mg, yield 15%) as a yellow solid compound 12.

$^1$H NMR (400 M Hz, DMSO-$d_6$): δ 13.94 (s, 1H), 10.28 (s, 1H), 10.22 (s, 1H), 8.23 (s, 1H), 7.16 (s, 1H), 4.10 (s, 2H), 2.97 (m, 2H), 2.45 (s, 3H), 2.40 (s, 3H), 1.79-1.58 (m, 5H), 1.45 (d, J=12.3 Hz, 2H), 1.26-1.18 (m, 1H).

LC-MS (ESI$^+$): m/z 351.0 (M+H)$^+$.

Example 7: Synthesis of Compounds 13 and 14

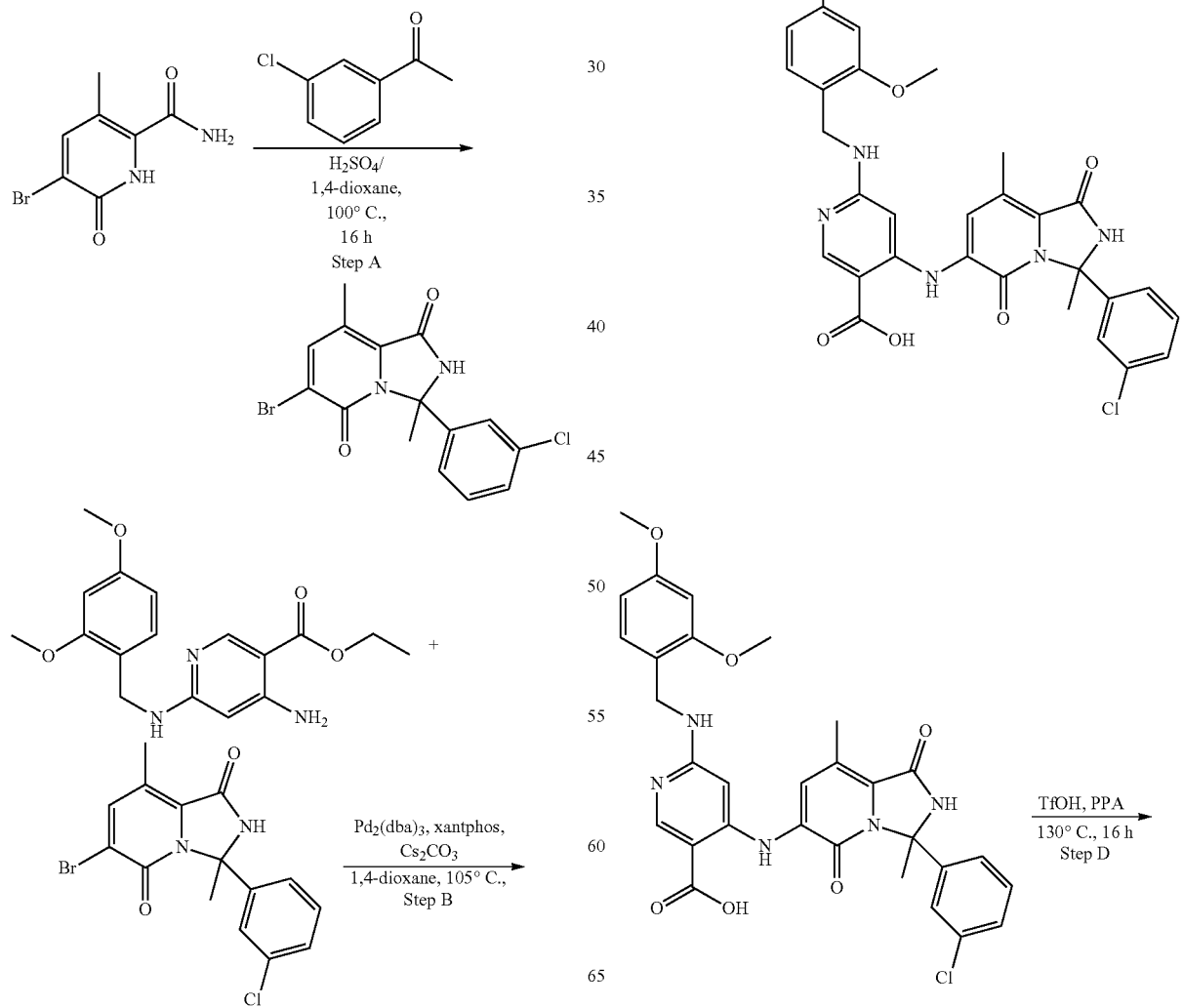

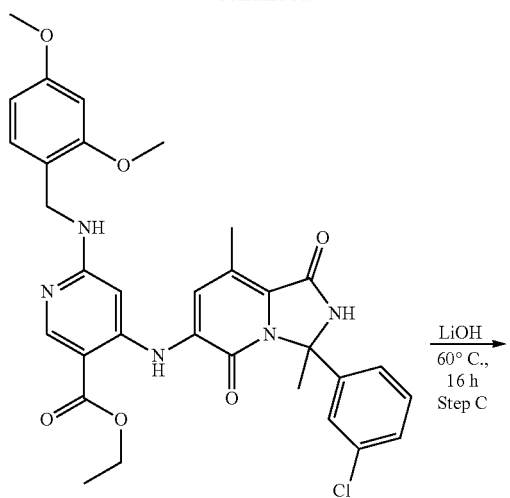

-continued

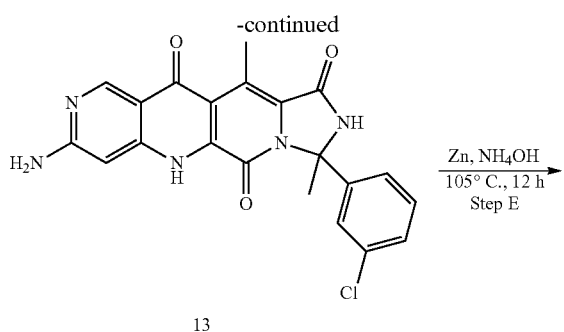

13

Zn, NH₄OH
———————→
105° C., 12 h
Step E

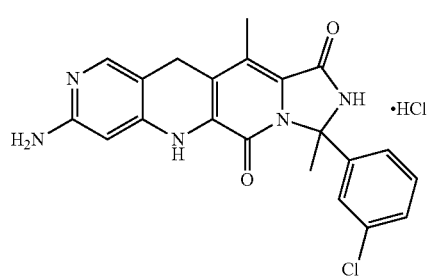

·HCl

14

Step A: 6-bromo-3-(3-chlorophenyl)-3,8-dimethyl-2,3-dihydroimidazo[1,5-a]pyridin-1,5-dione

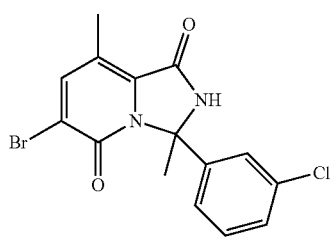 [SMILES: Cc1cc(Br)c(=O)n2c1C(=O)NC2(C)c1cccc(Cl)c1]

To a solution of 5-bromo-3-methyl-6-oxo-1,6-dihydropyridin-2-formamide (1.5 g, 6.522 mmol) in 1,4-dioxane (50 ml), 1-(3-chlorophenyl)ethan-1-one (10.1 g, 65.22 mmol) and concentrated sulfuric acid (95.9 mg, 0.978 mmol) were added at room temperature, and the reaction mixture was heated at 100° C. for 16 h. LC-MS showed that the raw materials had been completely consumed. The reaction mixture was cooled to room temperature, extracted with ethyl acetate (50 ml×2), washed with brine, dried, and concentrated under vacuum. The product was purified by column chromatography to give the desired compound (1.23 g, yield 51.5%) as a pale yellow solid.

¹H NMR (400 MHz, DMSO-d₆): δ 10.17 (s, 1H), 8.09 (s, 1H), 7.50-7.35 (m, 3H), 7.30-7.24 (m, 1H), 2.44 (s, 3H), 2.17 (s, 3H).

LC-MS (ESI⁺): m/z 367.0 369.0 (M+H)⁺.

Step B: ethyl 4-((3-(3-chlorophenyl)-3,8-dimethyl-1,5-dioxo-1,2,3,5-tetrahydro imidazo[1,5-a]pyridin-6-yl)amino)-6-((2,4-dimethoxybenzyl)amino)nicotinate

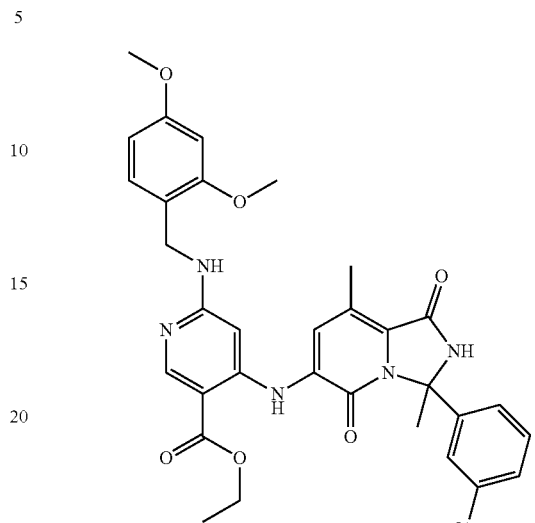

To a solution of ethyl 4-amino-6-((2,4-dimethoxybenzyl)amino)nicotinate (1.224 g, 3.696 mmol) in 1,4-dioxane (150 ml), 6-bromo-3-(3-chlorophenyl)-3,8-dimethyl-2,3-dihydroimidazo[1,5-a]pyridin-1,5-dione (1.23 g, 3.36 mmol), Pd₂(dba)₃ (461.8 mg, 0.504 mmol), xantphos (291.7 mg, 0.504 mg), cesium carbonate (2.76 g, 8.403 mmol) were added at room temperature under the protection of nitrogen. The reaction solution was replaced with nitrogen 3 times, and the reaction mixture was heated at 105° C. for 12 hours under the protection of nitrogen. TLC (petroleum ether/ethyl acetate=2/1, silica gel plate) indicated that the raw materials had been completely consumed. The reaction mixture was cooled to room temperature and poured into water (30 ml), and a yellow solid was formed. The yellow solid was separated by filtration and washed with ethyl acetate (10 ml×2) and water (10 ml×2). The solid was dried under vacuum to give the desired compound (700.1 mg, yield 33.8%) as a yellow solid.

LC-MS (ESI⁺): m/z 618.4 (M+H)⁺.

Step C: 4-((3-(3-chlorophenyl)-3,8-dimethyl-1,5-dioxo-1,2,3,5-tetrahydroimidazole[1,5-a]pyridin-6-yl)amino)-6-((2,4-dimethoxybenzyl)amino)nicotinic acid

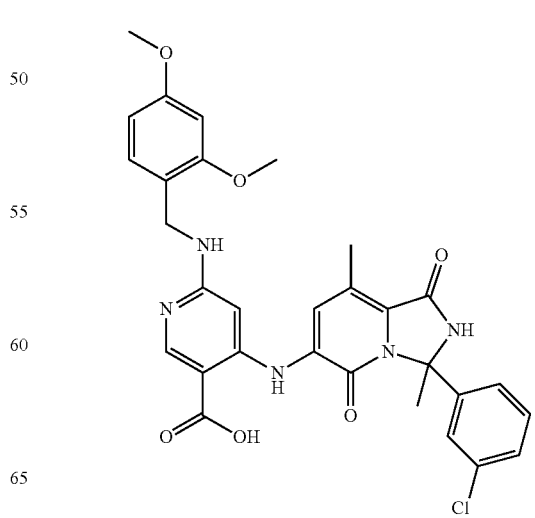

At room temperature, ethyl 4-((3-(3-chlorophenyl)-3,8-dimethyl-1,5-dioxo-1,2,3,5-tetrahydroimidazo[1,5-a]pyridin-6-yl)amino)-6-((2,4-dimethoxybenzyl)amino)nicotinate (700 mg, 1.135 mmol) was dissolved in tetrahydrofuran (90 ml) and ethanol (10 ml), followed by addition of lithium hydroxide (476.5 mg, 11.35 mmol) and deionized water (10 ml). The reaction was heated at 60° C. for 12 hours. TLC (dichloromethane/methanol=10/1, silica gel plate) indicated that the raw materials had been completely consumed. The mixture was concentrated under vacuum and dissolved in water (100 ml), and the aqueous layer was washed with diethyl ether (30 ml). The aqueous layer was acidified to pH=6.0 with 1M aqueous hydrochloric acid solution to form a yellow solid. The solid was separated by filtration and dried under vacuum to give the target compound (651 mg, 97.4%) as a yellow solid.

$^1$H NMR (400 MHz, DMSO-$d_6$) δ 9.83 (s, 1H), 8.51 (s, 1H), 7.51 (dd, J=13.1, 5.9 Hz, 1H), 7.44-7.37 (m, 4H), 7.29-7.20 (m, 4H), 7.15 (d, J=8.3 Hz, 1H), 6.58 (d, J=2.4 Hz, 1H), 6.48 (dd, J=8.4, 2.3 Hz, 1H), 4.39 (d, J=4.4 Hz, 2H), 3.80 (s, 3H), 3.74 (s, 3H), 2.45 (s, 3H), 2.19 (s, 3H).

LC-MS (ESI$^+$): m/z 590.2 (M+H)$^+$.

Step D: 8-amino-3-(3-chlorophenyl)-3,12-dimethyl-2,3-dihydroimidazole[1',5':1,6]pyrido[3,4-b][1,6]naphthopyridin-1,5,11(6H)-trione (Compound 13)

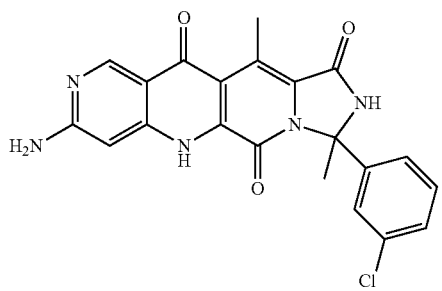 [SMILES: Cc1c2n(c(=O)c3[nH]c4cc(N)ncc4c(=O)c13)C(C)(c1cccc(Cl)c1)NC2=O]

4-((3-(3-chlorophenyl)-3,8-dimethyl-1,5-dioxo-1,2,3,5-tetrahydroimidazo[1,5-a]pyridin-6-yl)amino)-6-((2,4-dimethoxybenzyl)amino)nicotinic acid (651 mg, 1.105 mmol) was dissolved in trifluoromethanesulfonic acid and polyphosphoric acid (trifluoromethanesulfonic acid/polyphosphoric acid=5/1, 15 ml), and the mixture was heated at 130° C. for 12 hours. TLC (dichloromethane/methanol=10/1, silica gel plate) indicated that the raw materials had been completely consumed. The mixture was cooled to room temperature, and then the mixture was poured into ice water. The aqueous layer was washed with diethyl ether (50 ml), basified to pH=7.0 with 1M aqueous sodium hydroxide solution, and then extracted with a mixed solvent of dichloromethane and isopropanol (dichloromethane and isopropanol=3/1, 100 ml×8). The combined organic layers were washed with brine (50 ml×1), dried over anhydrous sodium sulfate, filtered, and concentrated under vacuum. The product was washed with ethyl acetate (10 ml×2) and then washed with methanol (10 ml×2). The obtained solid was dried under vacuum to give the target compound (398.1 mg, 85.6%) as a yellow solid compound 13.

$^1$H NMR (400 MHz, DMSO-$d_6$) δ 11.44 (s, 1H), 9.95 (s, 1H), 8.79 (s, 1H), 7.53 (s, 1H), 7.50-7.29 (m, 3H), 6.69 (s, 2H), 6.51 (d, J=11.1 Hz, 1H), 3.00 (s, 3H), 2.23 (s, 3H).

LC-MS (ESI$^+$): m/z 422.0 (M+H)$^+$.

Step E: 8-amino-3-(3-chlorophenyl)-3,12-dimethyl-2,3,6,11-tetrahydroimidazole[1',5':1,6]pyrido[3,4-b][1,6]naphthyridine-1,5-dione hydrochloride (Compound 14)

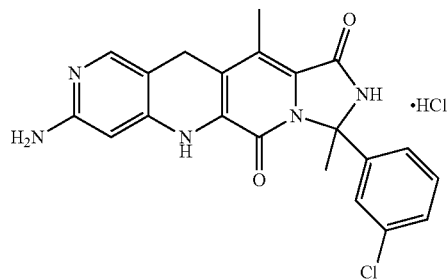 [SMILES: Cc1c2c(c(=O)n3c1C(=O)NC3(C)c1cccc(Cl)c1)Nc1cc(N)ncc1C2 ; Cl]

In a 250 ml sealed tube, zinc powder (310.7 mg, 4.75 mmol) was added to a mixed solution of 8-amino-3-(3-chlorophenyl)-3,12-dimethyl-2,3-dihydroimidazo[1',5':1,6]pyrido[3,4-b][1,6]naphthyridine-1,5,11(6h)-trione (200 mg, 0.475 mmol) and ammonia water (50 ml). The reactants were stirred at 105° C. for 12 hours. TLC (dichloromethane/methanol=10/1, silica gel plate) indicated that the raw materials had been completely consumed. The reaction mixture was cooled to room temperature and concentrated under vacuum. The mixture was dissolved in tetrahydrofuran (50 ml) and methanol (50 ml) and filtered, and the filtrate was concentrated under vacuum. The product was acidified to pH=6.0 with 1 N aqueous hydrochloric acid solution, and the product was concentrated under vacuum, purified by reverse phase column chromatography (acetonitrile/water) to give the target compound 14 (25.7 mg, yield 13.3%) as a yellow solid.

$^1$H NMR (400 MHz, DMSO-$d_6$): δ 12.37 (s, 1H), 9.98 (s, 1H), 9.90 (s, 1H), 7.63 (s, 1H), 7.49-7.35 (m, 5H), 7.31 (d, J=7.1 Hz, 1H), 6.36 (s, 1H), 3.91 (s, 2H), 2.43 (s, 3H), 2.20 (s, 3H). LC-MS (ESI$^+$): m/z 408.2 (M+H)$^+$.

Example 8: Synthesis of Compounds 15 and 16

Synthesis scheme

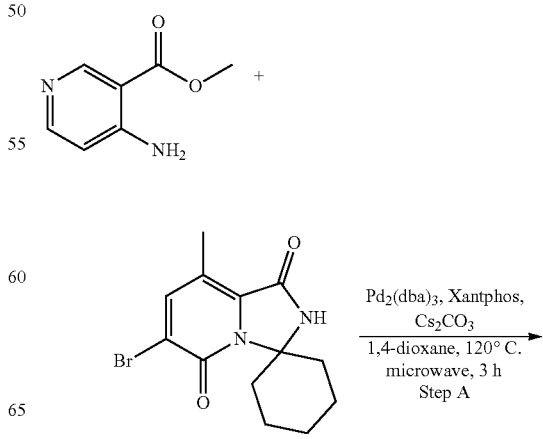

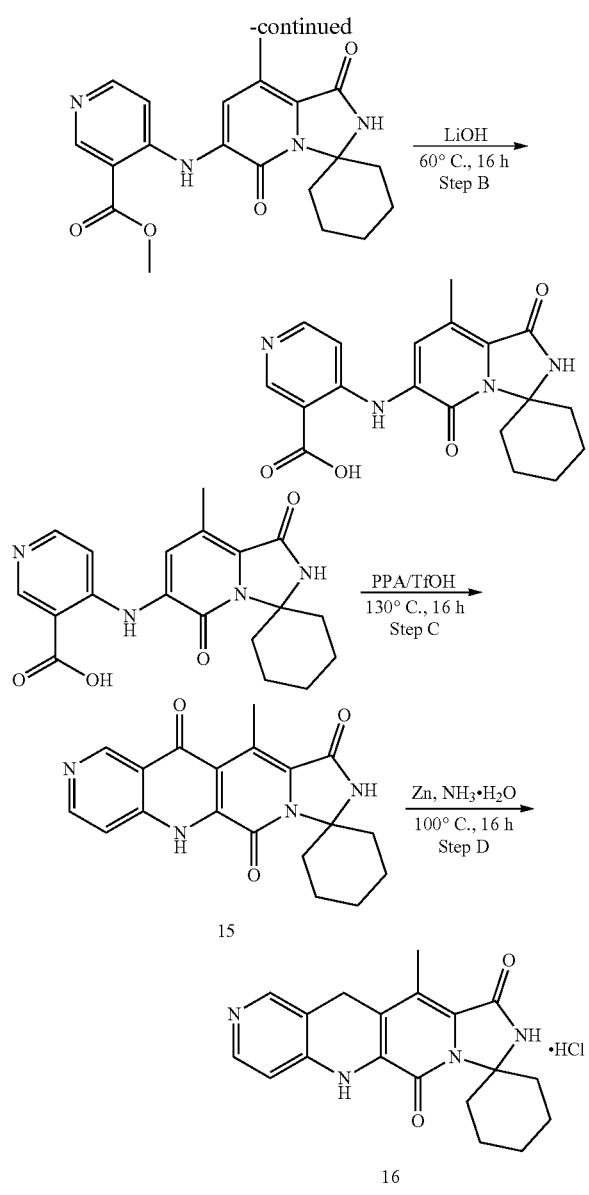

15

16

Step A: methyl 4-((8'-methyl-1',5'-dioxo-2',5'-dihydro-1'H-spiro[cyclohexane-1,3'-imidazo[1,5-a]pyridine]-6'-yl)amino)nicotinate

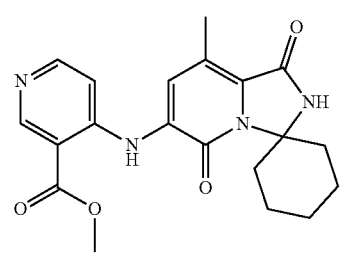 [SMILES: COC(=O)c1cnccc1Nc1cc(C)c2n(c1=O)C1(CCCCC1)NC2=O]

The raw materials, methyl 4-aminonicotinate (500 mg, 3.29 mmol), 6-bromo-8-methyl-1H-spiro[cyclohexane-1,3-imidazo[1,5-a]pyridine]-1,5 (2H)-dione (1.02 g, 3.29 mmol), Pd$_2$(dba)$_3$ (300 mg, 0.33 mmol), Xantphos (380 mg, 0.66 mmol) and cesium carbonate (2.15 g, 6.58 mmol) were mixed in 1,4-dioxane (15 ml), and after being replaced with nitrogen, the reaction was heated under microwave conditions at 120° C. for 6 hours. LC-MS detection showed that the raw materials had been completely converted into products. The reaction solution was poured into a mixture of ethyl acetate (50 ml) and water (100 ml). Then the mixture was filtered, and the filter cake was evacuated to dryness and subjected to water removal with toluene twice to give a yellow solid product (1.16 g, yield 92%).

LC-MS (ESI$^+$): m/z 383.0 (M+H)$^+$.

Step B: 4-((8-methyl-1,5-dioxo-2,5-dihydro-1H-spiro[cyclohexane-1,3-imidazo[1,5-a]pyridine]-6-yl)amino)nicotinic acid

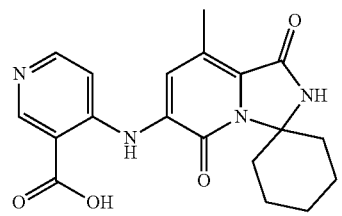 [SMILES: Cc1cc(Nc2ccncc2C(=O)O)c(=O)n2c1C(=O)NC21CCCCC1]

Methyl 4-((8-methyl-1,5-dioxo-2,5-dihydro-1H-spiro[cyclohexane-1,3-imidazo[1,5-a]pyridine]-6-yl)amino)nicotinate (1.34 g, 3.5 mmol) and lithium hydroxide monohydrate (600 mg, 14.0 mmol) were mixed in tetrahydrofuran (70 ml), methanol (20 ml) and water (40 ml) at room temperature. The reaction was heated at 65° C. for 18 hours. LC-MS showed complete conversion. The organic solvent was removed by rotary evaporation. The remaining aqueous phase was extracted with dichloromethane (40 ml). Then the aqueous layer was acidified to pH=4 with 4 mol/L hydrochloric acid solution. The mixture was filtered, and the filter cake was dried to give the product (1.1 g, yield 85%) as a yellow solid.

LC-MS (ESI$^+$): m/z 369.0 (M+H)$^+$.

Step C: 12'-methyl-1'H-spiro[cyclohexane-1,3'-imidazo[1',5':1,6]pyrido[3,4-b][1,6]naphthyridine]-1',5',11'(2'H,6'H)-trione (Compound 15)

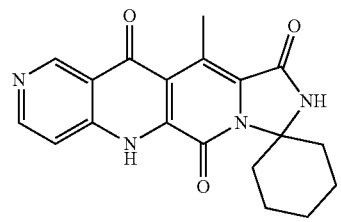 [SMILES: Cc1c2n(c(=O)c3[nH]c4ccncc4c(=O)c13)C1(CCCCC1)NC2=O]

4-((8-Methyl-1,5-dioxo-2,5-dihydro-1H-spiro[cyclohexane-1,3-imidazo[1,5-a]pyridine]-6-yl)amino)nicotinic acid (400 mg, 1.09 mmol) was mixed in trifluoromethanesulfonic acid and polyphosphoric acid (trifluoromethanesulfonic acid/polyphosphoric acid=5/1, 10 ml), and the mixture was stirred at 130° C. for 40 hours. LC-MS showed that the raw materials had been completely consumed. The reaction solution was cooled to room temperature, and poured into ice water (10 ml) and methanol (10 ml). The mixture was poured into a saturated sodium carbonate solution (80 ml), and extracted with a mixed solvent of dichloromethane and isopropanol (dichloromethane and isopropanol=3/1, 80 ml×6). The extracts were combined, dried over anhydrous sodium sulfate, and concentrated under vacuum. The residue was stirred in dichloromethane/methanol (30 ml/1.5 ml) for 1 hour, and then the mixture was filtered. The filter cake was dried to give the product compound 15 (350 mg, yield 91%) as a yellow solid.

$^1$H NMR (400 MHz, DMSO-d$_6$): δ 12.70 (s, 1H), 10.39 (s, 1H), 9.31 (s, 1H), 8.74 (d, J=6.4 Hz, 1H), 8.14 (d, J=6.4 Hz, 1H), 2.97 (m, 5H), 1.87-1.62 (m, 5H), 1.54 (d, J=11.8 Hz, 2H), 1.31-1.20 (m, 1H).

LC-MS (ESI$^+$): m/z 351.0 (M+H)$^+$.

Step D: 12-methyl-6,11-dihydro-1H-spiro[cyclohexane-1,3-imidazo[1,5:1,6]pyrido[3,4-b][1,6]naphthyridine]-1,5(2H)-dione hydrochloride (Compound 16)

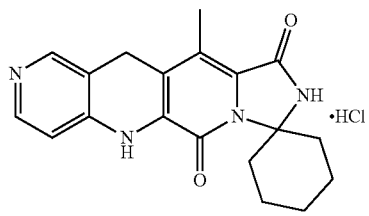 [SMILES: Cc1c2c(c(=O)n3c1C(=O)NC31CCCCC1)Nc1ccncc1C2 ; Cl]

12'-methyl-1'H-spiro[cyclohexane-1,3'-imidazo[1',5':1,6]pyrido[3,4-b][1,6]naphthyridine]-1',5',11'(2'H,6'H)-trione (200 mg, 0.0.573 mmol) and zinc powder (372.5 mg, 5.73 mmol) were mixed in ammonia water (40 ml). The reaction was heated and stirred at 105° C. for 16 hours in a sealed tube. LC-MS detection showed that the raw materials had been completely consumed. The reaction mixture was concentrated to dryness. The crude product was dissolved in 4M hydrochloric acid in methanol (10 ml) and then concentrated under vacuum. The product was purified by reverse phase column chromatography (acetonitrile/water) to give the target compound 16 (16.5 mg, yield 8.6%) as a yellow solid.

$^1$H NMR (400 MHz, DMSO-d$_6$): δ 13.93 (s, 1H), 10.40 (s, 1H), 10.23 (s, 1H), 8.31 (s, 1H), 8.27 (d, J=6.8 Hz, 1H), 7.36 (d, J=6.7 Hz, 1H), 4.15 (s, 2H), 2.96 (t, J=11.1 Hz, 2H), 2.40 (s, 3H), 1.81-1.57 (m, 5H), 1.45 (d, J=11.9 Hz, 2H), 1.29-1.14 (m, 1H).

LC-MS (ESI$^+$): m/z 337.0 (M+H)$^+$.

Example 9: Synthesis of Compounds 17 and 18

Synthesis scheme

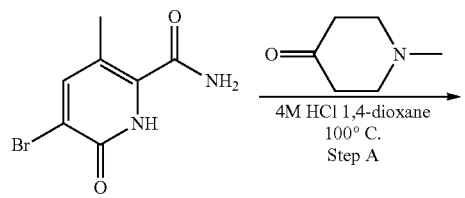

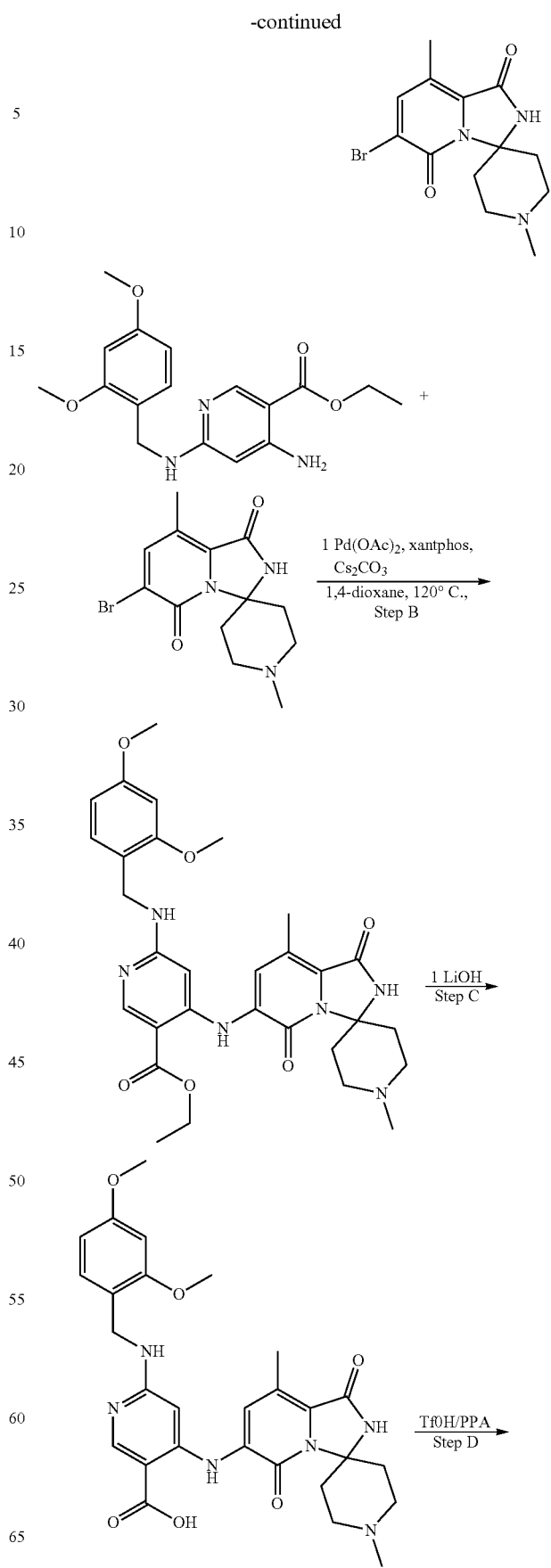

-continued

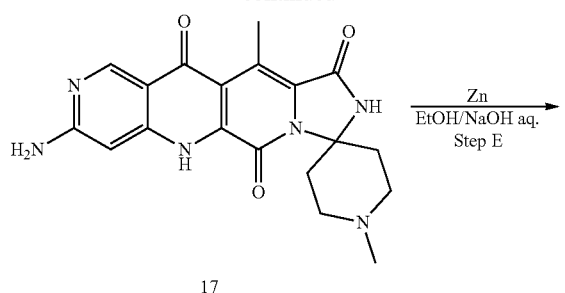

17

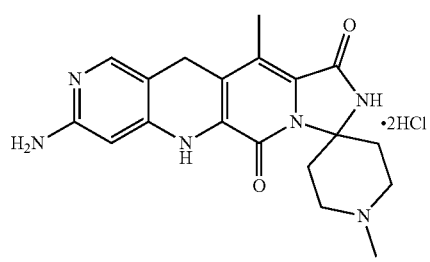

18

Step A: 6-bromo-1',8-dimethyl-2H-spiro[imidazo[1,5-a]pyridin-3,4'-piperidine]-1,5-dione

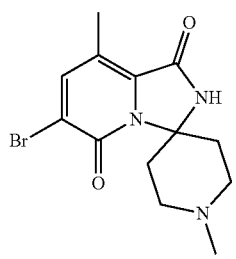 [SMILES: Cc1cc(Br)c(=O)n2c1C(=O)NC21CCN(C)CC1]

In a sealed tube, to anhydrous 1,4-dioxane (8 ml), 5-bromo-3-methyl-6-oxo-1,6-dihydropyridin-2-formamide (800 mg 3.48 mmol), 1-methylpiperidin-4-one (472 mg, 4.17 mmol) and hydrochloric acid in dioxane (4 M, 8 ml) were added at room temperature, and heated to 110° C. and reacted in the sealed tube for 16 hours. LC-MS showed that the starting materials had been completely consumed. The reaction solution was concentrated under reduced pressure. The concentrated crude product was purified by silica gel column chromatography (dichloromethane/methanol=10/1) to give the yellow target product (1 g, yield 88.2%).

LC-MS (ESI⁺): m/z 326.0 (M+H)⁺.

Step B: ethyl 6-((2,4-dimethoxybenzyl)amino)-4-((1',8-dimethyl-1,5-dioxo-1,5-dihydro-2H-spiro[imidazo[1,5-a]pyridin-3,4'-piperidyl]-6-yl)amino)nicotinate

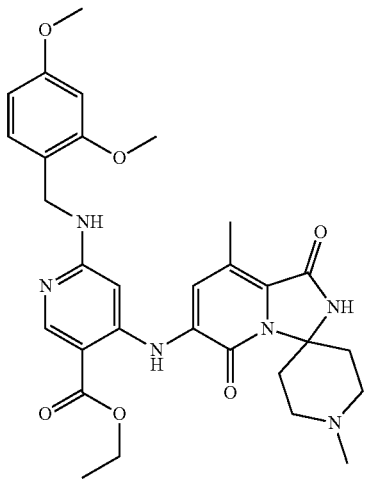 [SMILES: CCOC(=O)c1cnc(NCc2ccc(OC)cc2OC)cc1Nc1cc(C)c2n(c1=O)C1(CCN(C)CC1)NC2=O]

To anhydrous 1,4-dioxane (13 ml), 6-bromo-1',8-dimethyl-2H-spiro[imidazo[1,5-a]pyridin-3,4'-piperidine]-1,5-dione (700 mg, 2.15 mmol), ethyl 4-amino-6-((2,4-dimethoxybenzyl) amino)nicotinate (643.58 mg, 1.94 mmol), tris(dibenzylideneacetone) dipalladium (197.3 mg, 0.215 mmol), 4,5-bis(diphenylphosphine)-9,9-dimethylxanthene (249.3 mg, 0.43 mmol), cesium carbonate (1.407 g, 4.3 mol) were added at room temperature under anhydrous and oxygen-free conditions. The reaction solution was replaced with nitrogen three times, and the reaction mixture was reacted at 120° C. in a microwave for 4 hours under the protection of nitrogen. LC-MS indicated that the raw materials had been consumed completely. The reaction mixture was cooled to room temperature and poured into water (30 ml). A yellow solid was formed. The yellow solid was separated by filtration and washed with ethyl acetate (10 ml×2) and water (10 ml×2). The solid was dried under vacuum to give the desired compound (650 mg, yield 53.5%) as a yellow solid.

LC-MS (ESI⁺): m/z 577.4 (M+H)⁺.

Step C: 6-((2,4-dimethoxybenzyl)amino)-4-((1',8-dimethyl-1,5-dioxo-1,5-dihydro-2H-spiro[imidazo[1,5-a]pyridin-3,4'-piperidyl]-6-yl)amino)nicotinic acid

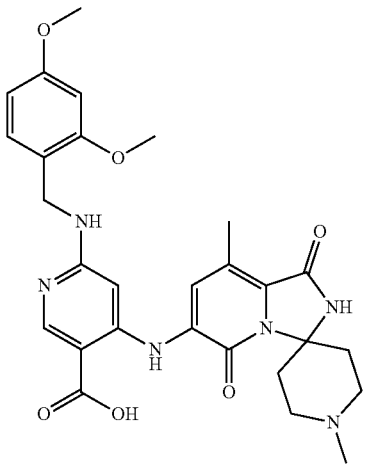 [SMILES: COc1ccc(CNc2cc(Nc3cc(C)c4n(c3=O)C3(CCN(C)CC3)NC4=O)c(C(=O)O)cn2)c(OC)c1]

To tetrahydrofuran (100 ml), ethyl 6-((2,4-dimethoxybenzyl)amino)-4-41',8-dimethyl-1,5-dioxo-1,5-dihydro-2H-spiro[imidazo[1,5-a]pyridin-3,4'-piperidyl]-6-yl)amino)nicotinate (1.3 g, 2.25 mmol), deionized water (20 ml), lithium hydroxide (567.37 mg, 13.51 mmol) were added at room temperature and then heated to 65° C. and stirred for 16 hours. LC-MS indicated that the raw materials had been completely consumed. The mixture was cooled to room temperature and filtered. The filtrate was adjusted to pH=7 with 1M hydrochloric acid solution to form a yellow solid. The solid was separated by filtration and dried under vacuum to give the target compound (750 mg, yield 60.6%).

LC-MS (ESI$^+$): m/z 549.4 (M+H)$^+$.

Step D: 8-amino-1',12-dimethyl-2H-spiro[imidazo[1',5':1,6]pyrido[3,4-B][1,6]naphthyridine-3,4'-piperidine]-1,5,11(6H)-trione (Compound 17)

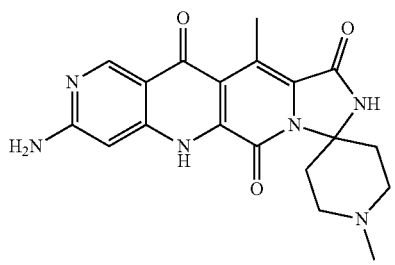 [SMILES: Cc1c2n(c(=O)c3[nH]c4cc(N)ncc4c(=O)c13)C1(CCN(C)CC1)NC2=O]

6-((2,4-Dimethoxybenzyl)amino)-4-((1',8-dimethyl-1,5-dioxo-1,5-dihydro-2H-spiro[imidazo[1,5-a]pyridin-3,4'-piperidyl]-6-yl)amino)nicotinic acid (700 mg, 1.277 mmol) was dissolved in trifluoromethanesulfonic acid and polyphosphoric acid (trifluoromethanesulfonic acid/polyphosphoric acid=5/1, 25 ml), heated to 130° C., and reacted under stirring for 16 hours. LC-MS showed that the starting materials had been completely consumed. The mixture was cooled to normal temperature, poured into ice water, and adjusted to pH=7 with a saturated sodium carbonate solution. Precipitation of insoluble solid was observed. The mixture was filtered, and the filter cake was purified by reverse phase column chromatography (methanol/water) to give the target compound 17 (198.4 mg, yield 40.91%) as a green solid.

LC-MS (ESI$^+$): m/z 381.4 (M+H)$^+$.

$^1$H NMR (400 MHz, DMSO-d$_6$) δ 11.71 (s, 1H), 9.99 (s, 1H), 8.81 (s, 1H), 7.18 (s, 2H), 6.80 (s, 1H), 3.66 (d, J=11.1 Hz, 2H), 3.42 (t, 2H), 3.34-3.24 (m, 2H), 2.95 (s, 3H), 2.81 (s, 3H), 1.89 (d, J=12.8 Hz, 2H).

Step E: 8-amino-1',12-dimethyl-6,11-dihydro-2H-spiro[imidazo[1',5':1,6]pyrido[3,4-b][1,6]naphthyridine-3,4'-piperidine]-1,5-dione (Compound 18)

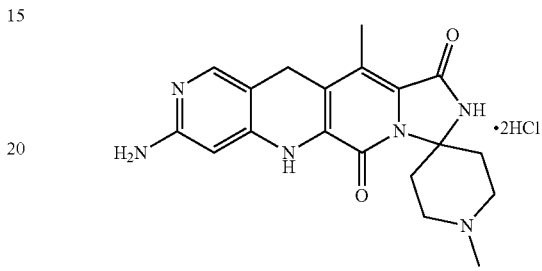

To a solution of 8-amino-1',12-dimethyl-2H-spiro[imidazo[1',5':1,6]pyrido[3,4-B][1,6]naphthyridine-3,4'-piperidine]-1,5,11(6H)-trione (100 mg, 0.263 mmol) in ethanol (5 ml), zinc powder (336.8 mg, 5.263 mmol) and sodium hydroxide solution (1 M, 5 ml) were added at room temperature. The reaction solution was heated to 78° C. and stirred for 16 hours. LC-MS indicated that the raw materials had been completely consumed. The reaction mixture was cooled to room temperature and filtered, and the filtrate was adjusted to pH=5 with 1M hydrochloric acid solution, and concentrated under vacuum. The crude product was purified by reverse phase column chromatography (methanol/water) to give the title compound (2.5 mg, yield 2.5%) as a yellow solid.

LC-MS (ESI$^+$): m/z 367.2 (M+H)$^+$.

$^1$H NMR (400 MHz, DMSO-d$_6$) δ 12.56 (s, 1H), 10.29 (s, 1H), 9.96 (s, 2H), 7.65 (s, 1H), 7.46 (s, 2H), 6.49 (s, 1H), 3.90 (s, 2H), 3.64 (d, J=11.1 Hz, 2H), 3.46-3.37 (m, 2H), 3.31-3.21 (m, 2H), 2.80 (s, 3H) 2.39 (s, 3H),1.82 (d, J=12.8 Hz, 2H).

Example 10: Synthesis of Compound 19

Synthesis scheme

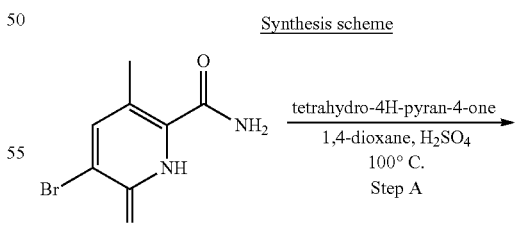

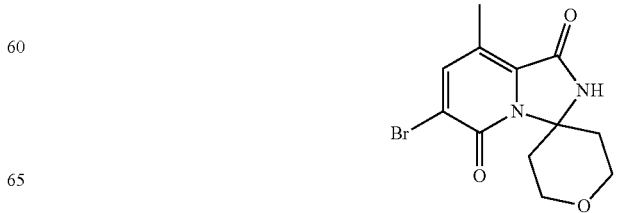

79

-continued

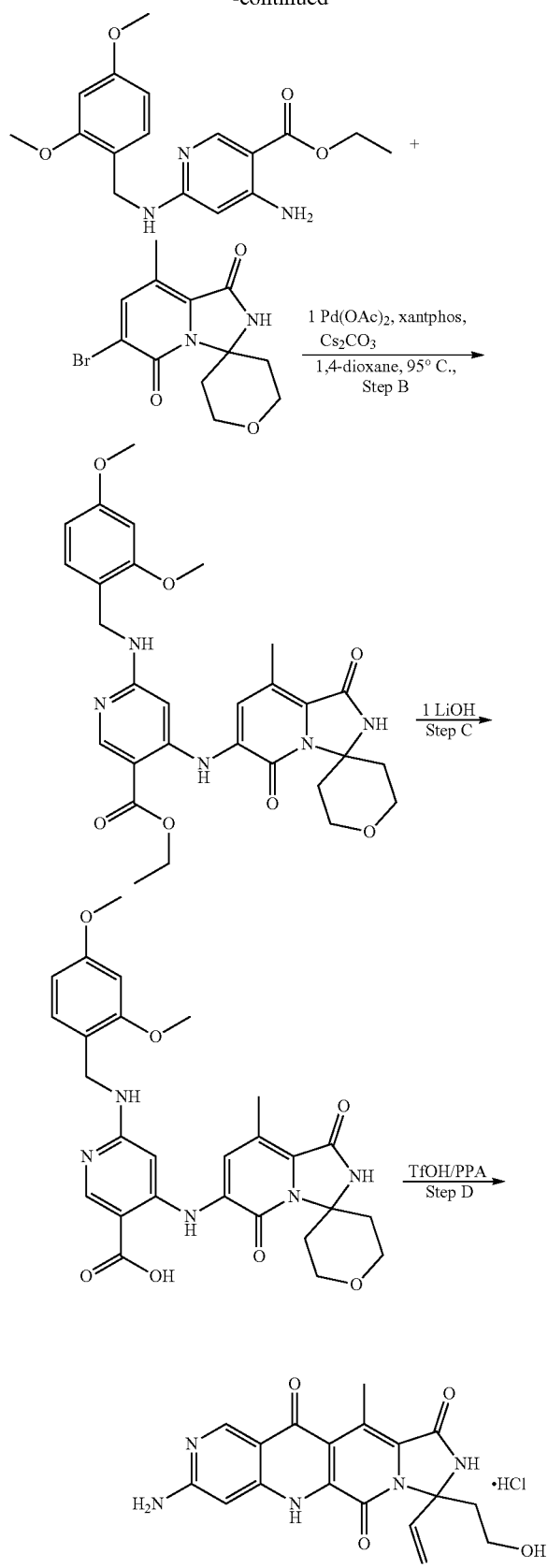

80

Step A: 6-bromo-8-methyl-2',3',5',6'-tetrahydro-2H-spiro[imidazo[1,5-a]pyridin-3,4'-pyran]-1,5-dione To a solution of 5-bromo-3-methyl-6-oxo-1,6-dihydropyridin-2-formamide (1.5 g, 6.522 mmol) in 1,4-dioxane (50 ml), tetrahydro-4H-pyran-4-one (6.52 g, 65.22 mmol) and concentrated sulfuric acid (95.9 mg, 0.978 mmol) were added at room temperature, and the reaction mixture was heated at 100° C. for 16 hours. LC-MS showed that the raw materials had been completely consumed. The reaction mixture was cooled to room temperature, extracted with ethyl acetate (50 ml×2), washed with brine, dried, and concentrated under vacuum. The product was purified by column chromatography to give the desired compound (1.31 g, yield 64.4%) as a white solid.

LC-MS (ESI$^+$): m/z 313.0 (M+H)$^+$.

$^1$H NMR (400 MHz, DMSO-d$_6$): δ 10.63 (s, 1H), 8.05 (s, 1H), 3.92 (dd, J=11.7, 5.1 Hz, 2H), 3.66 (t, J=11.8 Hz, 2H), 3.17 (td, J=13.0, 5.4 Hz, 2H), 2.39 (s, 3H), 1.43 (d, J=12.8 Hz, 2H).

Step B: ethyl 64(2,4-dimethoxybenzyl)amino)-4-((8-methyl-1,5-dioxo-1,2',3',5,5',6% hexahydro-2H-spiro[imidazo[1,5-a]pyridin-3,4'-pyran]-6-yl)amino) nicotinate To a solution of ethyl 4-amino-6-((2,4-dimethoxybenzyl) amino)nicotinate (1.05 g, 3.17 mmol) in 1,4-dioxane (150 ml), 6-bromo-8-methyl-2',3',5',6'-tetrahydro-2H-spiro[imidazo[1,5-a]pyridin-3,4'-pyran]-1,5-dione (900 mg, 2.885 mmol), Pd$_2$(dba)$_3$ (396.4 mg, 0.433 mmol), xantphos (250.5 mg, 0.433 mmol), cesium carbonate (2.35 g, 7.213 mmol) were added at room temperature under the protection of nitrogen. The reaction solution was replaced with nitrogen 3 times, and the reaction mixture was heated at 105° C. for 12 hours under the protection of nitrogen. TLC (petroleum ether/ethyl acetate=2/1, silica gel plate) indicated that the raw materials had been completely consumed. The reaction mixture was cooled to room temperature and poured into water (30 ml). A yellow solid was formed. The yellow solid was separated by filtration and washed with ethyl acetate (10 ml×2) and water (10 ml×2). The solid was dried under vacuum to give the desired compound (850 mg, yield 55.4%) as a yellow solid.

LC-MS (ESI⁺): m/z 564.0 (M+H)⁺.

¹H NMR (400 MHz, DMSO-$d_6$): δ 11.14 (s, 1H), 10.31 (s, 1H), 8.55 (s, 1H), 7.34 (s, 1H), 7.30-7.22 (m, 1H), 7.16 (d, J=8.3 Hz, 1H), 6.66-6.53 (m, 2H), 6.48 (dd, J=8.4, 2.3 Hz, 1H), 4.40 (d, J=4.8 Hz, 2H), 3.92 (dd, J=11.5, 5.0 Hz, 2H), 3.80 (s, 3H), 3.74 (s, 3H), 3.72-3.62 (m, 2H), 3.44 (dd, J=14.0, 7.0 Hz, 2H), 3.24 (td, J=12.7, 5.0 Hz, 2H), 2.41 (s, 3H), 1.39 (t, J=13.8 Hz, 2H), 1.06 (t, J=7.0 Hz, 3H).

Step C: 64(2,4-dimethoxybenzyl)amino)-4-((8-methyl-1,5-dioxo-1,2',3',5,5',6'-hexahydro-2H-spiro [imidazo[1,5-a]pyridin-3,4'-pyran]-6-yl)amino)nicotinic acid

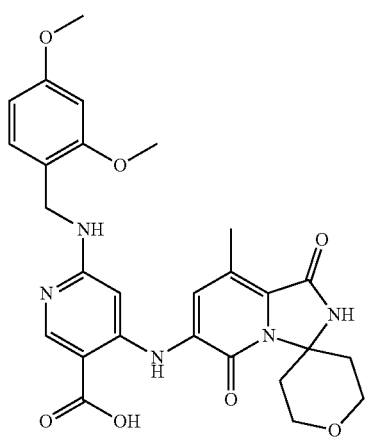 [SMILES: COc1ccc(CNc2cc(Nc3cc(C)c4n(c3=O)C3(CCOCC3)NC4=O)c(C(=O)O)cn2)c(OC)c1]

Ethyl 64(2,4-dimethoxybenzyl)amino)-4-((8-methyl-1,5-dioxo-1,2',3',5,5',6'-hexahydro-2H-spiro[imidazo[1,5-a] pyridin-3,4'-pyran]-6-yl)amino)nicotinate (850 mg, 1.51 mmol) was dissolved in tetrahydrofuran (90 ml) and ethanol (10 ml) at room temperature, followed by addition of lithium hydroxide (317.1 mg, 7.55 mmol) and deionized water (10 ml). The reaction was heated at 60° C. for 12 hours. TLC (dichloromethane/methanol=10/1, silica gel plate) indicated that the raw materials had been completely consumed. The mixture was concentrated under vacuum and dissolved in water (100 ml), and the aqueous layer was washed with diethyl ether (30 ml). The aqueous layer was acidified to pH=6.0 with 1M aqueous hydrochloric acid solution to form a yellow solid. The solid was separated by filtration and dried under vacuum to give the target compound (755 mg, 93.5%) as a yellow solid.

LC-MS (ESI⁺): m/z 536.2 (M+H)⁺.

Step D: 8-amino-3-(2-hydroxyethyl)-12-methyl-3-ethenyl-2,3-dihydroimidazo[1',5':1,6]pyrido[3,4-b] [1,6]naphthyridine-1,5,11(6H)-trione (Compound 19)

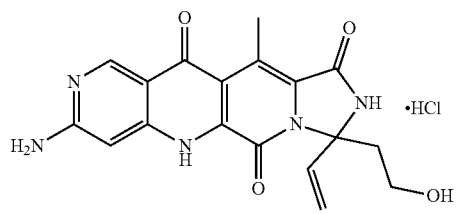 [SMILES: C=CC1(CCO)NC(=O)c2c(C)c3c(=O)c4cnc(N)cc4[nH]c3c(=O)n21 ; Cl]

6-((2,4-Dimethoxybenzyl)amino)-4-((8-methyl-1,5-dioxo-1,2',3',5,5',6'-hexahydro-2H-spiro[imidazo[1,5-a]pyridin-3,4'-pyran]-6-yl)amino)nicotinic acid (450 mg, 0.841 mmol) was dissolved in trifluoromethanesulfonic acid and polyphosphoric acid (trifluoromethanesulfonic acid/polyphosphoric acid=5/1, 15 ml), and the mixture was heated at 130° C. for 12 hours. TLC (dichloromethane/methanol=10/1, silica gel plate) indicated that the raw materials had been completely consumed. The mixture was cooled to room temperature, and then the mixture was poured into ice water. The aqueous layer was washed with diethyl ether (50 ml), basified to pH=7.0 with 1M aqueous sodium hydroxide solution, and then extracted with a mixed solvent of dichloromethane and isopropanol (dichloromethane and isopropanol=3/1, 100 ml×8). The combined organic layers were washed with brine (50 ml×1), dried over anhydrous sodium sulfate, filtered, and concentrated under vacuum. The obtained concentrate was purified by reverse phase column chromatography (acetonitrile/water) to give compound 19 (28.1 mg, yield 9.1%) as a yellow solid.

LC-MS (ESI⁺): m/z 368.0 (M+H)⁺.

¹H NMR (400 MHz, DMSO-$d_6$) δ 11.84 (s, 1H), 9.81 (s, 1H), 8.80 (s, 1H), 7.36 (s, 1H), 7.27 (s, 1H), 7.14 (s, 1H), 7.01 (s, 1H), 6.83 (s, 1H), 6.58 (dd, J=17.3, 10.5 Hz, 1H), 5.45 (d, J=17.3 Hz, 1H), 5.32 (d, J=10.6 Hz, 1H), 3.45-3.30 (m, 2H), 2.92 (s, 3H), 2.86-2.74 (m, 1H), 2.28-2.18 (m, 1H).

Example 11: Synthesis of Compound 20

Synthesis scheme

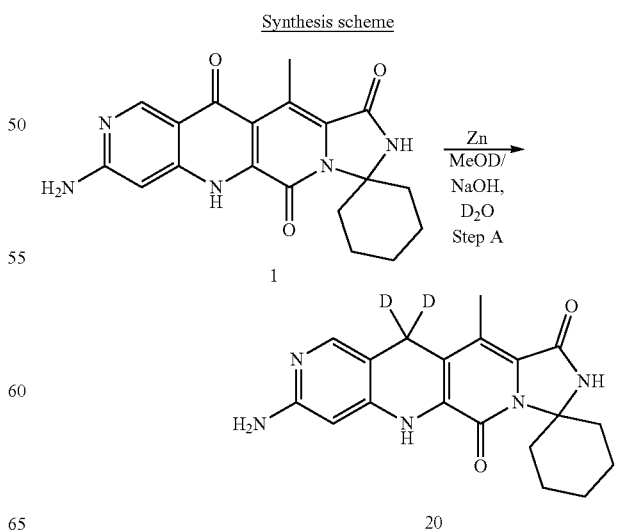

Step A: 8'-amino-12'-methyl-6',11'-dihydro-2'H-spiro[cyclohexane-1,3'-imidazo[1',5':1,6]pyrido[3,4-b][1,6]naphthyridine]-1',5'-dione-11',11'-d2 hydrochloride (Compound 20)

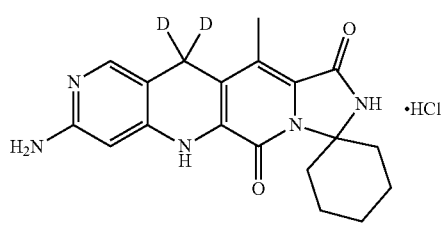 [SMILES: [2H]C1([2H])c2cnc(N)cc2Nc2c1c(C)c1n(c2=O)C2(CCCCC2)NC1=O ; Cl]

8'-Amino-12'-methyl-2'H-spiro[cyclohexane-1,3'-imidazo[1',5': 1,6]pyrido[3,4-b][1,6]naphthyridine]-1',5',11' (6'H)-trione (compound 1) (100 mg, 0.27 mmol) and zinc powder (180 mg, 2.74 mmol) were mixed in sodium hydroxide (1M heavy water solution, 2 ml) and deuterated methanol (2 ml) at room temperature. The reaction solution was heated and stirred at 70° C. for 16 hours. LC-MS detection of the reaction showed that a product was formed and very little raw material remained. The reaction solution was cooled to room temperature and filtered. The filtrate was added with a solution of hydrogen chloride in methanol (4M, 15 ml) to pH=3.0, and concentrated to dryness with a rotary evaporator. The resulting crude product was purified by medium-pressure reverse phase column chromatography (methanol/deionized water) to give the target compound 20 (18.9 mg, yield 19%) as a yellow solid.

LC-MS (ESI+): m/z 354.2 (M+H)+.

1H NMR (400 MHz, DMSO-d6): δ 12.30 (s, 1H), 10.15 (s, 1H), 9.98 (s, 1H), 7.64 (s, 1H), 7.36 (s, 2H), 6.46 (s, 1H), 3.02-2.94 (m, 2H), 2.39 (s, 3H), 1.77-1.58 (m, 5H), 1.44 (d, J=12.4 Hz, 2H), 1.27-1.15 (m, 1H).

Example 12: Synthesis of Compound 21

Synthesis scheme

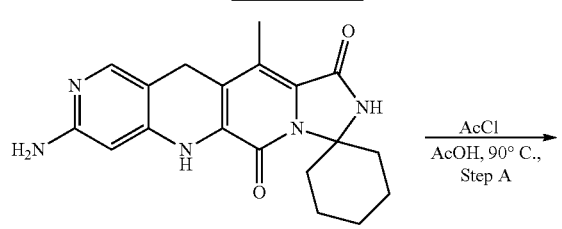

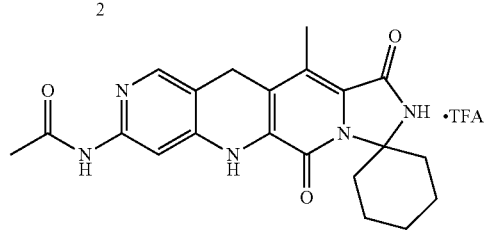

Step A: 12(N-methyl-1,5-2,5,6,11-tetrahydro-1H-spiro[cyclohexane-1-imidazo[1,5-6]pyrido[3,4-b]naphthyridine1.6][8]'-yl)acetamide (Compound 21)

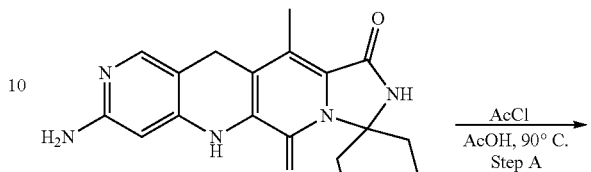

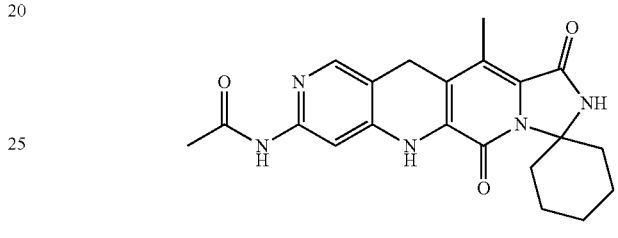

Acetyl chloride (44 mg, 0.569 mmol) was added in a solution of 8'-amino-12'-methyl-6',11'-dihydro-2'H-spiro[cyclohexane-1,3'-imidazo[1',5':1,6]pyrido[3,4-b][1,6]naphthyridine]-1',5'-dione (100 mg, 0.284 mmol) in acetic acid (8 ml) at room temperature. The reaction mixture was heated to 90° C. and stirred overnight. After completion of the reaction detected by TLC, the reaction solution was spin-dried, acidified with a solution of hydrogen chloride in dioxane and concentrated again. The crude product was separated and purified by reverse phase chromatographic column to give the product (5 mg, yield 4.46%).

LC-MS (ESI+): m/z 394.2 (M+H)+.

1H NMR (400 MHz, DMSO-d6): δ 11.46 (s, 1H), 10.16 (s, 2H), 7.91 (s, 1H), 7.09 (s, 1H), 4.05 (s, 2H), 2.97 (t, J=11.3 Hz, 2H), 2.40 (s, 3H), 2.16 (s, 3H), 1.69-1.51 (m, 5H), 1.45-1.42 (m, 2H), 1.21-1.25 (m, 1H).

Example 13: Synthesis of Compound 22

Synthesis scheme

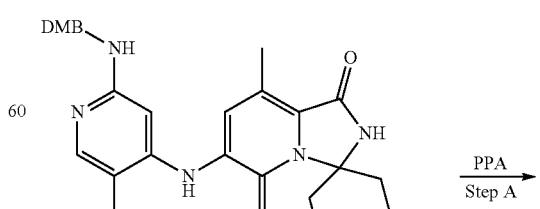

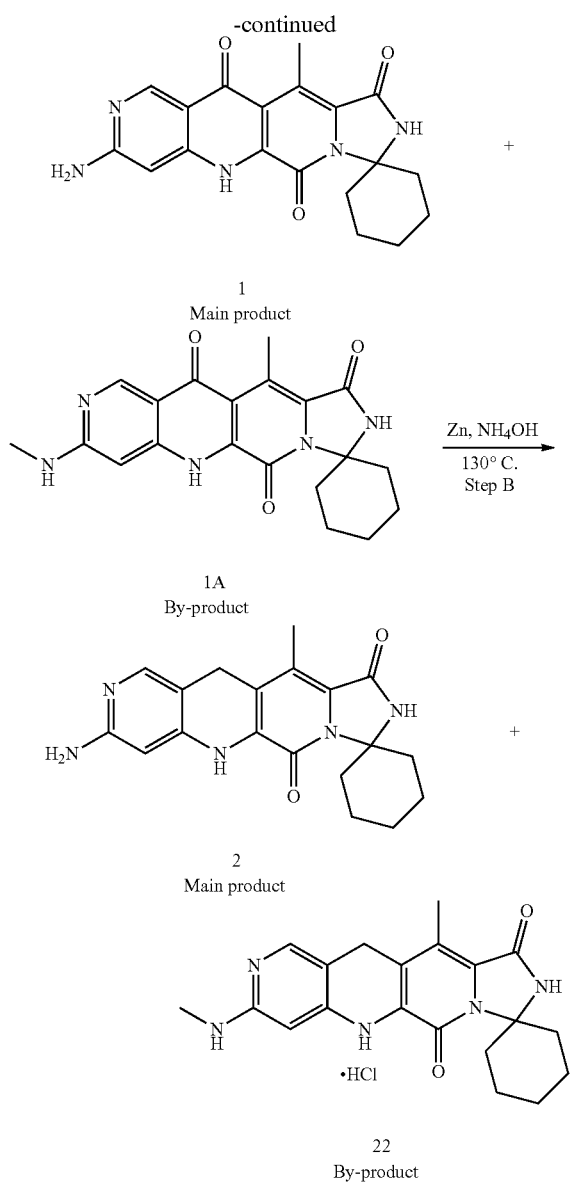

Step A: 12'-methyl-8'-(methylamino)-1'H-spiro[cyclohexane-1,3'-imidazo[1',5':1,6]pyrido[3,4-b][1,6]naphthyridine]-1',5',11'(2'H,6'H)-trione (Compound 1A)

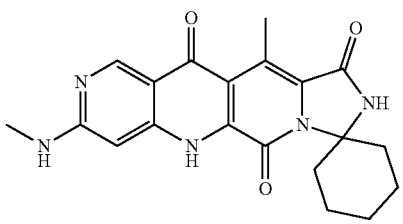 [SMILES: CNc1cc2[nH]c3c(=O)n4c(c(C)c3c(=O)c2cn1)C(=O)NC41CCCCC1]

6-((3,4-Dimethoxybenzyl) amino)-4-((8'-methyl-,5'-dioxo-1',5'-dihydro-2'H-spiro[cyclohexane-1,3'-imidazo[1,5-a]pyridine]-6'-yl)amino)nicotinic acid (22 g, 41.2 mmol) was mixed in a mixed solution of polyphosphoric acid and trifluoromethanesulfonic acid (polyphosphoric acid/trifluoromethanesulfonic acid=1:5, 160 ml), and the reaction mixture was heated and stirred at 130° C. for 16 hours. LC-MS detection of the reaction showed that the raw materials had been completely consumed, and the main product was compound 1, and the by-product was compound 1A. The mixture was cooled to room temperature and then slowly poured into ice water to quench, followed by addition of a saturated sodium carbonate solution (1.5 liters), and then 1.5 liters of water. The resulting mixture was extracted with a mixed solvent of dichloromethane and isopropanol (dichloromethane and isopropanol=3/1, 2 liters×8), and the extracts were combined, dried over anhydrous sodium sulfate, filtered, and concentrated with a rotary evaporator to complete dryness. The crude product was added with dichloromethane (150 ml) and methanol (15 ml), stirred at room temperature for 10 minutes, and filtered. Then the filter cake was stirred in 150 ml of water for 10 minutes and filtered, and the filter cake was dried under vacuum to give a mixture of the main product compound 1 and the by-product 1A (12 g, crude, with a content of 1A being about 20%) as a yellow-green solid.

Compound 1A: LC-MS (ESI$^+$): m/z 380.2 (M+H)$^+$.

Step B: 12'-methyl-8'-(methylamino)-6',11'-dihydro-1'H-spiro[cyclohexane-1,3'-imidazo[1',5':1,6]pyrido[3,4-b][1,6]naphthopyridine]-1',5'(2'H)-dione hydrochloride (Compound 22)

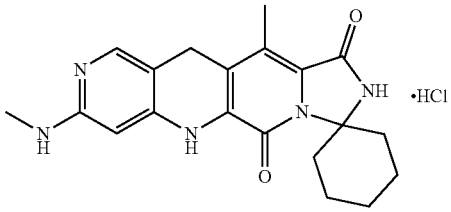 [SMILES: CNc1cc2c(cn1)Cc1c(C)c3n(c(=O)c1N2)C1(CCCCC1)NC3=O ; Cl]

To a 100 ml round bottom flask, a mixture of compound 1 and by-product 1A (2.0 g, crude) was dissolved in a mixture of ethanol (60 ml) and 1 molar sodium hydroxide (60 ml) at room temperature, followed by addition of zinc powder (2.43 g, 37.3 mmol) at room temperature. The reaction mixture was heated under reflux and stirred for 24 hours. TLC (dichloromethane/methanol=10/1, silica gel plate) indicated that the raw materials had been completely consumed. The reaction mixture was filtered while hot, and the filtrate was subjected to rotary evaporation to remove the organic solvent, and then adjusted to pH=8 with 1N dilute hydrochloric acid. Precipitation of solid was observed. After filtration, the filter cake was mixed in methanol (60 ml), added with a solution of hydrogen chloride in methanol (5 ml, 4 M) to substantially completely dissolve the solid, and prepared concentratedly into a sample with reverse-phase silica gel. The resulting mixture was purified by reverse-phase column chromatography (methanol/water), to give main product 2 and by-product compound 22 (4.8 mg, purple solid).

Compound 22: LC-MS (ESI$^+$): m/z 366.2 (M+H)$^+$.

Compound 22: $^1$H NMR (400 MHz, DMSO-d$_6$) δ 12.42 (s, 1H), 10.14 (s, 1H), 9.89 (s, 1H), 7.97 (s, 1H), 7.65 (s, 1H), 6.51 (s, 1H), 3.91 (s, 2H), 3.03-2.91 (m, 2H), 2.82 (d, J=4.9 Hz, 3H), 2.40 (s, 3H), 1.79-1.59 (m, 5H), 1.43 (d, J=12.1 Hz, 2H), 1.23 (t, J=13.0 Hz, 1H).

Example 14: Synthesis of Compound 23

Synthesis scheme

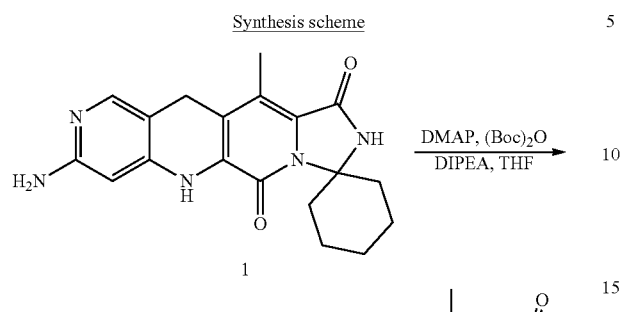

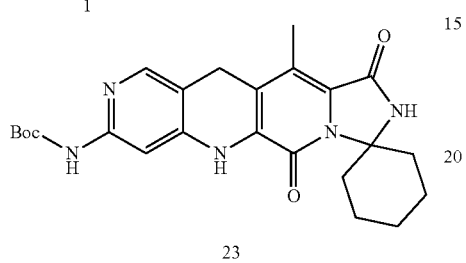

23

Steps: Tert-Butyl (12-methyl-1,5-dioxo-1,5,6,11-tetrahydro-2H-spiro[cyclohexane-1,3-imidazole[1,5:1,6]pyrido[3,4b][1,6]naphthalene]-8-yl)aminoformate (Compound 23)

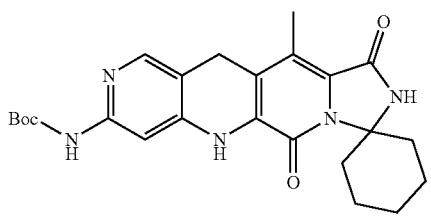 [SMILES: Cc1c2c(c(=O)n3c1C(=O)NC31CCCCC1)Nc1cc(NC(=O)OC(C)(C)C)ncc1C2]

To a solution of 8'-amino-12'-methyl-6',11'-dihydro-2'H-spiro[cyclohexane-1,3'-imidazo[1',5':1,6]pyrido[3,4-b][1,6]naphthyridine]-1',5'-dione (300 mg, 0.85 mmol) in tetrahydrofuran (5 ml), N,N-dimethylaminopyridine (207.7 mg, 1.7 mmol), (Boc)$_2$O (927.5 mg, 4.25 mmol) and diisopropylethylamine (549.2 mg, 4.25 mmol) were successively added at room temperature under the protection of nitrogen. Then the reaction was stirred at room temperature overnight under the protection of nitrogen. LCMS showed that the raw materials had been completely consumed. The reaction solution was extracted with dichloromethane (30 ml×2), and the organic phase was washed with brine, dried over anhydrous sodium sulfate, filtered and spin-dried to give a crude product. The crude product was subjected to column chromatography using petroleum ether and ethyl acetate as eluents (petroleum ether/ethyl acetate=6/1). The obtained product was purified by preparative HPLC (ACN/H$_2$O) to give compound 23 (13 mg, yield 3.4%) as a yellow solid.

LC-MS (ESI$^+$): m/z 452.53 (M+H)$^+$.

$^1$H NMR (400 MHz, DMSO-d$_6$) δ 10.15 (s, 1H), 7.87 (s, 1H), 7.10 (s, 1H), 4.03 (s, 2H), 2.97 (t, J=10.8 Hz, 2H), 2.39 (s, 3H), 1.72-1.67 (m, 5H), 1.52 (s, 9H), 1.43 (d, J=12.5 Hz, 2H), 1.25-1.14 (m, 1H).

Example 15: Synthesis of Compound 24

Synthesis scheme

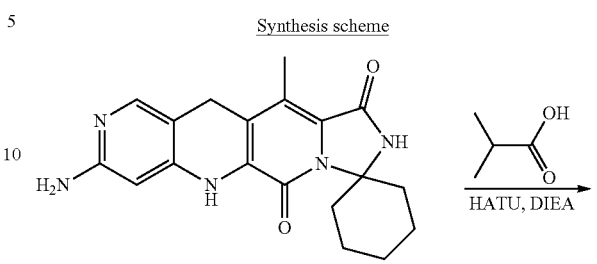

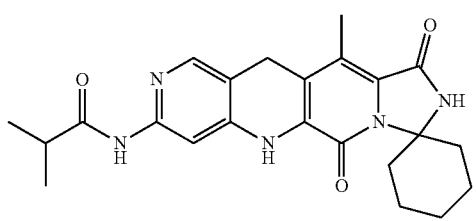 [SMILES: Cc1c2c(c(=O)n3c1C(=O)NC31CCCCC1)Nc1cc(NC(=O)C(C)C)ncc1C2]

24

Steps: N-(12methyl-1,5-dioxo-1,5,6,11-tetrahydro-2H-spiro[cyclohexane-1,3-imidazole[1,5:1,6]pyrido[3,4b][1,6]naphthyridine]-8-yl)isobutyramide (Compound 24)

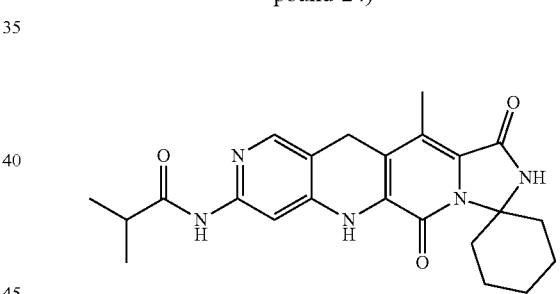

To a solution of 8'-amino-12'-methyl-6',11'-dihydro-2'H-spiro[cyclohexane-1,3'-imidazo[1',5':1,6]pyrido[3,4-b][1,6]naphthyridine]-1',5'-dione (100 mg, 0.285 mmol) in DMF (5 ml), isobutyric acid (50.2 mg, 0.57 mmol)), HATU (217 mg, 0.57 mmol) and DIPEA (73.5 mg, 0.57 mmol) were added at room temperature, and stirred at room temperature overnight. LCMS showed that about 50% of the raw materials had not been consumed. The reaction solution was added with water, and then extracted with dichloromethane (20 ml×2). The organic phase was dried with Na$_2$SO$_4$, filtered, and spin-dried to give a crude product which was purified by preparative HPLC to give compound 24 (10 mg, yield 8.3%) as a yellow solid.

LC-MS (ESI$^+$): m/z 422.2 (M+H)$^+$.

$^1$H NMR (400 MHz, DMSO-d$_6$) δ 11.58 (s, 1H), 10.35 (s, 1H), 10.20 (s, 1H), 7.92 (s, 1H), 7.06 (s, 1H), 4.07 (s, 2H), 2.97 (t, J=11.6 Hz, 2H), 2.74-2.70 (m, 1H), 2.40 (s, 3H), 1.78-1.59 (m, 5H), 1.44 (d, J=11.8 Hz, 2H), 1.24-1.20 (m, 1H), 1.15 (d, J=6.7 Hz, 6H).

Example 16: Synthesis of Compound 25

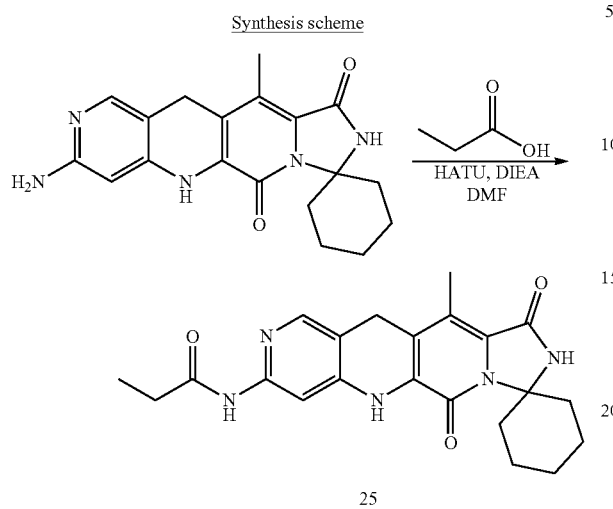

Steps: (12-methyl-1,5-dioxo-1,5,6,11-tetrahydro(2'H-spirocyclohexane-1,3-imidazo[1,5:1,6]pyrido[3,4-b][1,6]naphthyridine[8]propionyl)amine (Compound 25)

To a solution of 8'-amino-12'-methyl-6',11'-dihydro-2'H-spiro[cyclohexane-1,3'-imidazo[1',5':1,6]pyrido[3,4-b][1,6]naphthyridine]-1',5'-dione (100 mg, 0.284 mmol) in DMF (4 ml), HATU (216 mg, 0.569 mmol), diisopropylethylamine (146 mg, 1.138 mmol) and propionic acid (42 mg, 0.569 mmol) were added at room temperature. The reaction was stirred at room temperature for 16 hours under the protection of nitrogen. LCMS showed that the raw materials had been completely consumed and the mass spectrum of the product was monitored. The reaction mixture was extracted with dichloromethane (50 ml×2) and washed with water. The organic phase was dried over anhydrous sodium sulfate, filtered, and subjected to rotary evaporation to dryness to give a crude product. The crude product was purified by preparative HPLC to give compound 25 (4 mg, yield 3.4%) as a yellow solid.

LC-MS (ESI$^+$): m/z 408.4 (M+H)$^+$.

$^1$H NMR (400 MHz, DMSO-d$_6$) δ 11.54 (s, 1H), 10.15 (s, 2H), 7.90 (s, 1H), 7.14 (s, 1H), 4.04 (s, 2H), 2.97 (t, J=11.1 Hz, 2H), 2.46 (d, J=7.5 Hz, 2H), 2.39 (s, 3H), 1.69 (dd, J=46.0, 14.0 Hz, 5H), 1.44 (d, J=12.0 Hz, 2H), 1.21 (d, J=12.8 Hz, 1H), 1.09 (t, J=7.5 Hz, 3H).

Example 17: Synthesis of Compound 26

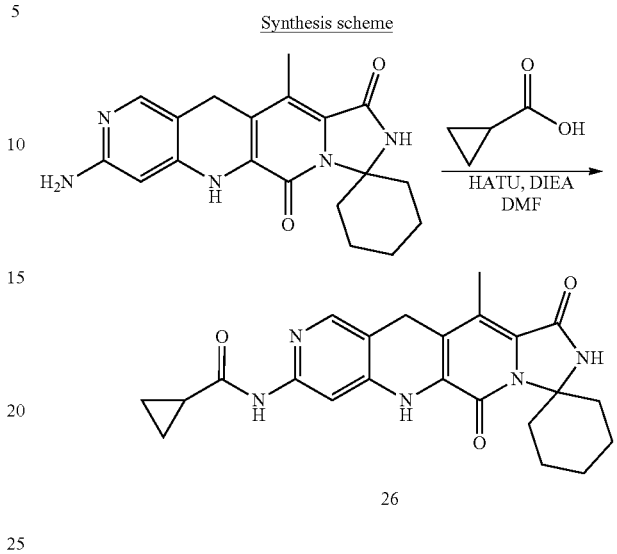

Steps: (12-methyl-1,5-dioxo-1,5,6,11-tetrahydro(2'H-spirocyclohexane-1,3-imidazo[1,5:1,6]pyrido[3,4-b][1,6]naphthyridine[8]cyclopropylformyl)amine (Compound 26)

To a solution of 8'-amino-12'-methyl-6',11'-dihydro-2'H-spiro[cyclohexane-1,3'-imidazo[1',5':1,6]pyrido[3,4-b][1,6]naphthyridine]-1',5'-dione (100 mg, 0.284 mmol) in DMF (4 ml), HATU (216 mg, 0.569 mmol), diisopropylethylamine (146 mg, 1.138 mmol) and cyclopropyl formic acid (49 mg, 0.569 mmol) were added at room temperature. The reaction was stirred at room temperature for 16 hours under the protection of nitrogen. LCMS showed that the raw materials had been completely consumed, and the mass spectrum of the product was monitored. The reaction mixture was extracted with dichloromethane (50 ml×2) and washed with water. The organic phase was dried over anhydrous sodium sulfate, filtered, and subjected to rotary evaporation to dryness to give a crude product. The crude product was purified by preparative HPLC to give compound 26 (6.3 mg, yield 5.2%) as a yellow solid.

LC-MS (ESI$^+$): m/z 420.4 (M+H)$^+$.

$^1$H NMR (400 MHz, DMSO-d$_6$) δ 11.81 (s, 1H), 10.23 (s, 1H), 10.17 (s, 1H), 7.90 (s, 1H), 7.09 (s, 1H), 4.05 (s, 2H), 2.97 (t, J=11.3 Hz, 2H), 2.39 (s, 3H), 1.96-1.86 (m, 1H), 1.69 (dd, J=46.3, 13.3 Hz, 5H), 1.44 (d, J=11.9 Hz, 2H), 1.21 (d, J=15.2 Hz, 1H), 1.03-0.96 (m, 2H), 0.94 (s, 2H).

Example 18: Synthesis of Compound 27

Synthesis scheme

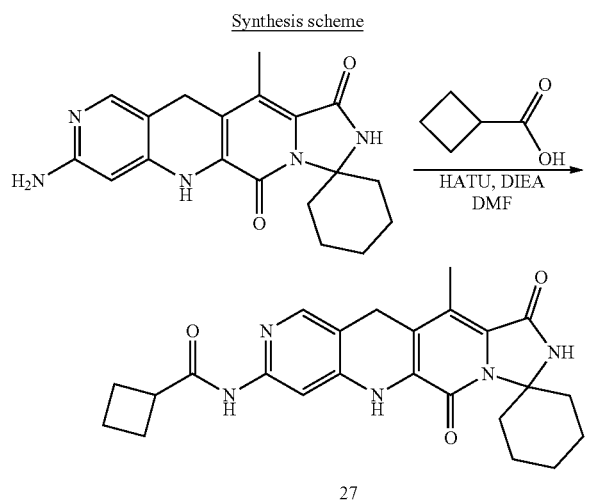

27

Steps: (12-methyl-1,5-dioxo-1,5,6,11-tetrahydro (2'H-spirocyclohexane-1,3-imidazo[1,5:1,6]pyrido[3,4-b][1,6]naphthyridine[8]cyclobutylformyl)amine (Compound 27)

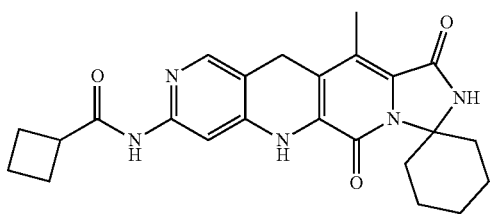 [SMILES: Cc1c2c(c(=O)n3c1C(=O)NC31CCCCC1)Nc1cc(NC(=O)C3CCC3)ncc1C2]

To a solution of 8'-amino-12'-methyl-6',11'-dihydro-2'H-spiro[cyclohexane-1,3'-imidazo[1',5':1,6]pyrido[3,4-b][1,6]naphthyridine]-1',5'-dione (100 mg, 0.3 mmol) and cyclobutyl formic acid (90 mg, 0.9 mmol) in DMF (5 ml), HATU (171 mg, 0.45 mmol) and diisopropylethylamine (120 mg, 0.9 mmol) were added at room temperature. The reaction was stirred at room temperature for 24 hours. LCMS showed that the raw materials had been completely consumed, and the mass spectrum of the product was monitored. The reaction mixture was extracted with DCM (20 ml×2) and washed with water. The organic phase was dried over anhydrous sodium sulfate, filtered, and subjected to rotary evaporation to dryness to give a crude product. The crude product was purified by preparative HPLC to give compound 27 (5 mg, yield 3.8%) as a yellow solid.

LC-MS (ESI+): m/z 434.3 (M+H)+.

1H NMR (400 MHz, DMSO-$d_6$) δ 11.32 (s, 1H), 10.21 (s, 1H), 10.17 (s, 1H), 7.92 (s, 1H), 7.10 (s, 1H), 4.05 (s, 2H), 3.38-3.31 (m, 1H), 3.04-2.88 (m, 2H), 2.39 (s, 3H), 2.30-2.11 (m, 4H), 2.03-1.93 (m, 1H), 1.89-1.60 (m, 6H), 1.49-1.37 (m, 2H), 1.27-1.12 (m, 1H).

Example 19: Synthesis of Compound 28

Synthesis scheme

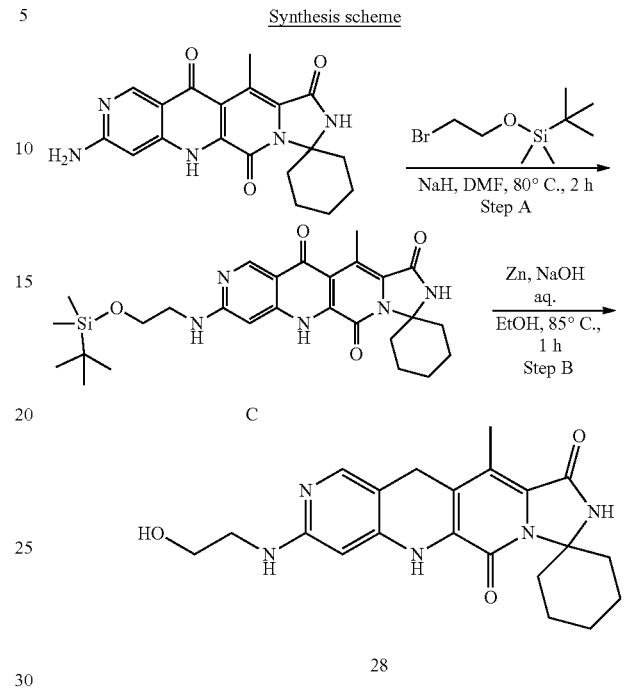

28

Step A: 8'4(2-((tert-butyldimethylsilyl)oxy)ethyl)amino)-12'-methyl-TH-spiro[cyclohexane-1,3'-dihydroimidazo[1',5':1,6]pyrido[3,4-b][1,6]naphthyridine]-1',5',11' (6'H)-trione (Compound C)

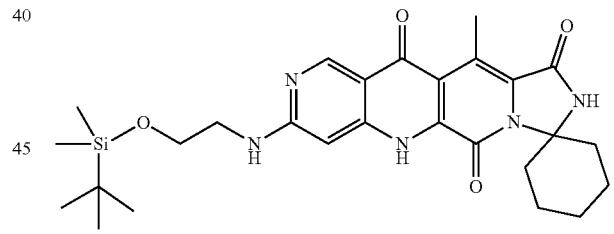

To a solution of 8'-amino12'-methyl-2'H-spiro[cyclohexane-1,3'-dihydroimidazo[1',5': 1,6]pyrido[3,4-B][1,6]naphthyridine]-1',5',11' (6'H)-trione (280 mg, 0.77 mmol) in DMF (5 ml), sodium hydride (92 mg, 3.84 mmol) was added at room temperature under the protection of nitrogen. After the reaction was stirred at room temperature for 5 minutes, (2-bromoethoxy)(tert-butyl)dimethylsilane (274 mg, 1.15 mmol) was added. The reaction mixture was stirred at room temperature for 10 minutes, and then heated and stirred at 80° C. for 2 hours. LCMS showed that the reaction had been completed. The reaction solution was cooled to room temperature and concentrated to dryness under vacuum. Water and methanol (1/1, 5 ml) were added to form a slurry, stirred at room temperature for 30 minutes, and filtered. The obtained solid was dried under vacuum to give a red product compound C (80 mg, crude).

LC-MS (ESI+): m/z 524.2 (M+H)+.

Step B: 8'((2-hydroxyethyl)amino)-12'-methyl-6', 11'-dihydro-2'H-spiro[cyclohexane-1,3'-dihydroimidazo[1',5':1,6]pyrido[3,4-b][1,6]naphthyridine]-1',5'-dione (Compound 28)

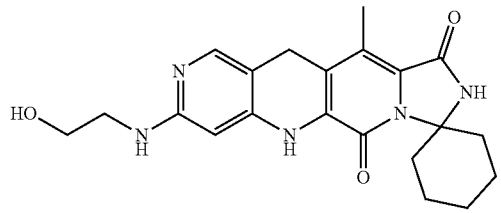 [SMILES: Cc1c2c(c(=O)n3c1C(=O)NC31CCCCC1)Nc1cc(NCCO)ncc1C2]

To a solution of compound C (70 mg, 0.13 mmol) in ethanol (6 ml), zinc powder (87 mg, 1.3 mmol) and sodium hydroxide solution (2 M, 3 ml) were added at room temperature under the protection of nitrogen. The reaction mixture was stirred at 85° C. for 1 hour. LCMS showed that the raw materials had been completely consumed. The reaction solution was quickly filtered at 85° C., and the filtrate was concentrated under vacuum. The concentrated residue was added with a small amount of water for dilution, and then adjusted to pH 5-6 with hydrochloric acid solution. A yellow solid was formed. The yellow solid was filtered to give a crude product. The crude product was purified by preparative HPLC to give the product compound 28 (5 mg, yield 9.4%) as a yellow solid.

LC-MS (ESI+): m/z 396.2 (M+H)+.

$^1$H NMR (400 MHz, DMSO-$d_6$) δ 12.38 (s, 1H), 9.88 (s, 1H), 7.61 (s, 1H), 7.37 (s, 2H), 6.44 (s, 1H), 4.36 (t, J=4.8 Hz, 2H), 3.88 (s, 2H), 3.76 (t, J=4.8 Hz, 2H), 3.01-2.92 (m, 2H), 2.27 (s, 3H), 1.75 (m, 5H), 1.26 (d, J=11.9 Hz, 3H).

Example 20: Synthesis of Compound 29

Synthesis scheme

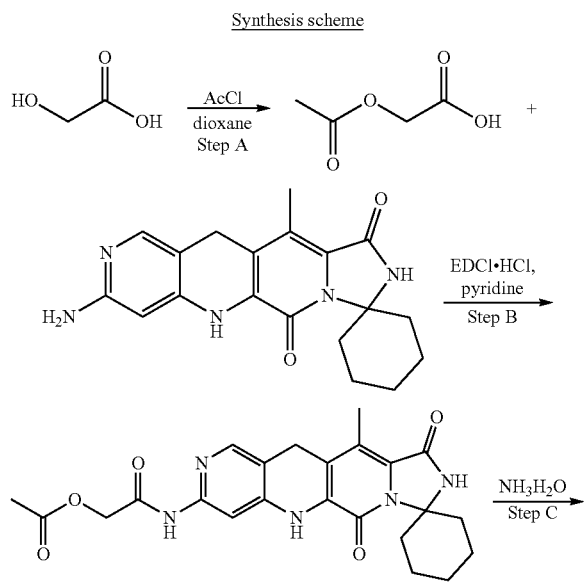

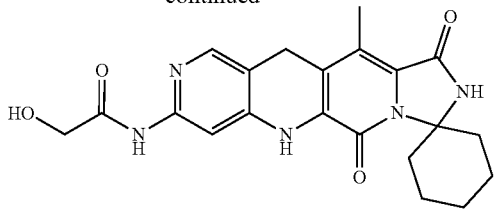

29

Experimental Procedures

Step A: 2-Acetoxy Acetic Acid

Acetyl chloride (780 mg, 11 mmol) was added to a solution of 2-hydroxyacetic acid (760 mg, 10 mmol) in dioxane (30 ml) at room temperature. Then the reaction solution was stirred and reacted under reflux for 6 hours. Water (2 ml) was added to the reaction solution to quench the reaction. The reaction solution was directly dried over anhydrous sodium sulfate, filtered and concentrated to give a crude product which was purified by a silica gel column and eluted with petroleum ether/ethyl acetate (PE/EA=1/1) to give the product (450 mg, yield 38%) as a white solid.

$^1$H NMR (400 MHz, DMSO-$d_6$) δ 13.01 (s, 1H), 4.53 (s, 2H), 2.08 (s, 3H).

Step B: 24(12'-methyl-1',5'-dioxo-1',5',6',11'-tetrahydro-2'H-spiro[cyclohexane-1,3'-imidazo[1',5':1,6]pyrido[3,4-b][1,6]naphthopyridine]-8'-yl)amino)-2-oxo ethylacetate EDCI.HCL (428 mg, 2.24 mmol) was added to a solution of 8'-amino-12'-methyl-6',11'-dihydro-2'H-spiro[cyclohexane-1,3'-imidazo[1',5':1,6]pyrido[3,4-b][1,6]naphthyridine]-1',5'-dione (100 mg, 0.28 mmol) and 2-acetoxyacetic acid (132 mg, 1.12 mmol) in pyridine (5 ml). The reaction solution was then stirred at 52° C. for 16 hours. LCMS showed 40% consumption of the raw materials. The reaction mixture was added with water (2 ml), and then extracted with dichloromethane/isopropanol (dichloromethane/isopropanol=3/1). The organic layer was dried over anhydrous sodium sulfate, filtered and concentrated to give a crude product (40 mg, crude), which was directly used for the next step.

LC-MS (ESI+): m/z 452.4 (M+H)+.

Step C: 2-hydroxy-N-(12'-methyl-1',5'-dioxin-1',5',6',11'-tetrahydro-2'H-spiro[cyclohexane-1,3'-imidazo[1',5':1,6]pyrido[3,4-b][1,6]naphthopyridine]-8'-yl)acetamide (Compound 29)

2-((12'-Methyl-1',5'-dioxo-1',5',6',11'-tetrahydro-2'H-spiro[cyclohexane-1,3'-imidazo[1',5':1,6]pyrido[3,4-b][1,6]naphthopyridine]-8'-yl)amino)-2-oxoethyl acetate (35 mg, crude) was dissolved in ammonia water (5 ml), and stirred at room temperature for 2 hours. LCMS showed that the raw materials had been completely consumed, and MS of the product was detected. The reaction solution was diluted with water (10 ml), and then extracted with dichloromethane/isopropanol (dichloromethane/isopropanol=3/1), and the organic phase was washed with brine. The crude product obtained by concentrating the organic layer was purified by preparative HPLC (methanol/water) to give the product compound 29 (1.5 mg) as a yellow solid.

LC-MS (ESI⁺): m/z 410.3 (M+H)⁺.

$^1$H NMR (400 MHz, DMSO-$d_6$) δ 11.32 (s, 1H), 10.48 (s, 1H), 10.21 (s, 1H), 8.00 (s, 1H), 7.49 (s, 1H), 5.33 (t, J=4.4 Hz, 1H), 4.14 (s, 2H), 4.08 (s, 2H), 2.97 (t, J=11.6 Hz, 2H), 2.40 (s, 3H), 1.63-1.77 (m, 5H), 1.42-1.46 (m, 2H), 1.30-0 1.33 (m, 1H).

MNK Biological Enzyme Assay

A HTRF kinase assay kit (Cisbio, catalog number 62ST1PEB) was used to determine the MNK inhibitory activity of the compounds. All kinase reactions were performed in the reaction buffer (provided in the kit). The final MNK1 reaction involved 3 ng/ul recombinant MNK1 (ThermoFisher, PV6023), 1 µM MNK substrate peptide STK1 (provided in the kit), 100 µM ATP, and different concentrations of the inhibitory compounds of interest. The final MNK2 reaction involved 1 ng/µl recombinant MNK2 (ThermoFisher, PV5607), 1 µM MNK substrate peptide STK1 (provided in the kit), 100 µM ATP, and different concentrations of the inhibitory compounds of interest. The final DMSO concentration in each of the reactions was 1%.

The kinase reaction was performed in a final volume of 10 µl in a 384-well white flat-bottomed polystyrene plate. The MNK1/2 enzyme was pre-incubated with the compound and substrate peptide for 5 minutes, and then ATP was added thereto. After addition of ATP, the kinase reaction was incubated at 25° C. for 120 minutes or 60 minutes. The reaction was subsequently terminated by adding 5 µl of EU3+ substrate antibody detection reagent and 5 µl of XL665 detection reagent, and incubating for another 60 minutes. The luminescent signal was detected with an EnVision microplate reader counter (Perkin Elmer), and the signal from 10-point dilution series of the compounds was used to calculate the compound concentration ($IC_{50}$) required to achieve 50% inhibition of enzyme activity.

The results of these assays were listed in Table 1 below. In this respect, $IC_{50}$ values which are less than 0.01 µM were marked as "+++", which are from 0.01 to 0.1 µM were marked as "++", and which are greater than 0.1 and up to 10.0 µM were marked as "+", and NA meant "not detected".

TABLE 1

MNK biological enzyme assay ($IC_{50}$)

| Compound No. | MNK1 | MNK2 | Compound No. | MNK1 | MNK2 |
|---|---|---|---|---|---|
| 1 | ++ | ++ | 2 | ++ | +++ |
| 3 | ++ | ++ | 4 | ++ | ++ |
| 5 | +++ | +++ | 6 | ++ | +++ |
| 7 | ++ | ++ | 8 | ++ | NA |
| 9 | ++ | NA | 10 | ++ | ++ |
| 13 | ++ | ++ | 16 | ++ | +++ |
| 20 | ++ | +++ | 21 | +++ | +++ |
| 22 | ++ | ++ | 23 | +++ | +++ |
| 24 | +++ | +++ | 25 | ++ | +++ |
| 26 | +++ | +++ | 27 | ++ | +++ |

Intracellular peIF4E Signaling Assay

Phosphorylated eIF4E was determined using CisBio peIF4E assay kit (CisBio, catalog number 64EF4PEG). The cells were plated in a 96-well cell culture plate in a volume of 90 µL, and the number of cells per well was 5*10⁴. The compounds (10x) were subjected to 3-fold serial dilution, added to the cell plate in a volume of 10 µL with the final DMSO concentration being 1%, and incubated at 37° C. for two hours. The cell plate was centrifuged at 300 g for 5 minutes, and the cell supernatant was carefully removed. The cell plate was immediately added with 50 µL of cell lysis buffer (1λ) and incubated at 25° C. with shaking for at least 30 minutes. After homogenization by pipetting, 16 µL of cell lysate was transferred from the 96-well cell culture plate to a 384-well small-volume microwell plate. According to the kit instruction, an antibody mixture solution was prepared with a detection buffer, and was added in a volume of 4 µL to the 384-well small-volume microwell plate containing the cell lysate. The plate was covered with a plate sealer, incubated overnight at 25° C., and was read for fluorescence emission at two different wavelengths (665 nm and 615 nm) on the EnVision microplate reader counter. The emission ratio was imported into a GraphPadPrism software to fit the compound concentration ($IC_{50}$) required for 50% inhibition of enzyme activity.

The results of these assays were listed in Table 2 below. In this respect, $IC_{50}$ values which are less than 0.05 µM were marked as "+++", which are from 0.05 to 1.0 µM were marked as "++", and which are greater than 1.0 and up to 100 µM were marked as "+", and NA meant "not detected".

TABLE 2 peIF4E signaling cell assay ($IC_{50}$)

| Compound No. | $IC_{50}$ | Compound No. | $IC_{50}$ |
|---|---|---|---|
| 1 | +++ | 2 | +++ |
| 3 | ++ | 4 | ++ |
| 5 | +++ | 6 | +++ |
| 7 | + | 8 | ++ |
| 9 | ++ | 10 | ++ |
| 11 | + | 12 | ++ |
| 13 | ++ | 14 | ++ |
| 15 | ++ | 16 | +++ |
| 17 | + | 18 | ++ |
| 19 | + | 20 | +++ |
| 22 | +++ | 23 | +++ |
| 24 | +++ | 25 | +++ |
| 26 | +++ | 27 | +++ |

Evaluation of Kinase Selectivity of Compound 2

KinomeScan was used to determine the kinase selectivity of compound 2. When the concentration of compound 2 was 1 µM, the KinomeScan analysis for 468 kinases (403 of which were wild-type kinases) showed that, except for GAK and DRAK1, interaction with kinases other than MNK1/2 was not observed. Dose response analysis showed that Kd values of the interactions of compound 2 with GAK and DRAK1 were 50 nM and 370 nM, respectively, indicating that this inhibitor had excellent kinase selectivity. These results were shown in FIG. 1 and Table 3. The above results indicated that compound 2 was a highly selective MNK1/2 inhibitor.

TABLE 3

Kinase inhibition selectivity of compound 2

| Compound No. | Type of selectivity score | Number of hits | Number of wild-type kinases | Selectivity score |
|---|---|---|---|---|
| Compound 2 | S(35) | 4 | 403 | 0.01 |
| Compound 2 | S(10) | 3 | 403 | 0.007 |
| Compound 2 | S(1) | 1 | 403 | 0.002 |

TABLE 4

| Kinase | % Inhibition @ 1 μM |
| --- | --- |
| MNK1 | 97.2% |
| MNK2 | 99.5% |
| STK17A/DRAK1 | 62% |
| GAK | 97.8% |
| Other 399 wild-type protein kinases | <50% |

Detection of Expression of Immune Checkpoint Proteins on Cell Surface and Secretion Level of Cytokines Gradient centrifugation was used to extract PBMC cells from peripheral blood of healthy people. The PBMC cells were activated with 5 μg/ml PHA (Sigma), and treated with different concentrations of compounds (0, 0.01, 0.1, 1, 3, 10 μM). After 48 hours, the cells and culture supernatants were collected, respectively. Flow cytometry was used to detect the expression of immune checkpoints, PD-1, Tim-3 and Lag-3 on cell surface, and to detect the secretion level of various cytokines (IL-6, IL-10 and TNF-α) in the cell culture supernatants.

The results were shown in FIG. 2 to FIG. 7. The results showed that compounds 2, 21, and 26 significantly inhibited the expression of immune checkpoint proteins, PD-1, Tim-3 and Lag-3, as well as the secretion of IL-10, IL-6 and TNF-α.

Pharmacokinetic Test of Compounds

In the examples, rat pharmacokinetic tests were performed for compounds 2 and 26 to illustrate their pharmacokinetic properties in rats.

Formulation of Liquors of Compound 2:

Formulation of solution for intravenous administration: compound 2 was dissolved in a solution of 20% PEG-400, 10% propylene glycol, and 70% water.

Formulation of suspension for intragastric administration: compound 2 was dissolved in a solution of 20% PEG-400, 10% propylene glycol, and 70% water.

Administration dosage of compound 2: 3 mg/kg for intravenous injection, 10 mg/kg for intragastric administration.

Experimental Method for Pharmacokinetic Study in Rats

Six SD rats, male, weighing 180-220 g, fasting for 12 hours, were randomly divided into 2 groups, 3 in each group. The animals in group A were intragastrically administrated with the compound liquor at a dose of 10 mg/kg; the animals in group B were intravenously administrated with the compound liquor via tails at a dose of 3 mg/kg. Blank blood was harvested before administration; about 100 μL of venous blood was harvested at different time points after administration, placed in a test tube added with heparin and centrifuged, and about 50 μL of blood plasma was collected and stored at −20° C. for testing.

Formulation of Liquors of Compound 26:

Formulation of solution for intravenous administration: compound 26 was dissolved in a solution of 5% DMSO+ 10% Solutol HS15+85% (20% HP-(3-CD physiological saline).

Formulation of suspension for intragastric administration: compound 26 was dissolved in a solution of 5% DMSO+ 10% Solutol HS15+85% (20% HP-(3-CD physiological saline).

Administration dosage of compound 26: 1 mg/kg for intravenous injection, 3 mg/kg for intragastric administration.

Experimental Method for Pharmacokinetic Study in Rats

Six SD rats, male, weighing 180-220 g, fasting for 12 hours, were randomly divided into 2 groups, 3 in each group. The animals in group A were intragastrically administrated with the compound liquor at a dose of 3 mg/kg; the animals in group B were intravenously administrated with the compound liquor via tails at a dose of 1 mg/kg. Blank blood was harvested before administration; about 100 μL of venous blood was harvested at different time points after administration, placed in a test tube added with heparin and centrifuged, and about 50 μL of blood plasma was collected and stored at −20° C. for testing.

The experimental results were shown in Table 5 and Table 6:

TABLE 5

Pharmacokinetic data of compound 2

| Mode of administration | Dosage of administration (mg/kg) | $T_{max}$ (hr) | $C_{max}$ (ng/ml) | $AUC_{last}$ (ng/ml * hr) | $AUC_{INF}$ (ng/ml * hr) | $T_{1/2}$ (hr) | CL (L/hr/kg) | Vz (L/kg) | % F |
| --- | --- | --- | --- | --- | --- | --- | --- | --- | --- |
| i.v. | 3 | — | — | 456 | 471 | 1.58 | 6.63 | 12.3 | — |
| p.o. | 10 | 2.17 | 130 | 584 | 624 | 5.07 | — | — | 38.8 |

TABLE 6

Pharmacokinetic data of compound 26

| Mode of administration | Dosage of administration (mg/kg) | $T_{max}$ (hr) | $C_{max}$ (ng/ml) | $AUC_{last}$ (ng/ml * hr) | $AUC_{INF}$ (ng/ml * hr) | $T_{1/2}$ (hr) | CL (L/hr/kg) | Vz (L/kg) | % F |
| --- | --- | --- | --- | --- | --- | --- | --- | --- | --- |
| i.v. | 1 | — | — | 619 | 632 | 3.73 | 1.63 | 4.14 | — |
| p.o. | 3 | 1.75 | 45.2 | 402 | 391 | 6.97 | — | — | 21.7 |

All documents mentioned in this specification are incorporated herein by reference to the same extent as if each independent document was individually indicated to be incorporated by reference. In addition, it should be understood that, after reading the above teaching content of the invention, those skilled in the art can make various changes or modifications to the invention, and those equivalents also fall within the scope defined by the appended claims of the present application.

What is claimed is:

1. A compound of formula (I):

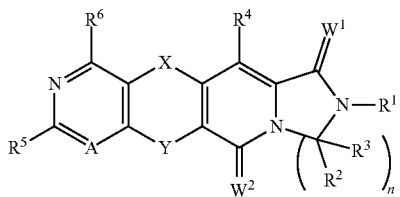

or a stereoisomer, tautomer, prodrug, solvate, hydrate, stable isotope derivative or pharmaceutically acceptable salt thereof, wherein:

A is —$CR^7$—;

X is —$(CR^{1a}R^{1b})_p$-M-$(CR^{2a}R^{2b})_q$—, wherein M is a chemical bond or selected from the group consisting of —$N(R^9)$—, —O—, —S—, —C(O)—, —S(O)—, —$S(O)_2$—, —C(O)NH—, or —NHC(O)—;

p and q are each independently 0, 1 or 2;

Y is selected from the group consisting of —$N(R^8)$—, —O—, —S—, —C(O)—, —S=O, —$S(O)_2$—, or —$CHR^9$—;

$W^1$ and $W^2$ are independently selected from the group consisting of O, S or N—OR', wherein R' is C1-C8 alkyl;

$R^1$ is selected from the group consisting of hydrogen, —OH, acetyl, C1-C8 alkyl, —C(O)(C1-C8 alkyl), —C(O)(C3-C8 cycloalkyl), —COOH, —C(O)O—(C1-C8) alkyl, C3-C8 cycloalkyl, 5-12 membered aryl, 5-12 membered heteroaryl, or 5-12 membered heterocyclyl;

n is 1, 2 or 3;

$R^2$ and $R^3$ are each independently selected from the group consisting of hydrogen, C1-C8 alkyl, C2-C8 alkenyl, C2-C8 alkynyl, C6-C10 aryl, 5-12 membered heteroaryl, C1-C4 alkylene-(5-12) membered heteroaryl, C3-C8 cycloalkyl, C1-C4 alkylene-(C3-C8)cycloalkyl, 5-12 membered heterocyclyl, C1-C4 alkylene-(5-12) membered heterocyclyl; or $R^2$ and $R^3$ together with the carbon atom connected thereto form the radicals selected from the group consisting of: C3-C10 monocyclic alkyl, C3-C10 bicyclic or polycyclic alkyl, 5-12 membered heteromonocyclic alkyl containing 1-3 N, O or S atoms, 5-12 membered heterobicyclic or heteropolycyclic alkyl containing 1-3 N, O or S atoms;

$R^{1a}$, $R^{1b}$, $R^{2a}$ and $R^{2b}$ are each independently selected from the group consisting of hydrogen, halogen, hydroxy, —SH, hydroxy-(C1-C4) alkylene, cyano, C1-C4 alkyl, C1-C4 alkoxy;

$R^4$ is independently selected from the group consisting of hydrogen, halogen, hydroxy, —SH, hydroxy-(C1-C4) alkylene, cyano, C1-C4 alkyl, C1-C4 alkoxy, —C(O)(C1-C8 alkyl), —C(O)(C3-C8 cycloalkyl), —COOH, —C(O)O—(C1-C8) alkyl, —S(C1-C8 alkyl), C2-C8 alkenyl, C2-C8 alkynyl, C3-C8 cycloalkyl, C6-C10 aryl, 5-12 membered heteroaryl or 5-12 membered heterocyclyl;

$R^5$, $R^6$ and $R^7$ are each independently selected from the group consisting of —H, —OH, —CN, —$SR^{10}$, halogen, —$S(O)_2$(C1-C8)alkyl, —NH—$S(O)_2$(C1-C8)alkyl, —C(O)N($R^{10}$)$_2$, —NHC(O)$R^{10}$, —N($R^{10}$)$_2$, —(C1-C4 alkylene)N($R^{10}$)$_2$, C1-C8 alkyl, C2-C8 alkenyl, C2-C8 alkynyl, C1-C8 haloalkyl, —O(C1-C8 alkyl), —O(C1-C8 haloalkyl), —O(C1-C8 alkylene)NH$R^{10}$, —O(C1-C8 alkylene)N($R^{10}$)$_2$, C6-C10 aryl, 5-12 membered heteroaryl, C1-C4 alkylene-(5-12) membered heteroaryl, C3-C8 monocyclic alkyl, C1-C4 alkylene-(C3-C8)cycloalkyl, 5-12 membered heterocyclyl, C1-C4 alkylene-(5-12) membered heterocyclyl; or $R^5$ and $R^7$ together with the carbon atom connected thereto form C6-C10 aryl, 5-12 membered heteroaryl, C3-C8 cycloalkyl, 5-12 membered heterocyclyl;

$R^{10}$ is selected from the group consisting of —H, —OH, —C(O)O(C1-C8 alkyl), —C(O)(C1-C8 alkyl), —C(O)—NH$_2$, —C(O)—NH (C1-C8 alkyl), —NH—C(O)(C1-C8 alkyl), NH$_2$—C(O)—(C1-C4 alkylene), —S(C1-C8 alkyl), acetyl, C1-C8 alkyl, C2-C8 alkenyl, C2-C8 alkynyl, —O(C1-C8 alkyl), —(C1-C8 haloalkyl), C1-C8 alkylamino, —C(O)(C1-C8 alkyl), —C(O)(C3-C8 cycloalkyl), —C(O)O—(C1-C8 alkyl), C3-C8 cycloalkyl, C6-C10 aryl, 5-12 membered heteroaryl or 5-12 membered heterocyclyl;

wherein, each of alkyl, alkylene, cycloalkyl, aryl, heteroaryl, heterocyclyl, amino are optionally substituted with 1, 2 or 3 J groups, the J group is selected from the group consisting of —$SR^9$, —S(O) $R^9$, —S(O) $2R^9$, —S(O)N($R^9$)$_2$, —N($R^9$)$_2$, —C(O)O$R^9$, —C(O)$R^9$, —C(O)—N($R^9$)$_2$, hydroxy, cyano, halogen, acetyl, C1-C4 alkyl, C2-C4 alkenyl, C2-C4 alkynyl, C1-C4 alkoxy, haloalkyl, —S—(C1-C4 alkyl), cyano-(C1-C4 alkylene), C1-C4 alkylamino, NH$_2$—C(O)—(C1-C4) alkylene, N($R^9$)$_2$—C(O)—(C1-C4)alkylene, —$CHR^9$—C(O)—(C1-C4) alkyl, —C(O)—(C1-C4) alkyl, 5-12 membered heterocyclyl, C1-C4 alkylene-(5-12) membered heterocyclyl, C3-C8 cycloalkyl, C1-C4 alkylene-(C3-C8)cycloalkyl, C2-C4 alkylene-(C3-C8)cycloalkyl, —$CHR^9$—C(O)—(C3-C8)cycloalkyl, —$CHR^9$—C(O)—(C6-C10)aryl, —$CHR^9$—(C6-C10)aryl, —C(O)—(C6-C10)aryl, —$CHR^9$—C(O)—(5-12) membered heterocyclyl, —C(O)-(5-12) membered heterocyclyl; or two J groups connected to the same atom forming oxo (=O); and $R^8$ and $R^9$ are hydrogen, C1-C4 alkyl, hydroxy-(C1-C4) alkyl, C3-C8 cycloalkyl, 5-12 membered heterocyclyl, —NH$_2$ or —OH.

2. The compound of claim 1, characterized in that, n is 1, and Y is —$N(R^8)$—.

3. The compound of claim 1, characterized in that, X is selected from the group consisting of: —C(=O)—, —CH$_2$—, —CD$_2$-, —CH(OH)—, —CH(CH$_3$)— or —CF$_2$—.

4. The compound of claim 1, characterized in that, $W^1$ and $W^2$ are O.

5. The compound of claim 1, characterized in that, $R^2$ and $R^3$ are each independently selected from the group consisting of: hydrogen, methyl, ethyl, propyl, isopropyl, tert butyl, vinylidene, propynylidene, 2-methyl-1-propenylidene, benzyl, fluorobenzyl, chlorobenzyl, cyclopentyl, cyclohexyl, difluorocyclohexyl, trifluoromethyl, 1,1,1-trifluoroethenyl, thiazolyl, methylenenitrile, phenyl, chlorophenyl, fluorophenyl, fluorochlorophenyl, difluorophenyl, pyridyl, methylpyridyl, chloropyridyl, N-methylaminomethylene, aminomethylene, 1-aminoethenyl, methylaminomethylene, 1-hydroxyethenyl, or 1,1-difluoroethenyl; or $R^2$ and $R^3$ together with the carbon atom connected thereto form rings selected from the group consisting of: cyclobutyl ring, cyclopentyl ring, cyclohexyl ring, bicyclo[2.2.2]octane ring, or norborneol ring.

6. The compound of claim 1, characterized in that, the compound is selected from the group consisting of:

| Compound | Structure |
|---|---|
| Compound 1 | 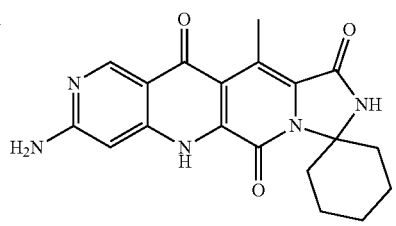 [SMILES: Cc1c2n(c(=O)c3[nH]c4cc(N)ncc4c(=O)c13)C1(CCCCC1)NC2=O] |
| Compound 2 | 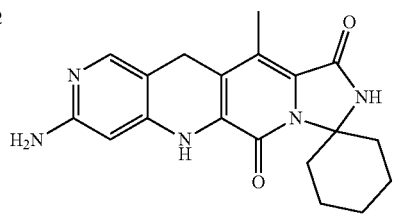 |
| Compound 3 | 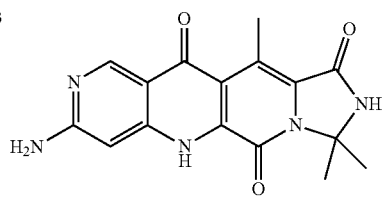 |
| Compound 4 | 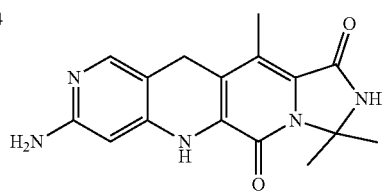 |
| Compound 5 | 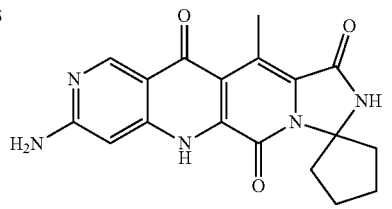 |
| Compound 6 | 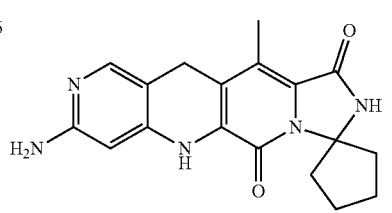 |

-continued

| Compound | Structure |
|---|---|
| Compound 7 | 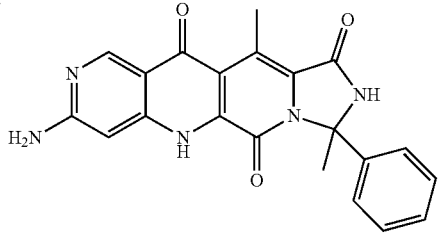 [SMILES: Cc1c2n(c(=O)c3[nH]c4cc(N)ncc4c(=O)c13)C(C)(c1ccccc1)NC2=O] |
| Compound 8 | 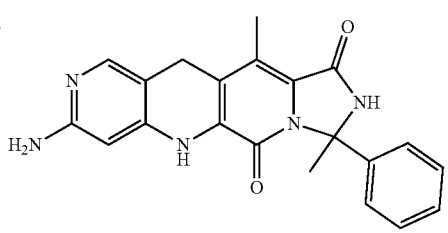 [SMILES: Cc1c2c(c(=O)n3c1C(=O)NC3(C)c1ccccc1)Nc1cc(N)ncc1C2] |
| Compound 9 | 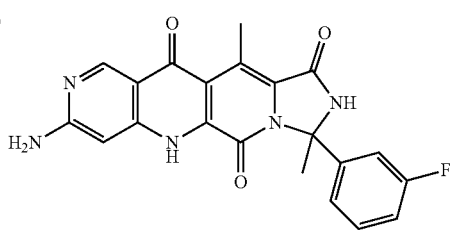 [SMILES: Cc1c2n(c(=O)c3[nH]c4cc(N)ncc4c(=O)c13)C(C)(c1cccc(F)c1)NC2=O] |
| Compound 10 | 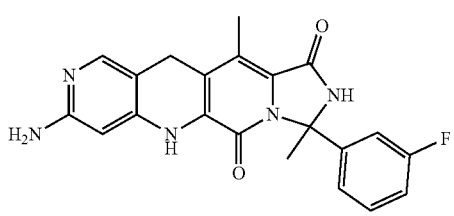 [SMILES: Cc1c2c(c(=O)n3c1C(=O)NC3(C)c1cccc(F)c1)Nc1cc(N)ncc1C2] |
| Compound 11 | 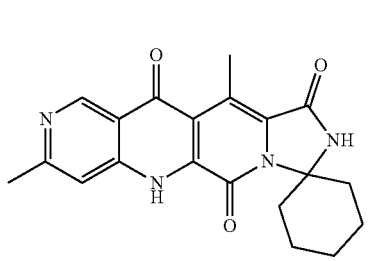 [SMILES: Cc1cc2[nH]c3c(=O)n4c(c(C)c3c(=O)c2cn1)C(=O)NC41CCCCC1] |
| Compound 12 | 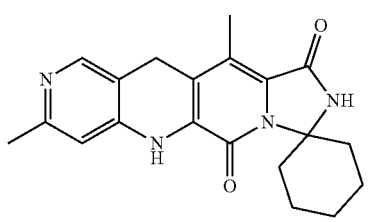 [SMILES: Cc1cc2c(cn1)Cc1c(C)c3n(c(=O)c1N2)C1(CCCCC1)NC3=O] |

-continued
| Compound | Structure |
|---|---|
| Compound 13 | 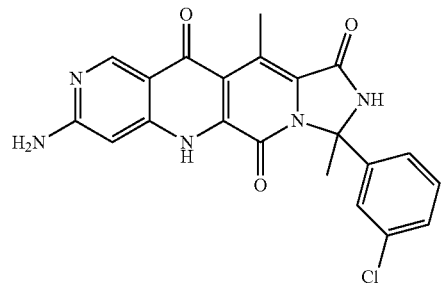 [SMILES: Cc1c2n(c(=O)c3[nH]c4cc(N)ncc4c(=O)c13)C(C)(c1cccc(Cl)c1)NC2=O] |
| Compound 14 | 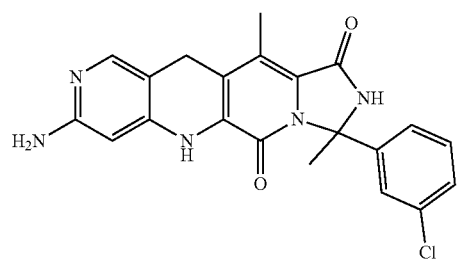 [SMILES: Cc1c2c(c(=O)n3c1C(=O)NC3(C)c1cccc(Cl)c1)Nc1cc(N)ncc1C2] |
| Compound 15 | 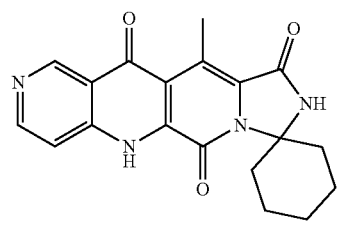 [SMILES: Cc1c2n(c(=O)c3[nH]c4ccncc4c(=O)c13)C1(CCCCC1)NC2=O] |
| Compound 16 | 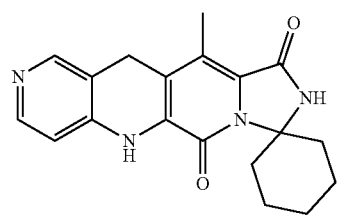 [SMILES: Cc1c2c(c(=O)n3c1C(=O)NC31CCCCC1)Nc1ccncc1C2] |
| Compound 17 | 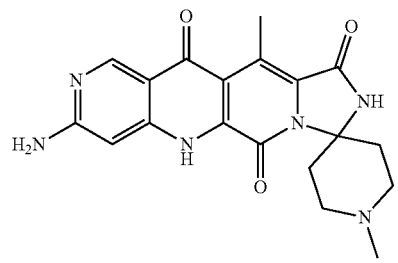 [SMILES: Cc1c2n(c(=O)c3[nH]c4cc(N)ncc4c(=O)c13)C1(CCN(C)CC1)NC2=O] |
| Compound 18 | 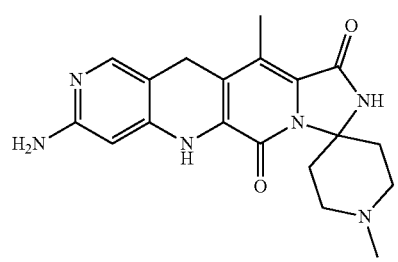 [SMILES: Cc1c2c(c(=O)n3c1C(=O)NC31CCN(C)CC1)Nc1cc(N)ncc1C2] |
-continued
| Compound | Structure |
|---|---|
| Compound 19 | 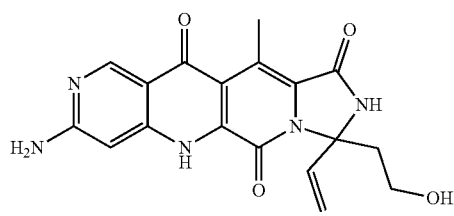 [SMILES: C=CC1(CCO)NC(=O)c2c(C)c3c(=O)c4cnc(N)cc4[nH]c3c(=O)n21] |
| Compound 20 | 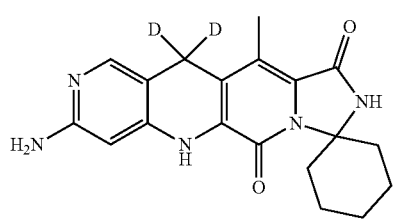 [SMILES: [2H]C1([2H])c2cnc(N)cc2Nc2c1c(C)c1n(c2=O)C2(CCCCC2)NC1=O] |
| Compound 21 | 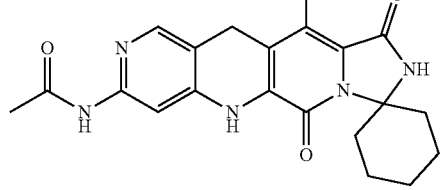 |
| Compound 22 | 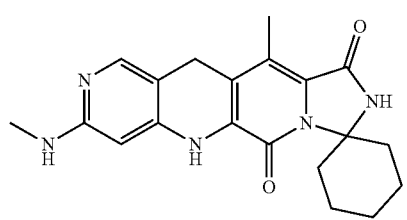 [SMILES: CNc1cc2c(cn1)Cc1c(C)c3n(c(=O)c1N2)C1(CCCCC1)NC3=O] |
| Compound 26 | 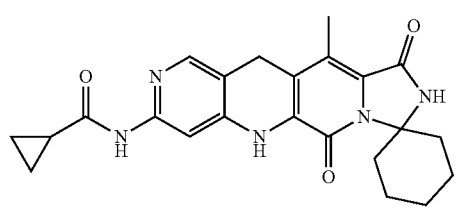 [SMILES: Cc1c2c(c(=O)n3c1C(=O)NC31CCCCC1)Nc1cc(NC(=O)C3CC3)ncc1C2] |
| Compound 28 | 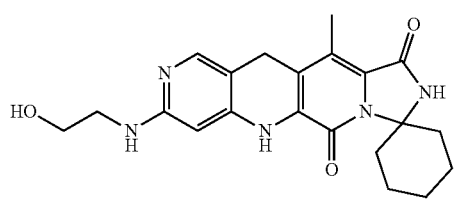 [SMILES: Cc1c2c(c(=O)n3c1C(=O)NC31CCCCC1)Nc1cc(NCCO)ncc1C2] |
| Compound 29 | 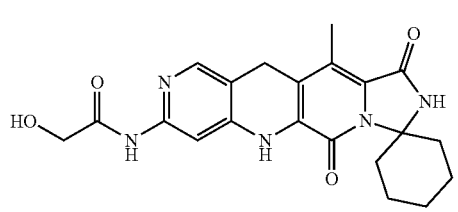 [SMILES: Cc1c2c(c(=O)n3c1C(=O)NC31CCCCC1)Nc1cc(NC(=O)CO)ncc1C2] |

| Compound | Structure |
|---|---|
| Compound 32 | 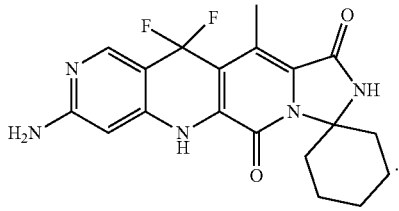 [SMILES: Cc1c2c(c(=O)n3c1C(=O)NC31CCCCC1)Nc1cc(N)ncc1C2(F)F] |

7. A pharmaceutical composition comprising: (i) a therapeutically effective amount of the compound, or the stereoisomer, tautomer, prodrug, solvate, hydrate, stable isotope derivative or pharmaceutically acceptable salt thereof according to claim 1; and optionally (ii) a pharmaceutically acceptable carrier or excipient.

8. The pharmaceutical composition of claim 7, characterized in that, the pharmaceutical composition is used for the treatment of diseases or disorders in which the activity or expression level of MNK is implicated.

9. A method for treating a disease or disorder in which the activity or expression level of MNK is implicated in a subject, comprising administering the compound, or the stereoisomer, tautomer, prodrug, solvate, hydrate, stable isotope derivative or pharmaceutically acceptable salt thereof according to claim 1 to the subject.

10. The method of claim 9, characterized in that, the disease or disorder is selected from the group consisting of: colorectal cancer, gastric cancer, thyroid cancer, lung cancer, cholangiocarcinoma, liver cancer, esophageal cancer, bladder cancer, urothelial cancer, cervical cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, multiple myeloma, brain cancer, CNS cancer, head and neck cancer, kidney cancer, prostate cancer, ovarian cancer, breast cancer, bone cancer, uncontrolled cell growth, proliferation and/or survival, inappropriate cellular immune response, inappropriate cellular inflammatory response, leukemia and myelodysplastic syndrome, malignant lymphoma, head and neck tumor, lung tumor and lung metastatic tumor, chest tumor, non-small cell tumor and small cell lung tumor, gastrointestinal tumor, endocrine tumor, breast and other gynecological tumor, urinary tumor, kidney, bladder and prostate tumor, skin tumor, sarcomas, tumor metastasis, autoimmune disease, neurodegenerative disease, Alzheimer's disease, Parkinson's disease, and neuropathic pain.

* * * * *